United States Patent
Ha et al.

(10) Patent No.: US 11,659,764 B2
(45) Date of Patent: May 23, 2023

(54) AMINE BASED COMPOUND AND ORGANIC LIGHT EMITTING DEVICE COMPRISING THE SAME

(71) Applicant: LG CHEM, LTD., Seoul (KR)

(72) Inventors: Jae Seung Ha, Daejeon (KR); Sung Jae Lee, Daejeon (KR); Hyeon Jin Mun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 370 days.

(21) Appl. No.: 16/622,227

(22) PCT Filed: Nov. 15, 2018

(86) PCT No.: PCT/KR2018/014018
§ 371 (c)(1),
(2) Date: Dec. 12, 2019

(87) PCT Pub. No.: WO2019/132246
PCT Pub. Date: Jul. 4, 2019

(65) Prior Publication Data
US 2020/0194673 A1 Jun. 18, 2020

(30) Foreign Application Priority Data

Dec. 26, 2017 (KR) .................. 10-2017-0180259
Nov. 14, 2018 (KR) .................. 10-2018-0139899

(51) Int. Cl.
*C07C 211/54* (2006.01)
*H01L 51/00* (2006.01)
(Continued)

(52) U.S. Cl.
CPC .......... *H01L 51/006* (2013.01); *C07C 211/54* (2013.01); *C07D 307/91* (2013.01);
(Continued)

(58) Field of Classification Search
None
See application file for complete search history.

(56) References Cited

U.S. PATENT DOCUMENTS 6,723,455 B2 *  4/2004  Ueda ............... C09K 11/06
                                          252/301.16
7,274,141 B2    9/2007  Leo et al.
(Continued)

FOREIGN PATENT DOCUMENTS

CN    101423757    5/2009
CN    102265424    11/2011
(Continued)

OTHER PUBLICATIONS

Tang et al. "Highly efficient deep-blue electroluminescence based on the triphenylamine-cored and peripheral blue emitters with segregative HOMO-LUMO characteristics" J. Mater. Chem. 2012, 22, 4401-4408. (Year: 2012).*
(Continued)

*Primary Examiner* — Robert S Loewe
(74) *Attorney, Agent, or Firm* — Dentons US LLP

(57) ABSTRACT

Provided is an amine based compound of Chemical Formula 1:

(Continued)

and an organic electroluminescent device comprising the same. The amine based compound can be used as a material of an organic material layer of an organic electroluminescent device, and can achieve an improvement of the efficiency, a low driving voltage and/or an improvement of the lifetime characteristic when applied to the organic electroluminescent device.

10 Claims, 1 Drawing Sheet

(51) Int. Cl.
*C07D 307/91* (2006.01)
*C09K 11/06* (2006.01)
*H01L 51/50* (2006.01)

(52) U.S. Cl.
CPC .......... *C09K 11/06* (2013.01); *H01L 51/0061* (2013.01); *C09K 2211/1007* (2013.01); *C09K 2211/1011* (2013.01); *C09K 2211/1018* (2013.01); *H01L 51/0058* (2013.01); *H01L 51/0073* (2013.01); *H01L 51/5012* (2013.01); *H01L 51/5056* (2013.01); *H01L 51/5072* (2013.01); *H01L 51/5088* (2013.01); *H01L 51/5092* (2013.01)

(56) References Cited

U.S. PATENT DOCUMENTS

| | | | | |
|---|---|---|---|---|
| 2001/0008711 A1* | 7/2001 | Igarashi | ................ | C07C 217/80 428/690 |
| 2004/0137274 A1 | 7/2004 | Igarashi | | |
| 2011/0031877 A1* | 2/2011 | Takada | ................ | C09K 11/06 313/504 |
| 2011/0198581 A1* | 8/2011 | Yabunouchi | ......... | C07D 209/56 257/40 |
| 2011/0315965 A1 | 12/2011 | Takashima et al. | | |
| 2012/0012832 A1* | 1/2012 | Yabunouchi | .......... | C09B 57/008 257/40 |
| 2012/0199820 A1* | 8/2012 | Ito | ........................ | H01L 51/006 257/E51.026 |
| 2013/0082251 A1* | 4/2013 | Park | ................... | C08G 73/0266 257/40 |
| 2013/0299806 A1* | 11/2013 | Kato | ..................... | C07C 211/61 257/40 |
| 2016/0043316 A1* | 2/2016 | Takada | ................ | H01L 51/0094 546/281.1 |
| 2016/0372677 A1* | 12/2016 | Miyake | ................ | C07D 307/91 |
| 2018/0114907 A1* | 4/2018 | Takada | ................. | C07C 211/56 |
| 2018/0123042 A1 | 5/2018 | Cha et al. | | |
| 2018/0222844 A1 | 8/2018 | Kato et al. | | |
| 2018/0226585 A1 | 8/2018 | Park et al. | | |
| 2019/0006591 A1 | 1/2019 | Yamaki et al. | | |

FOREIGN PATENT DOCUMENTS

| | | | | |
|---|---|---|---|---|
| EP | 1191821 A1 | 3/2002 | | |
| EP | 1267428 A2 | 12/2002 | | |
| EP | 1289015 A2 | 3/2003 | | |
| EP | 2372803 A1 | 10/2011 | | |
| JP | 2001192652 | 7/2001 | | |
| JP | 2002175883 | 6/2002 | | |
| JP | 2002324676 | 11/2002 | | |
| JP | 2002324678 | 11/2002 | | |
| JP | 2002329577 | 11/2002 | | |
| JP | 2004014335 | 1/2004 | | |
| JP | 2004047443 | 2/2004 | | |
| JP | 2004087245 | 3/2004 | | |
| JP | 2004231547 | 8/2004 | | |
| JP | 2010222261 | 10/2010 | | |
| JP | 2010222268 | 10/2010 | | |
| JP | 5552246 | 7/2014 | | |
| KR | 10-20000051826 | 8/2000 | | |
| KR | 10-20110069077 | 6/2011 | | |
| KR | 10-20110114545 | 10/2011 | | |
| KR | 1020160035971 A | * | 4/2016 | ........... C07C 211/54 |
| KR | 10-20170001830 | 1/2017 | | |
| KR | 10-20170082995 | 7/2017 | | |
| KR | 10-20170083313 | 8/2017 | | |
| WO | 2003012890 | 2/2003 | | |
| WO | 2008069756 | 6/2008 | | |
| WO | 2016208862 | 12/2016 | | |
| WO | 2017022729 | 2/2017 | | |
| WO | 2017022730 | 2/2017 | | |
| WO | 2017119792 | 7/2017 | | |

OTHER PUBLICATIONS

Office Action of European Patent Office in Appl'n No. 18894421.9, dated Apr. 26, 2022.

\* cited by examiner

[FIG. 1]
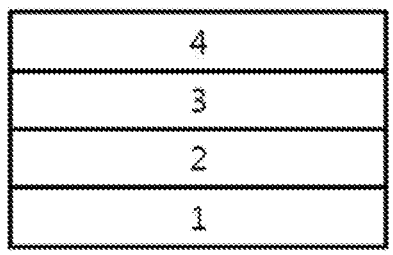
[FIG. 2]
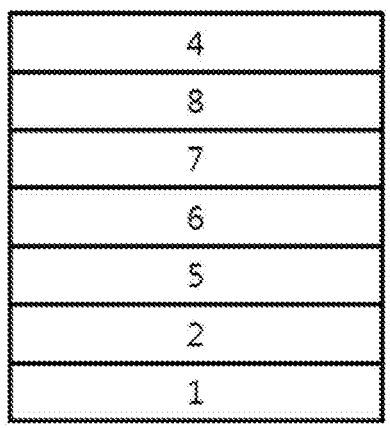
[FIG. 3]
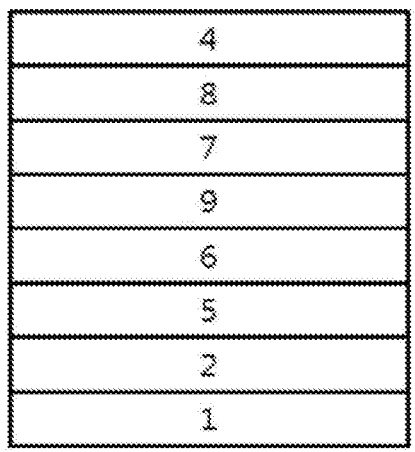

AMINE BASED COMPOUND AND ORGANIC LIGHT EMITTING DEVICE COMPRISING THE SAME

CROSS-REFERENCE TO RELATED APPLICATION(S)

This application is a Nation Stage Application of International Application No. PCT/KR2018/014018 filed on Nov. 15, 2018, which claims benefit priority based on the filing dates of Korean Patent Application No. 10-2017-0180259 filed with Korean Intellectual Property Office on Dec. 26, 2017, and Korean Patent Application No. 10-2018-0139899 filed with Korean Intellectual Property Office on Nov. 14, 2018, the entire contents of which are incorporated herein by reference.

TECHNICAL FIELD

The present invention relates to an amine based compound and an organic electroluminescent device comprising the same.

BACKGROUND

In general, an organic light emitting phenomenon refers to a phenomenon where electric energy is converted into light energy by using an organic material. The organic electroluminescent device using the organic light emitting phenomenon has characteristics such as a wide viewing angle, an excellent contrast, a fast response time, an excellent luminance, driving voltage and response speed, and thus many studies have proceeded.

The organic electroluminescent device generally has a structure which comprises an anode, a cathode, and an organic material layer interposed between the anode and the cathode. The organic material layer frequently has a multi-layered structure that comprises different materials in order to enhance efficiency and stability of the organic electroluminescent device, and for example, the organic material layer can be formed of a hole injection layer, a hole transport layer, a light emitting layer, an electron transport layer, an electron injection layer and the like.

In the structure of the organic electroluminescent device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state again.

There is a continuing need for the development of new materials for the organic materials used in such organic electroluminescent device.

PRIOR ART LITERATURE

Patent Literature (Patent Literature 1) Korean Patent Laid-open Publication No. 10-2000-0051826 (Aug. 16, 2000)

DETAILED DESCRIPTION OF THE INVENTION

Technical Problem

It is an object of the present invention to provide a novel amine based compound as an organic electroluminescent compound.

It is another object of the present invention to provide an organic electroluminescent device comprising the amine based compound.

Technical Solution

According to the present invention, there is provided a compound of the following Chemical Formula 1:

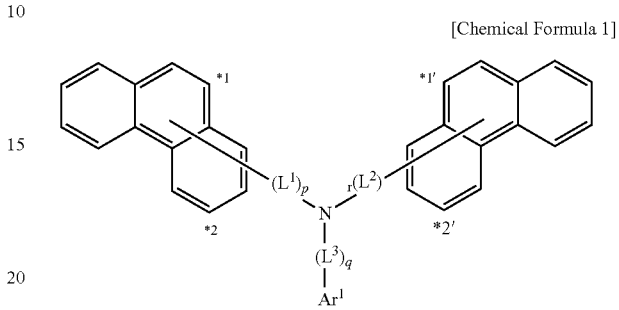

[Chemical Formula 1]

wherein in Chemical Formula 1:
$L^1$ is bonded to position *1, or *2;
$L^2$ is bonded to position *1', or *2';
$L^1$, $L^2$ and $L^3$ are each independently phenylene, biphenylene, terphenylene, 1-naphthylene, 2-naphthylene, fluorenylene, dibenzofuranylene, dibenzo-thiophenylene, or carbazolylene, wherein the $L^1$, $L^2$ and $L^3$ are each independently unsubstituted or substituted with deuterium, halogen, amino, nitrile, nitro, $C_{1-30}$ alkyl, $C_{2-30}$ alkenyl, $C_{2-30}$ alkynyl, $C_{1-30}$ alkoxy, $C_{6-30}$ aryloxy, or $C_{6-30}$ aryl;
$Ar_1$ is phenyl, biphenyl, terphenyl, fluorenyl, 9,9-dimethylfluorenyl, 9,9-diphenylfluorenyl, dibenzofuranyl, or dibenzothiophenyl, wherein the $Ar^1$ is unsubstituted or substituted with $C_{6-30}$ aryl;
p and r are each independently an integer of 1 to 4;
q is an integer of 0 to 4;
provided that when $Ar^1$ is 9,9-dimethylfluorenyl, (i) $L^1$ and $L^2$ are respectively bonded to *2 and *2', or (ii) q is an integer of 1 to 4.

In addition, according to the present invention, there is provided an organic electroluminescent device comprising a first electrode; a second electrode provided at a side opposite to the first electrode; and at least one layer of the organic material layers provided between the first electrode and the second electrode, wherein the at least one layer of the organic material layers includes the compound of Chemical Formula 1.

Advantageous Effects

The compound of Chemical Formula 1 can be used as a material of an organic material layer of an organic electroluminescent device, and can achieve an improvement of the efficiency, a low driving voltage and/or an improvement of the lifetime characteristic when applied to the organic electroluminescent device. In particular, the compound of Chemical Formula 1 can be used as hole injection, hole transport, hole injection and transport, hole adjustment, light emitting, electron transport, or electron injection materials.

BRIEF DESCRIPTION OF DRAWINGS

FIG. 1 shows an example of an organic electroluminescent device comprising a substrate 1, an anode 2, a light emitting layer 3, and a cathode 4.

FIG. 2 shows an example of an organic electroluminescent device comprising a substrate 1, an anode 2, a hole injection layer 5, a hole transport layer 6, a light emitting layer 7, an electron transport layer 8, and a cathode 4.

FIG. 3 shows an example of an organic electroluminescent device comprising a substrate 1, an anode 2, a hole injection layer 5, a hole transport layer 6, a hole adjustment layer 9, a light emitting layer 7, an electron transport layer 8, and a cathode 4.

DETAILED DESCRIPTION OF THE EMBODIMENTS

Hereinafter, a compound according embodiments of the present invention and an organic electroluminescent device comprising the same will be described in more detail to assist in the understanding of the invention.

Unless otherwise stated herein, the technical terms used herein is for the purpose of describing particular embodiments only and is not intended to limit the scope of the invention.

Further, the singular forms "a," "an" and "the" are intended to include plural forms, unless the context clearly indicates otherwise.

In addition, the meaning of the terms "comprise", "include" as used herein is intended to specify the presence of specific features, ranges, integers, steps, operations, elements and/or components, but does not preclude the presence or addition of other specific features, ranges, integers, steps, operations, elements components and/or groups.

As used herein, the notation

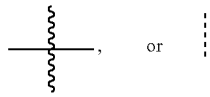

mean a bond connected to another substituent group.

As used herein, the term "substituted or unsubstituted" means being unsubstituted or substituted by one or more substituents selected from the group consisting of deuterium, a halogen group, a nitrile group, a nitro group, a hydroxyl group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, or a heterocyclic group containing at least one of N, O, and S atoms, or being unsubstituted or substituted by a substituent to which two or more substituents are linked among the exemplified substituents. For example, "the substituent to which two or more substituents are linked" can be a biphenyl group. That is, the biphenyl group can be an aryl group, or can be interpreted as a substituent to which two phenyl groups are linked.

As used herein, the alkyl group can be a straight chain or branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cycloheptylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, iso-hexyl, 2-methylpentyl, 4-methylhexyl, 5-methylhexyl, and the like, but are not limited thereto.

As used herein, the alkenyl group can be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples of the alkenyl group include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

As used herein, the alkynyl group is a monovalent group in which one atom of hydrogen is removed from an alkyne having 2 to 30 carbon atoms or a derivative thereof.

As used herein, the aryl group is not particularly limited, but preferably has 6 to 60 carbon atoms, and can be a monocyclic aryl group or a polycyclic aryl group. According to one embodiment, the aryl group has 6 to 30 carbon atoms. According to one embodiment, the aryl group has 6 to 20 carbon atoms. The aryl group can be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrycenyl group, a fluorenyl group or the like, but is not limited thereto.

As used herein, the fluorenyl group can be substituted, and two substituents can be linked with each other to form a spiro structure. In the case where the fluorenyl group is substituted,

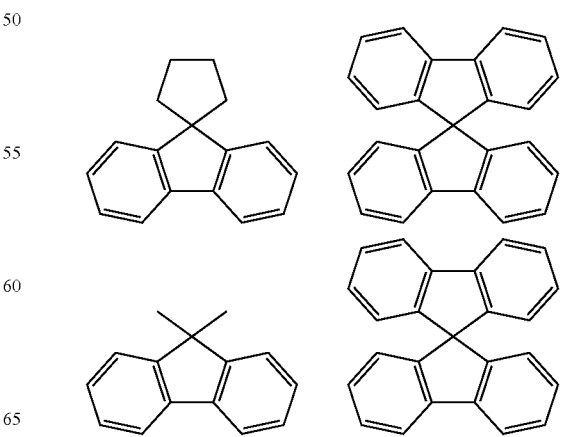

-continued

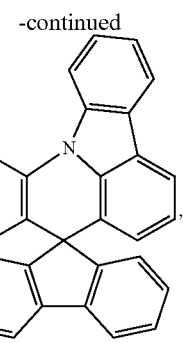

and the like can be formed. However, the structure is not limited thereto.

As used herein, the heterocyclic group is a cyclic group containing at least one of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

As used herein, the aforementioned description of the aryl group can be applied except that the arylene is a divalent group. As used herein, the aforementioned description of the heterocyclic group can be applied except that the heteroarylene is a divalent group.

Meanwhile, according to one embodiment of the invention, there is provided a compound of the following Chemical Formula 1:

[Chemical Formula 1]

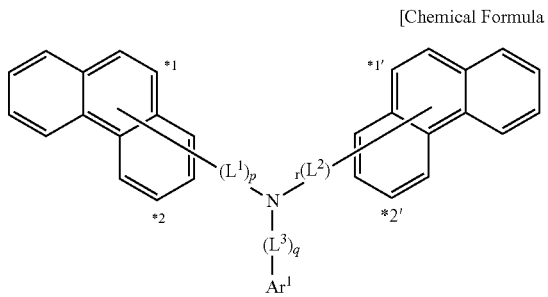

wherein in Chemical Formula 1:
$L^1$ is bonded to position *1, or *2;
$L^2$ is bonded to position *1', or *2';
$L^1$, $L^2$ and $L^3$ are each independently phenylene, biphenylene, terphenylene, 1-naphthylene, 2-naphthylene, fluorenylene, dibenzofuranylene, dibenzo-thiophenylene, or carbazolylene, wherein the $L^1$, $L^2$ and $L^3$ are each independently unsubstituted or substituted with deuterium, halogen, amino, nitrile, nitro, $C_{1-30}$ alkyl, $C_{2-30}$ alkenyl, $C_{2-30}$ alkynyl, $C_{1-30}$ alkoxy, $C_{6-30}$ aryloxy, or $C_{6-30}$ aryl;
$Ar^1$ is phenyl, biphenyl, terphenyl, fluorenyl, 9,9-dimethylfluorenyl, 9,9-diphenylfluorenyl, dibenzofuranyl, or dibenzothiophenyl, wherein the $Ar^1$ is unsubstituted or substituted with $C_{6-30}$ aryl;
p and r are each independently an integer of 1 to 4; and
q is an integer of 0 to 4,
provided that when $Ar^1$ is 9,9-dimethylfluorenyl, (i) $L^1$ and $L^2$ are respectively bonded to *2 and *2', or (ii) q is an integer of 1 to 4.

The present inventors have conducted extensive studies and have found that the compound of Chemical Formula 1 is an amine compound in which two unsubstituted phenanthrenyl groups are respectively bonded to nitrogen atoms via aromatic linking groups ($L^1$ and $L^2$) and has the above-described structural characteristics, and therefore it can be applied to an organic electroluminescent device and allow improvement of the efficiency and lifetime characteristics of the device.

According to the bonding position of the phenanthrenyl group in Chemical Formula 1, the compound of Chemical Formula 1 can be any one selected from the group consisting of the following Chemical Formulas 2-a, 2-b, and 2-c:

[Chemical Formula 2-a]

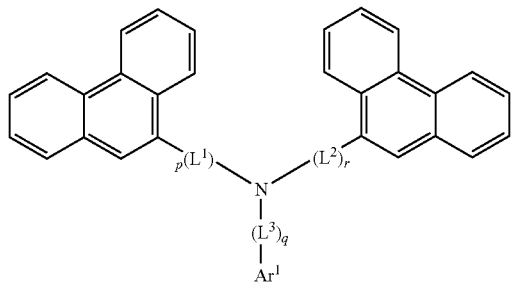

[Chemical Formula 2-b]

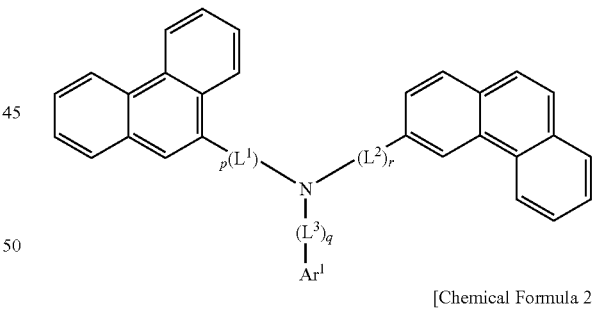

[Chemical Formula 2-c]

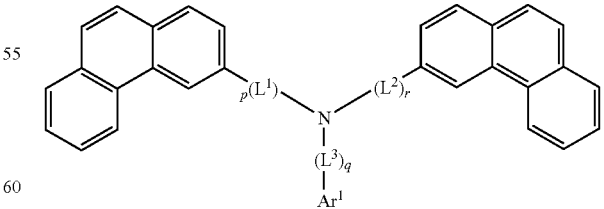

wherein in Chemical Formulas 2-a, 2-b and 2-c:
$L^1$, $L^2$, $L^3$, $Ar^1$, p, r, and q are as defined in Chemical Formula 1, respectively.

In Chemical Formula 1, $L^1$, $L^2$ and $L^3$ are the same as or different from each other, and are each independently phenylene, biphenylene, terphenylene, 1-naphthylene, 2-naphthylene, fluorenylene, dibenzofuranylene, dibenzo-thiophenylene, or carbazolylene, In one embodiment of the invention, the phenylene, biphenylene, terphenylene, 1-naphthylene, 2-naphthylene, fluorenylene, dibenzofuranylene, dibenzothiophenylene, or carbazolylene are each independently unsubstituted or substituted with deuterium, halogen, an amino group, a nitrite group, a nitro group, a $C_{1-30}$ alkyl group, a $C_{2-30}$ alkenyl group, a $C_{2-30}$ alkynyl group, a $C_{1-30}$ alkoxy group, a $C_{6-30}$ aryloxy group, or a $C_{6-30}$ aryl group.

In Chemical Formula 1, p and r can be each independently an integer of 1 to 4, and q can be an integer of 0 to 4. Herein, when q is 0, it means a case where in Chemical Formula 1, $-(L^3)_q-$ is a direct bond.

Preferably, p and r are each independently 1, and q can be 0 or 1. Preferably, p and r are each independently 1, and the $L^1$ and $L^2$ are each independently phenylene, or biphenylene.

Preferably, the q is 0 or 1, and the $L^3$ is phenylene, or naphthylene.

In one embodiment of the invention, $L^1$, $L^2$ and $L^3$ are each independently phenylene, biphenylene, terphenylene, 1-naphthylene, 2-naphthylene, fluorenylene, dibenzofuranylene, dibenzothiophenylene, or carbazolyl; p and r are each independently 1, and q can be 0.

In one embodiment of the invention, $L^1$, $L^2$ and $L^3$ are each independently phenylene, biphenylene, terphenylene, 1-naphthylene, 2-naphthylene, fluorenylene, dibenzofuranylene, dibenzothiophenylene, or carbazolylene; p and r are each independently 1, and q can be 1.

In Chemical Formula 1, $Ar^1$ is phenyl, biphenyl, terphenyl, fluorenyl, 9,9-dimethylfluorenyl, 9,9-diphenylfluorenyl, dibenzofuranyl, or dibenzothiophenyl. Further, when $Ar_1$ is substituted, it can be substituted with phenyl.

Preferably, the compound of Chemical Formula 1 can be any one selected from the group consisting of the following:

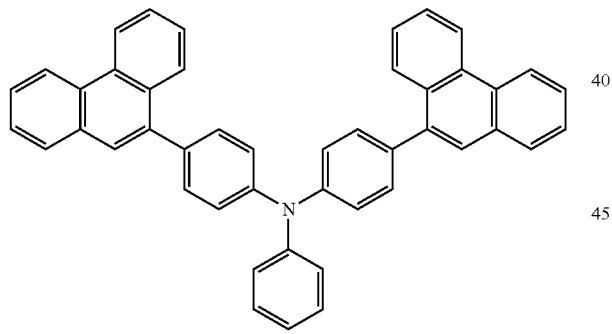

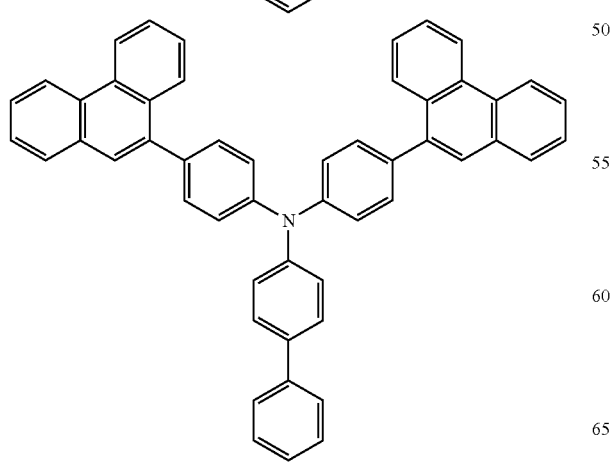

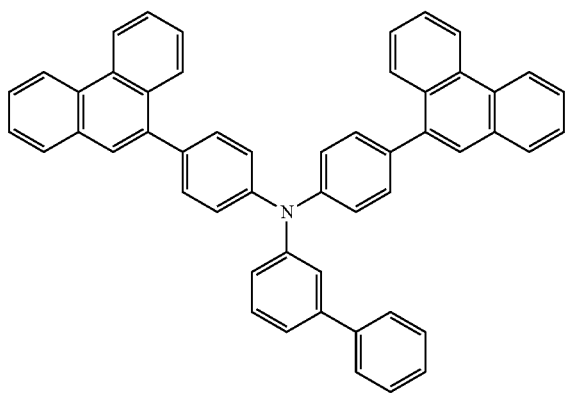

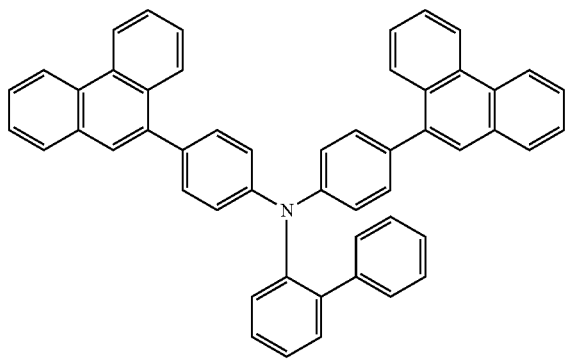

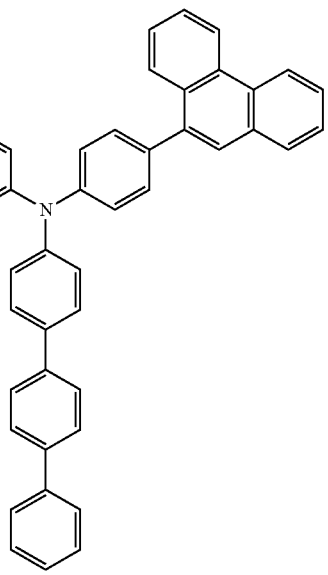

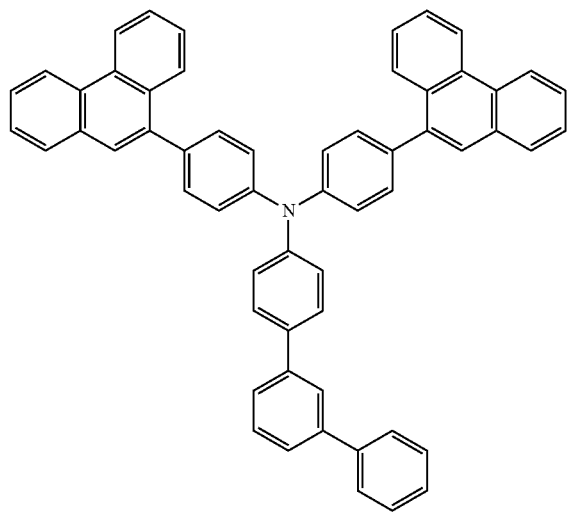
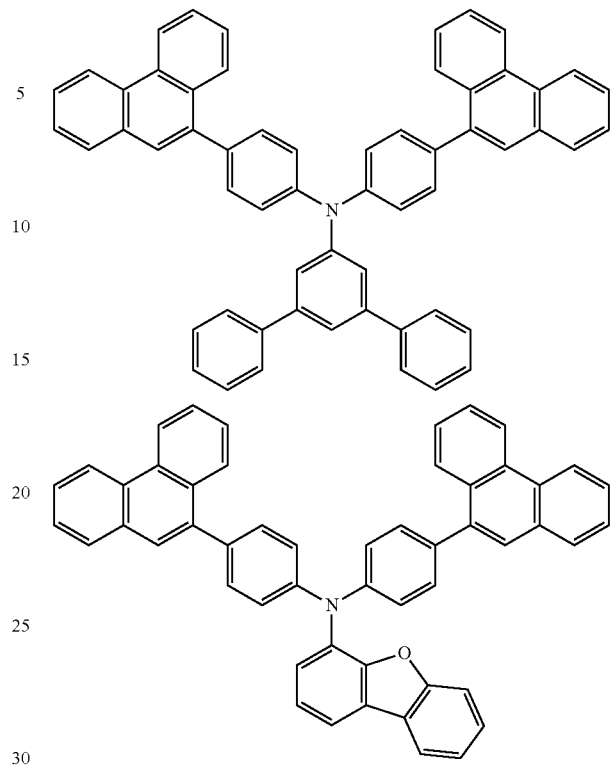
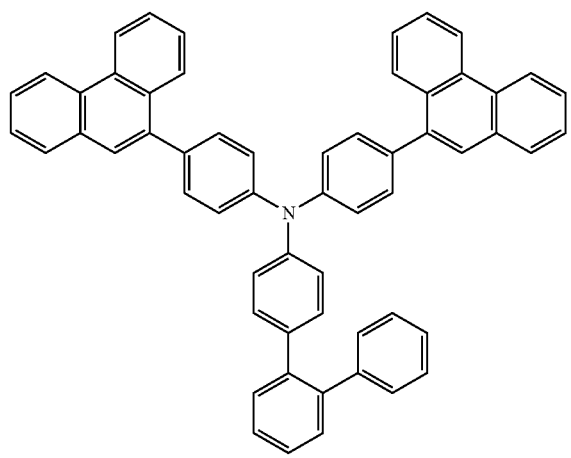
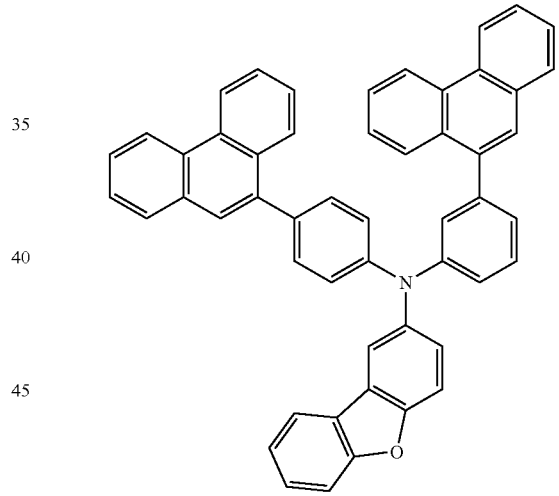
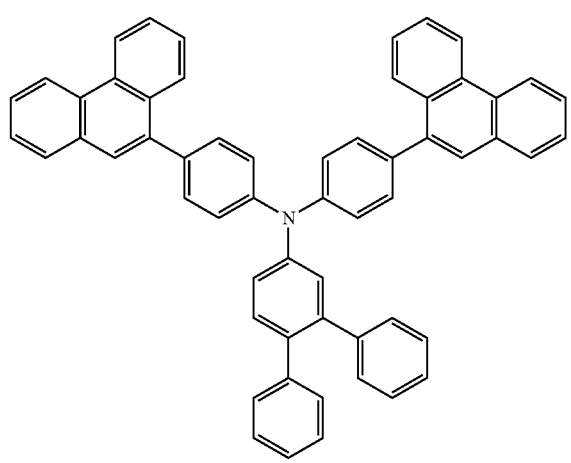
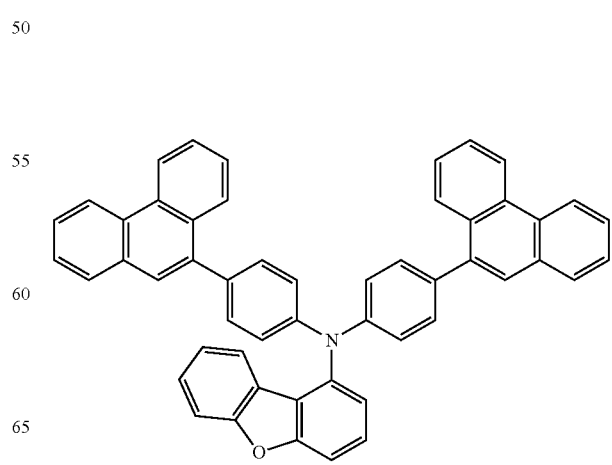

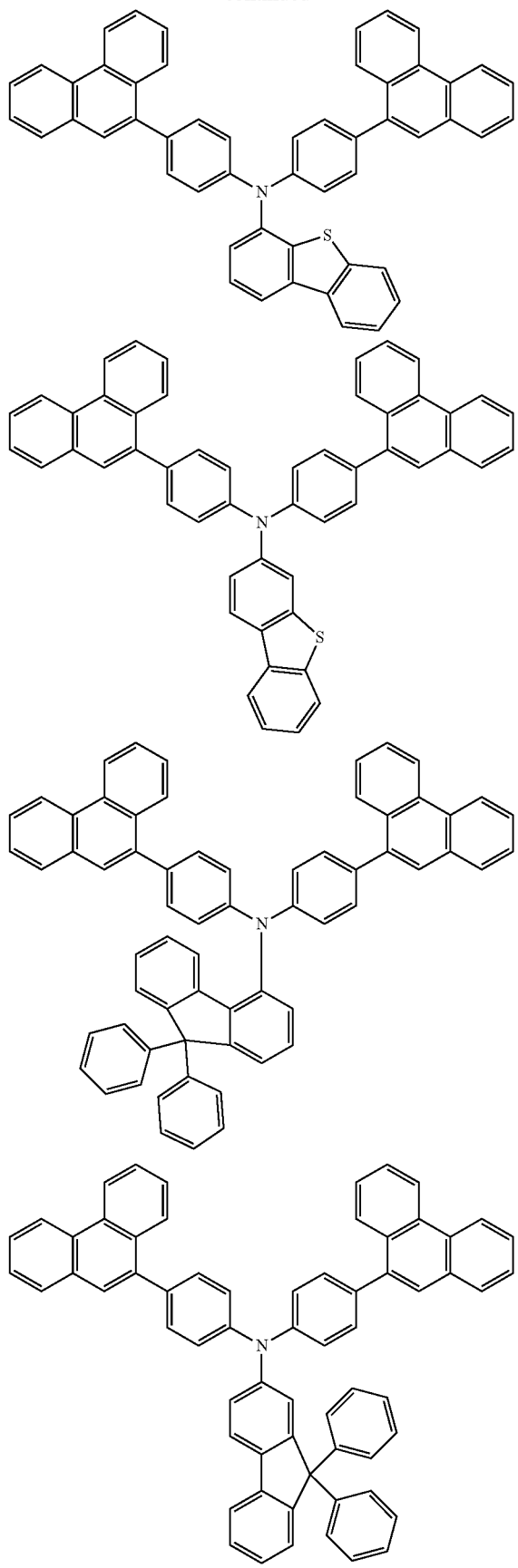
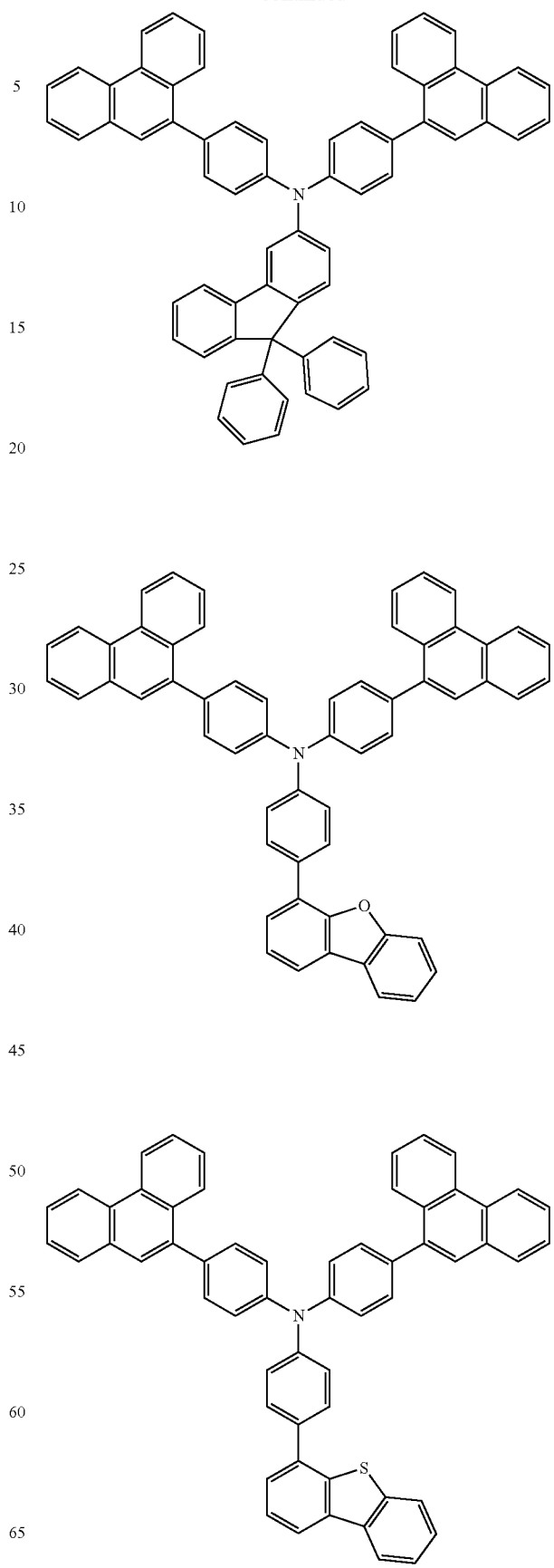

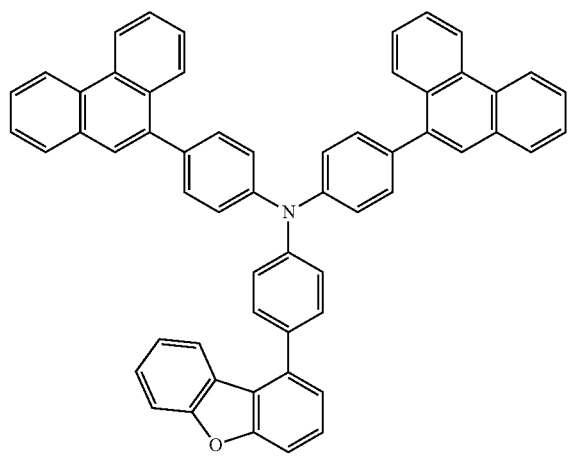
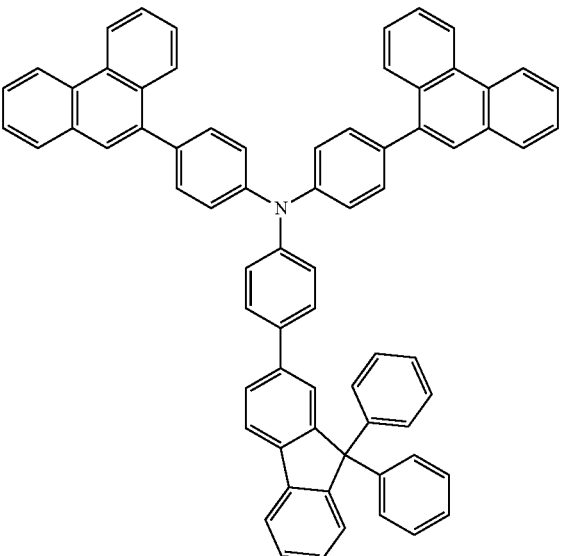
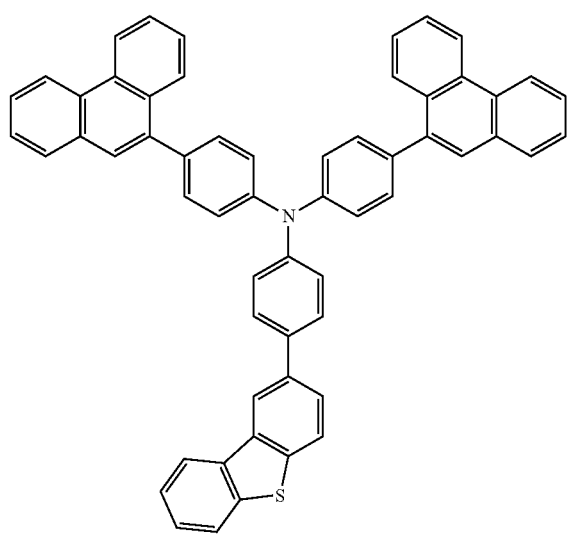
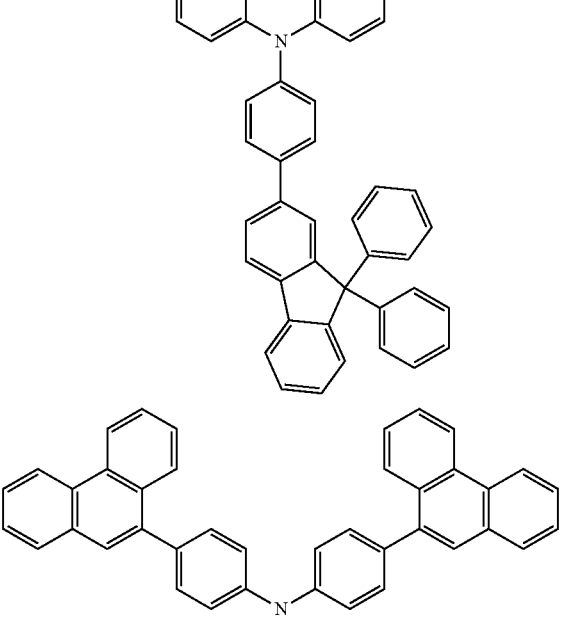
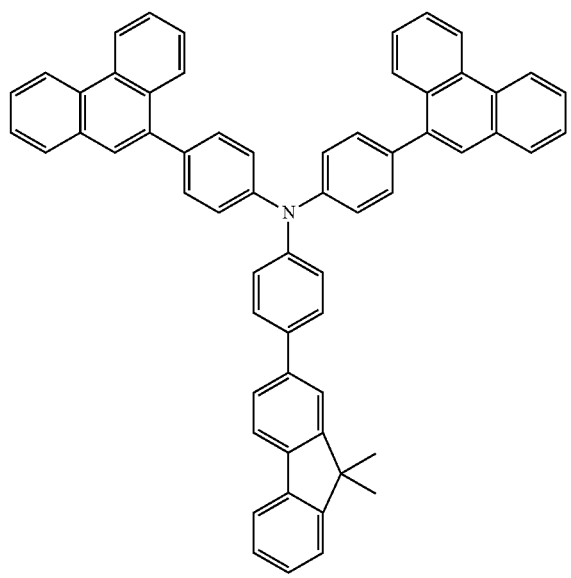
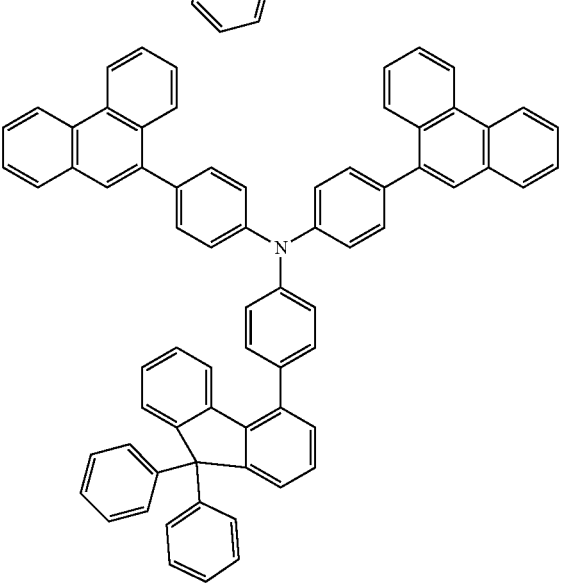

15
-continued
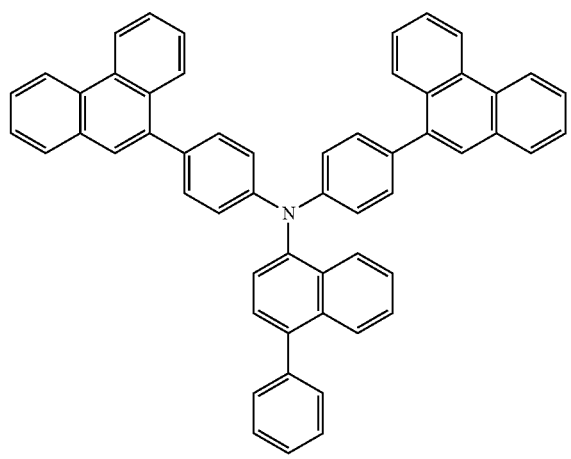
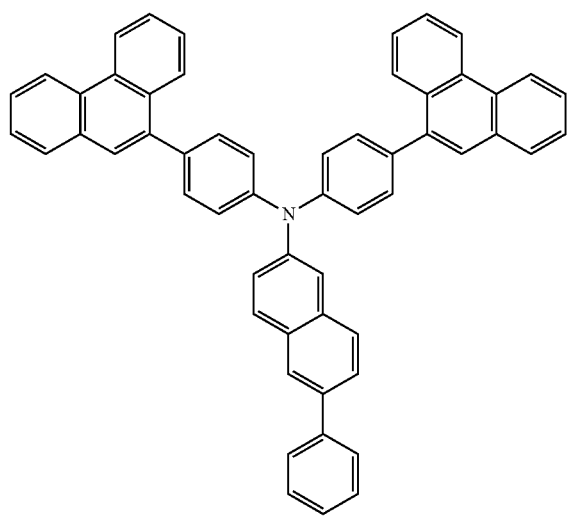
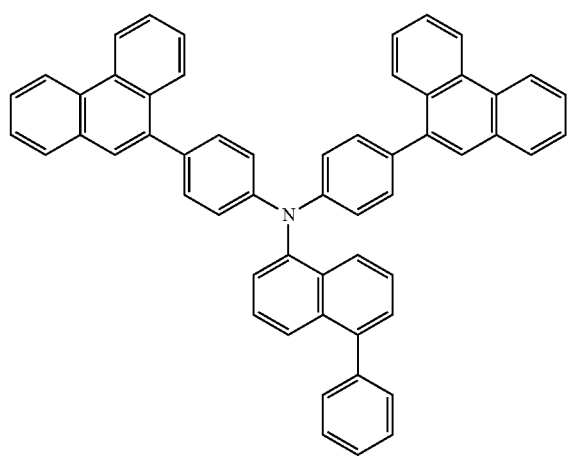
16
-continued
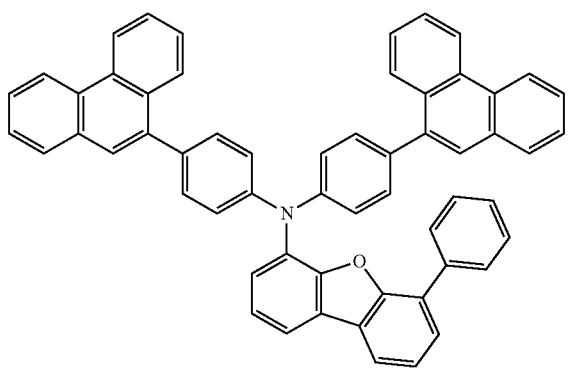
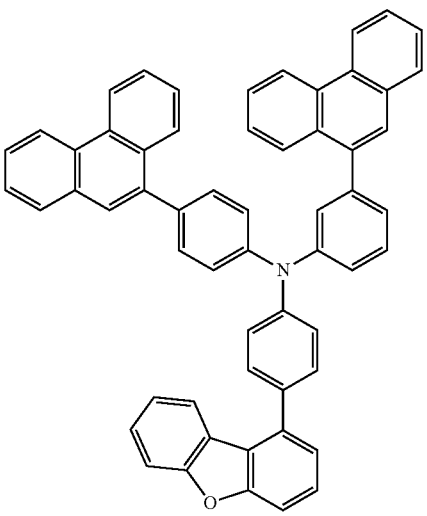
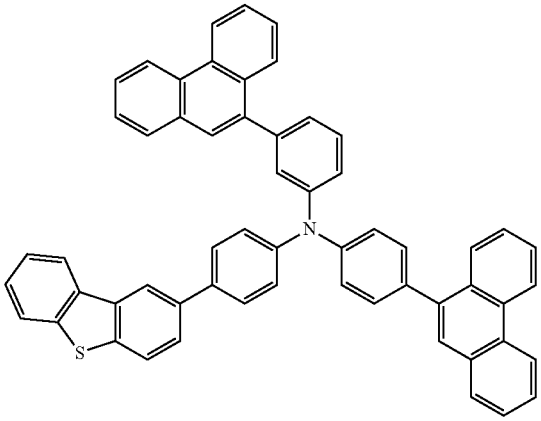

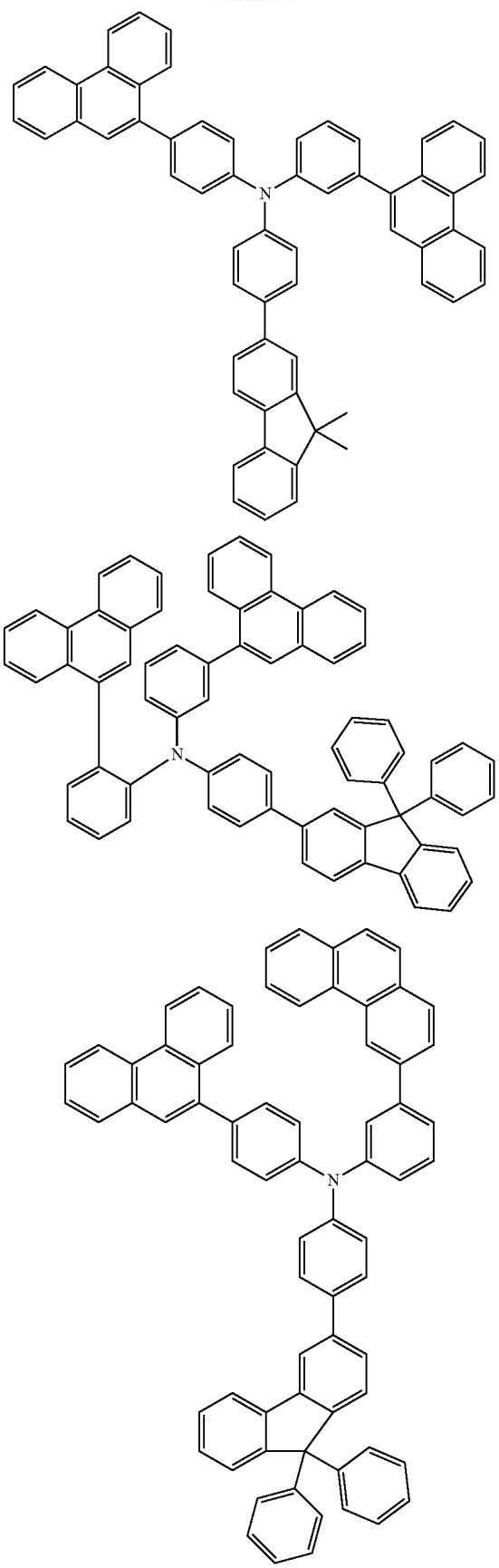
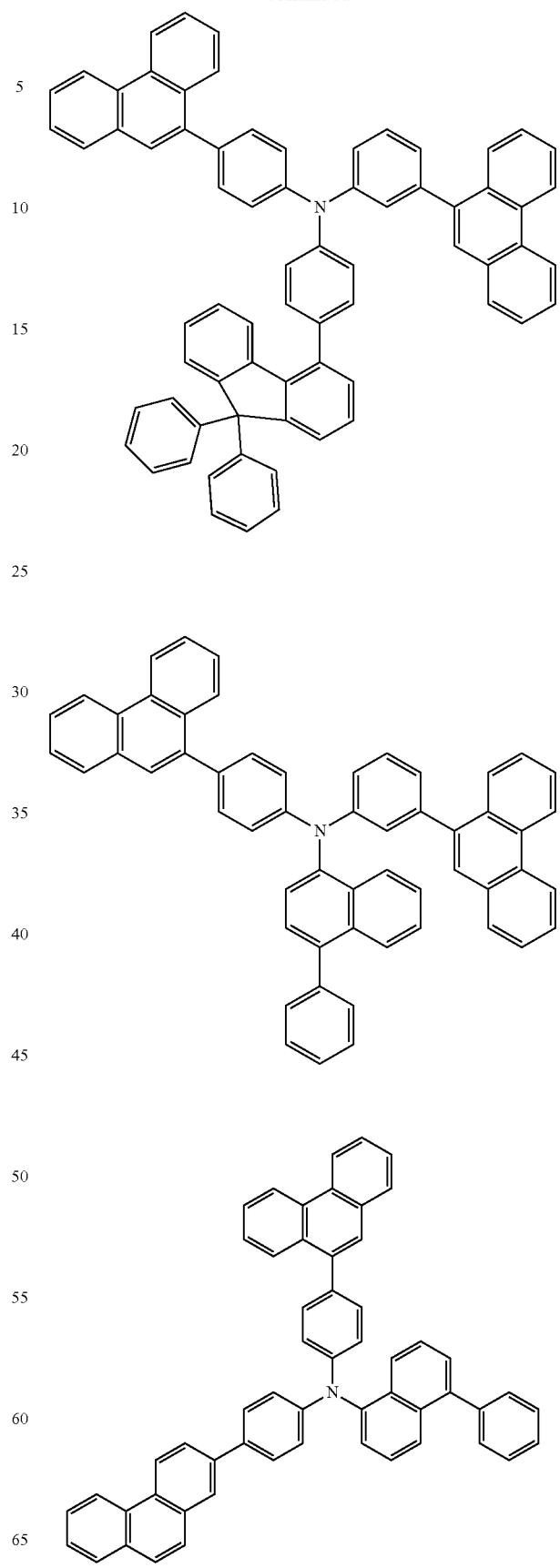

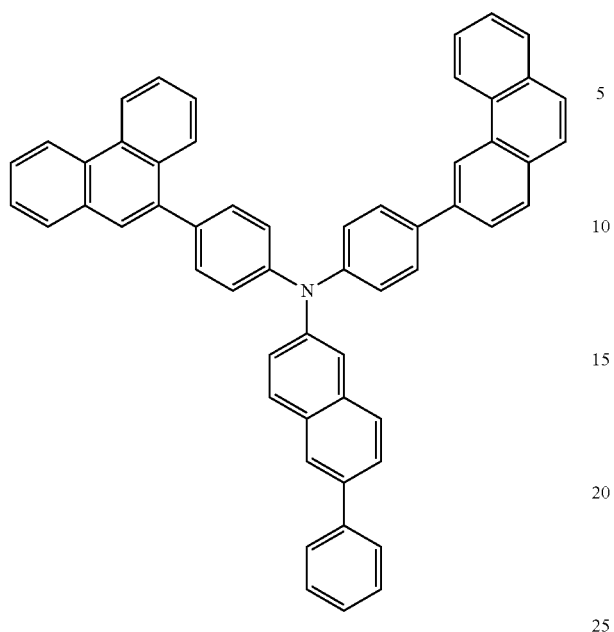
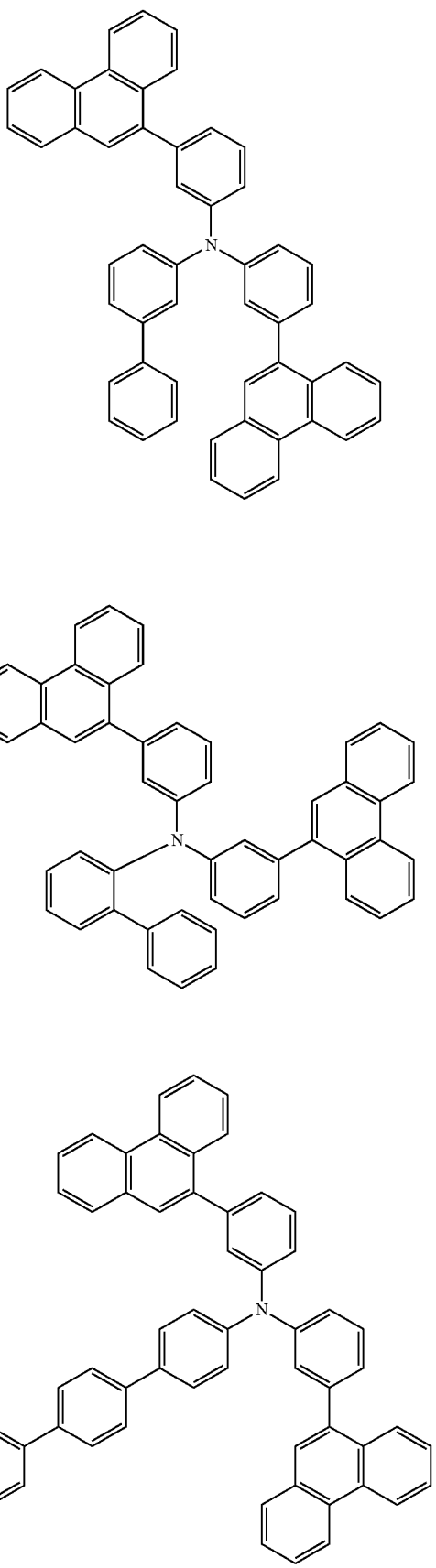

-continued
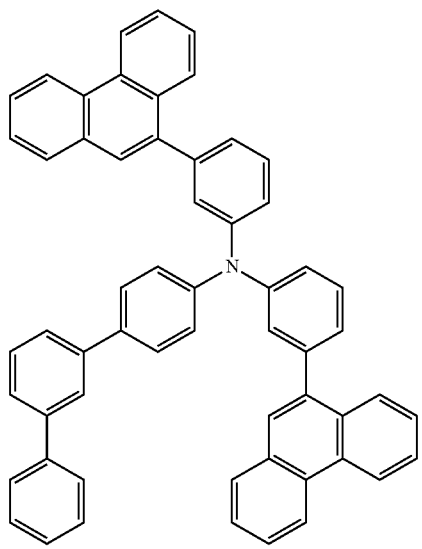
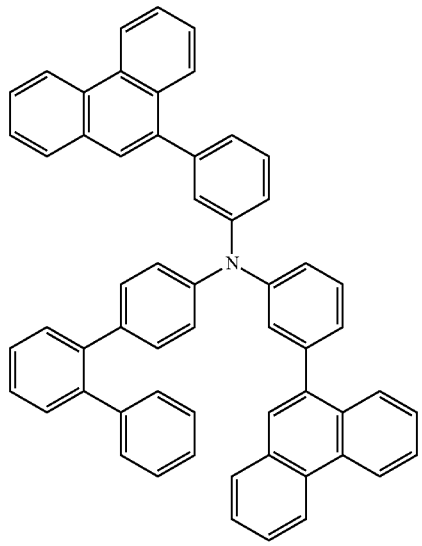
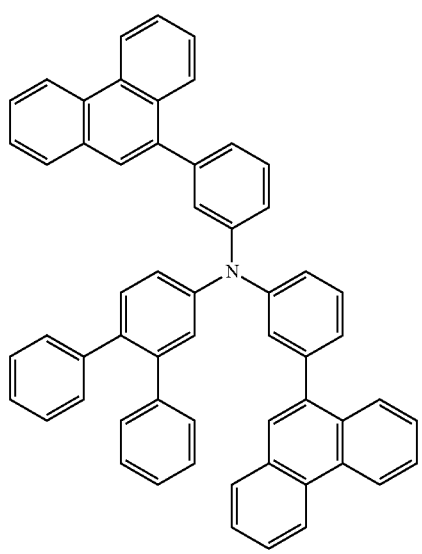
-continued
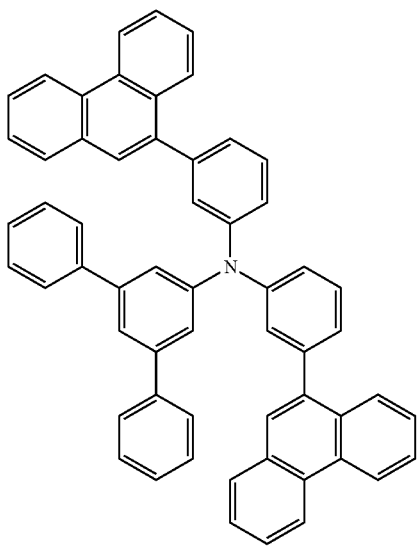
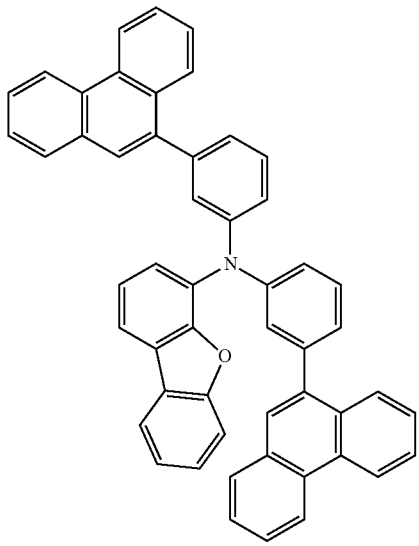
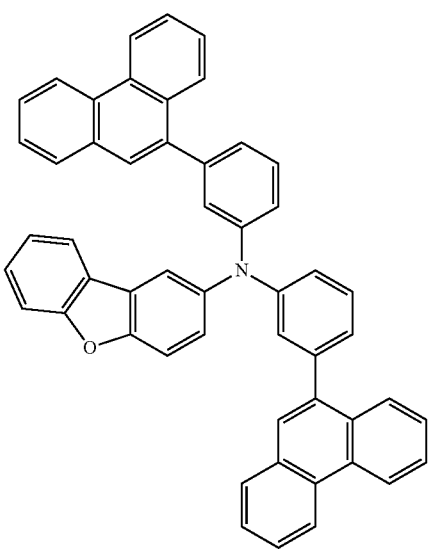

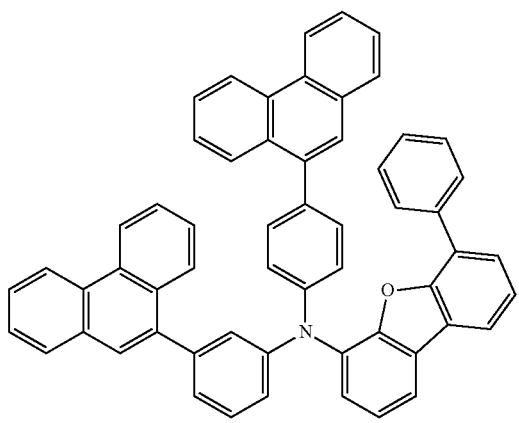
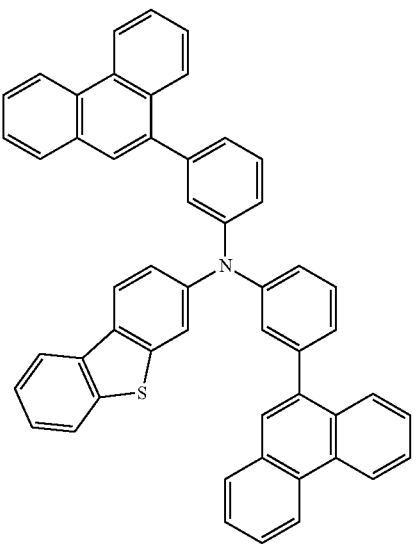
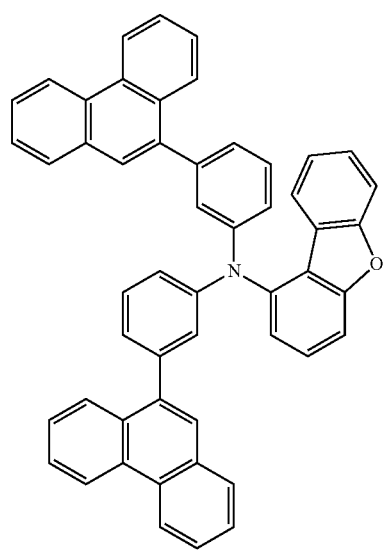
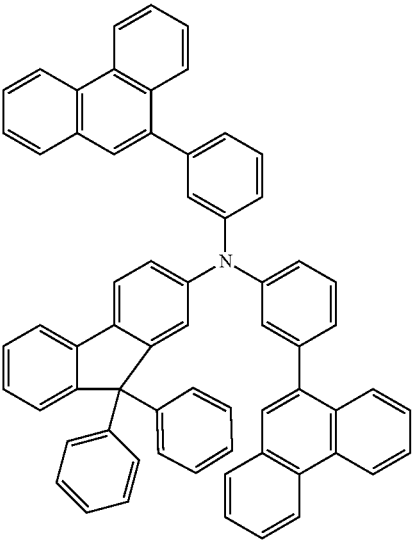
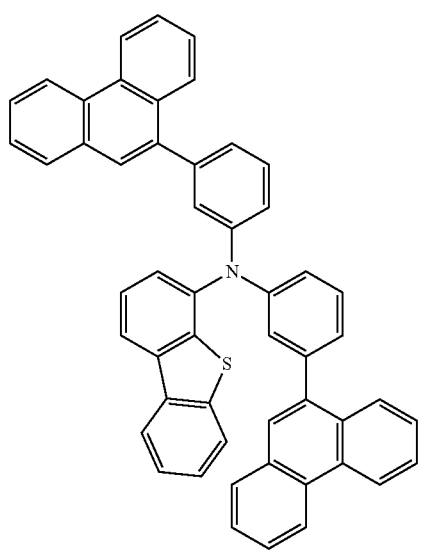
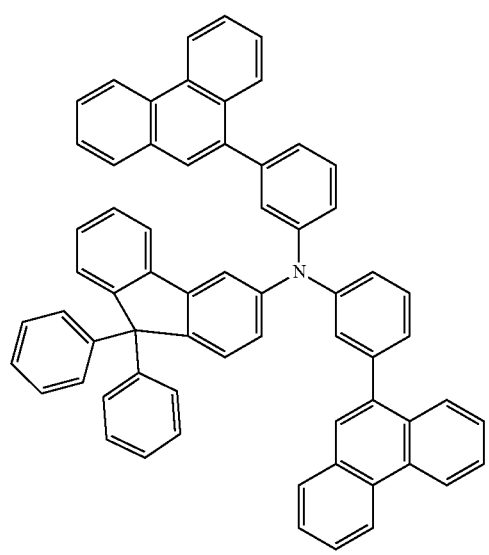

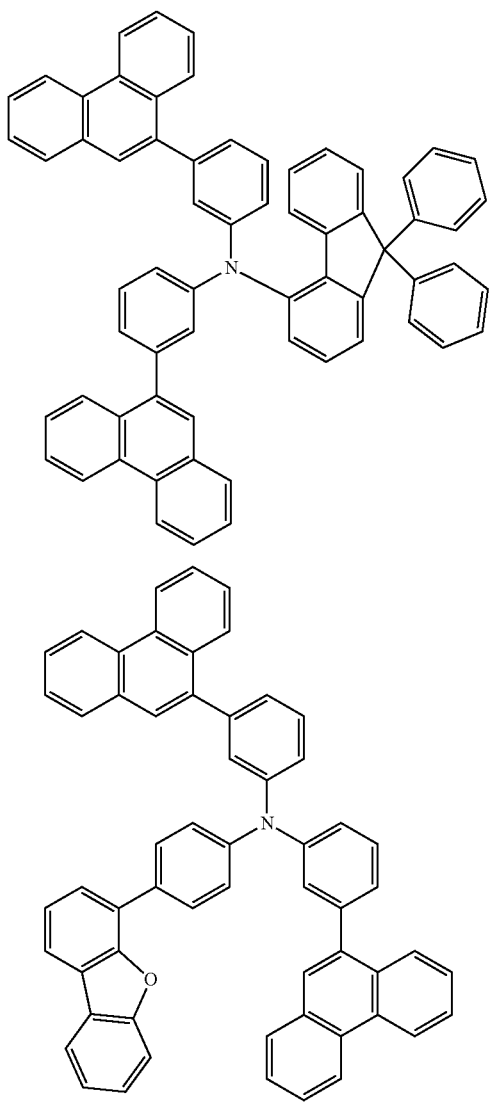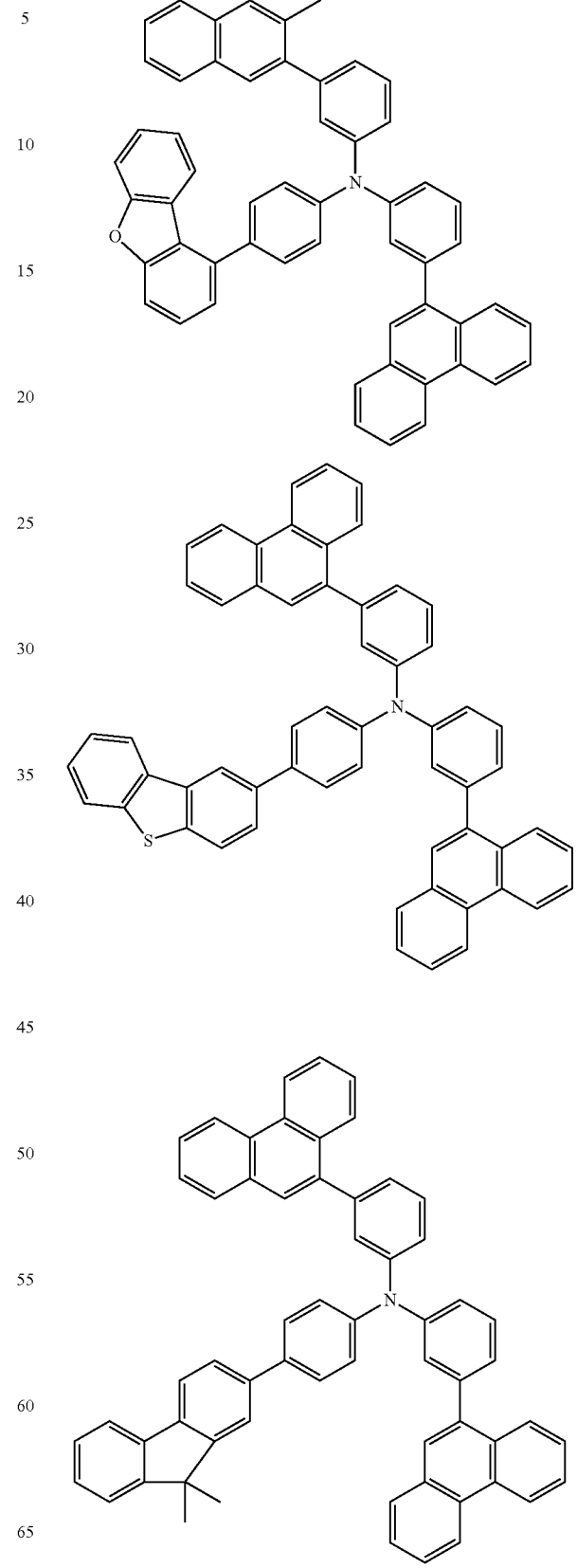

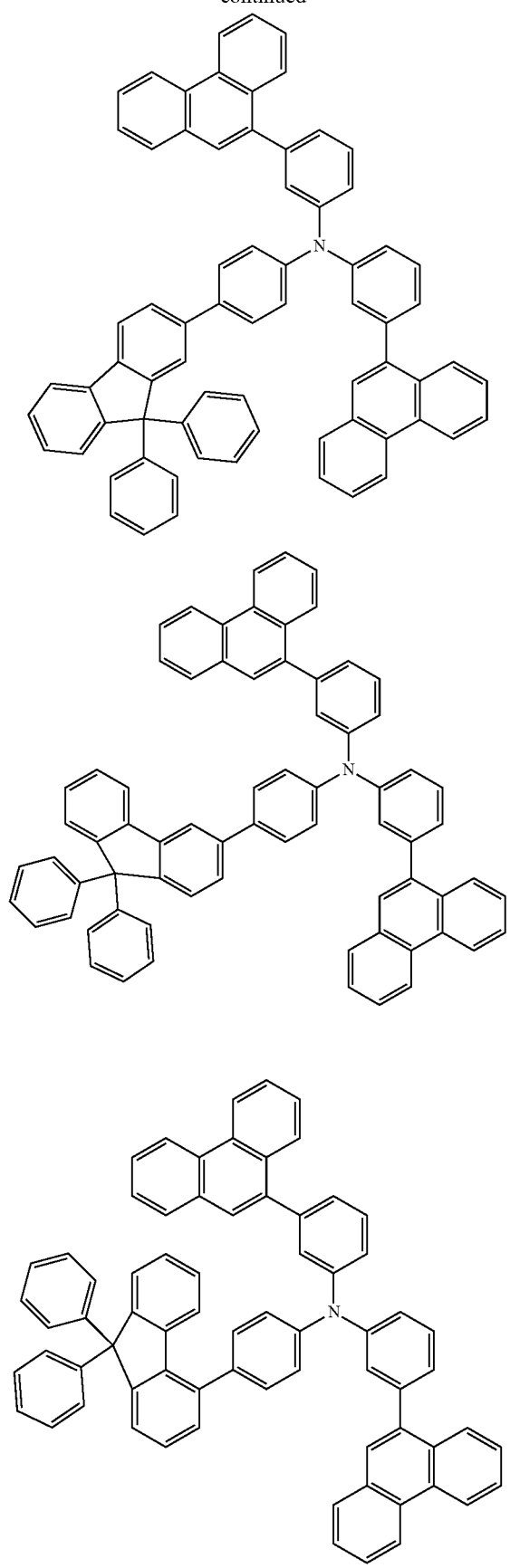
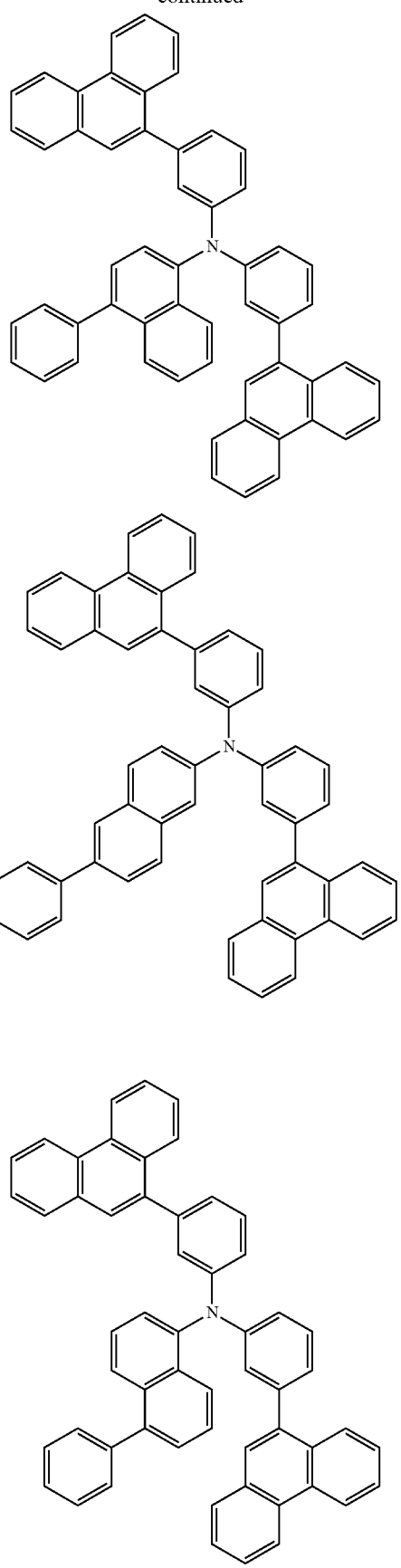

29
-continued
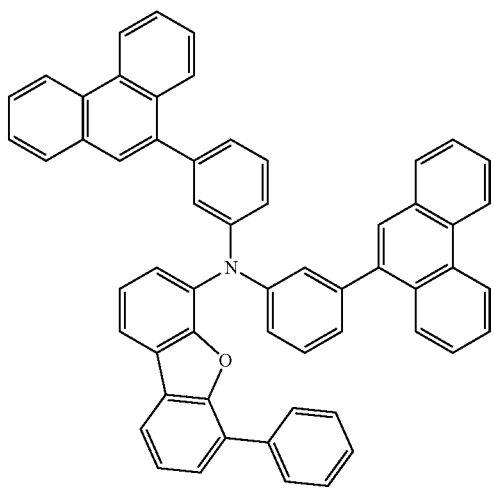
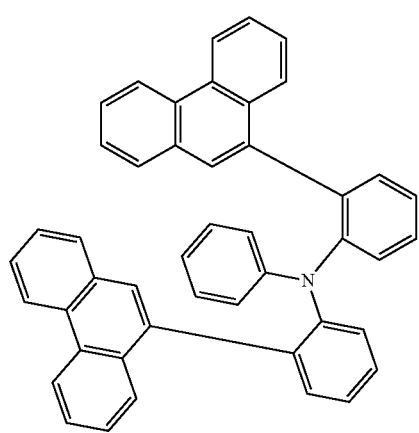
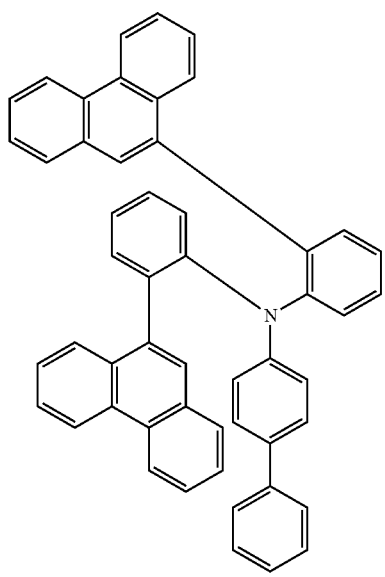
30
-continued
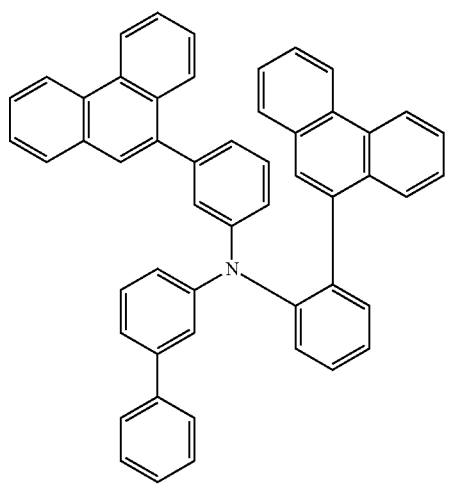
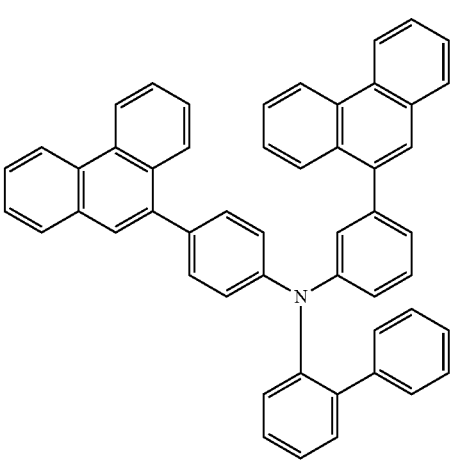
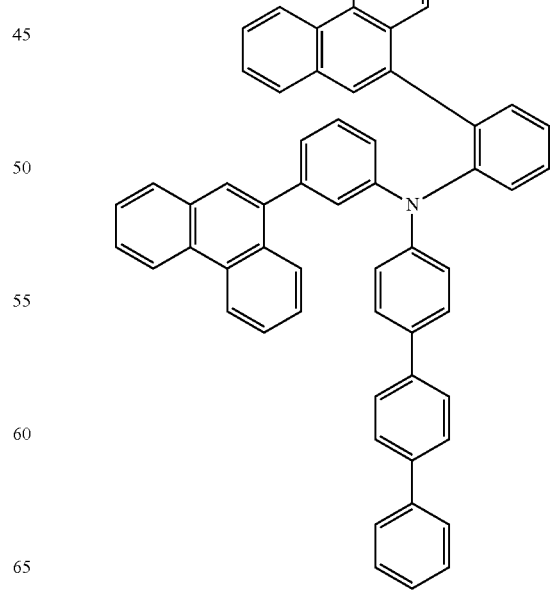

31
-continued
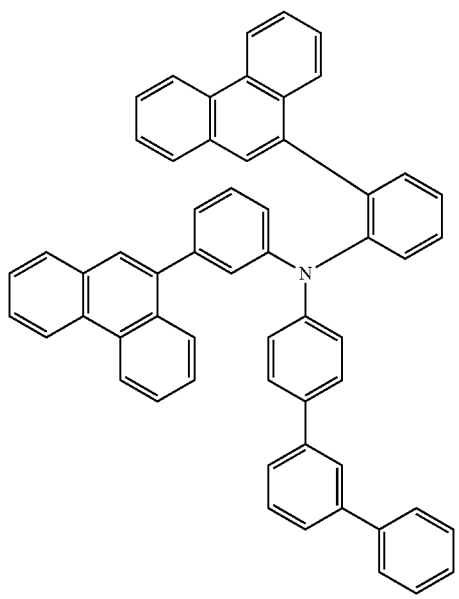
32
-continued
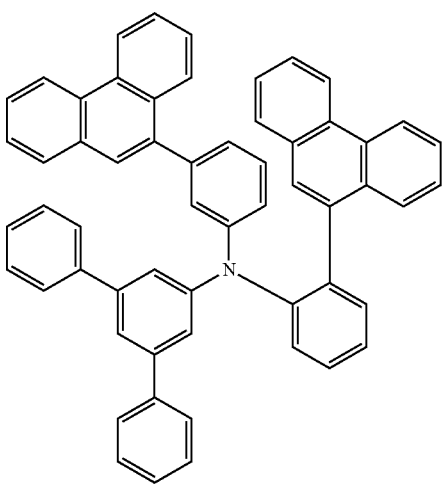
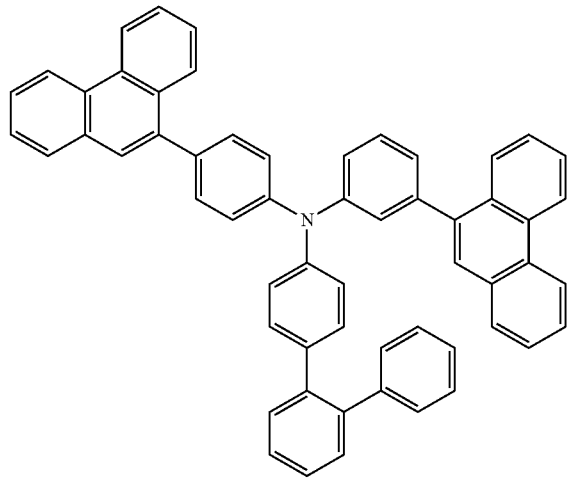
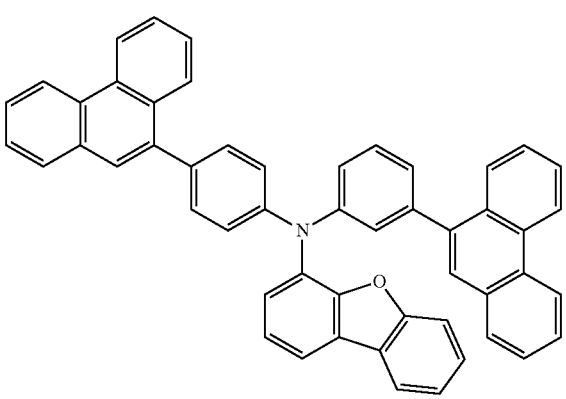
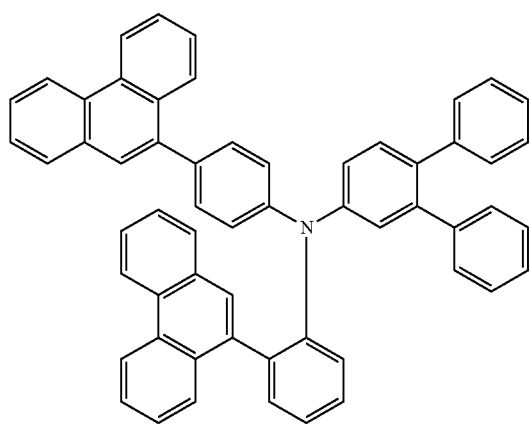
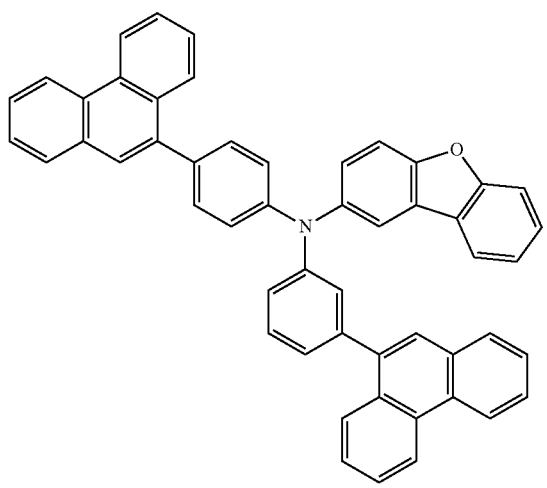

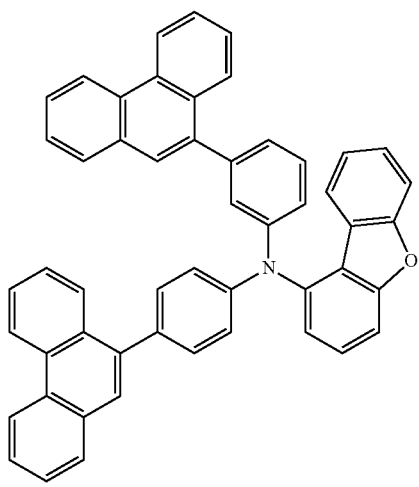
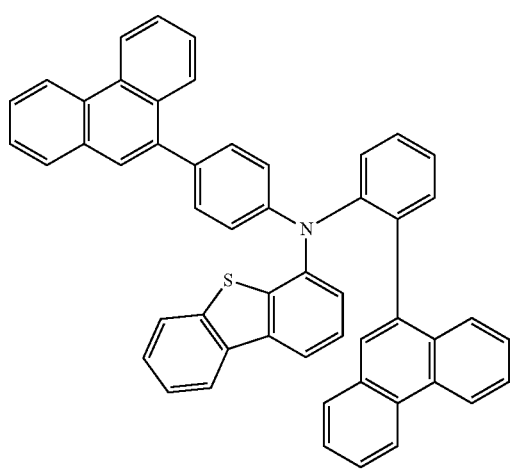
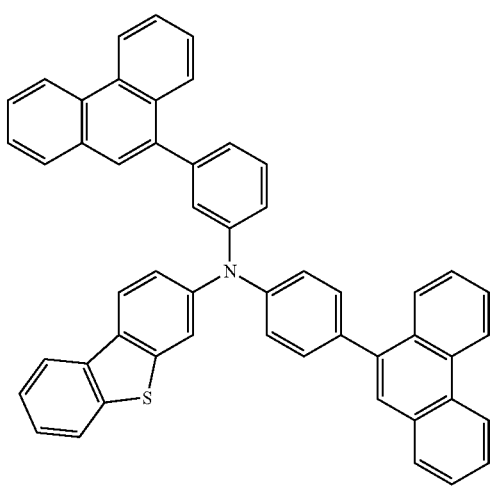
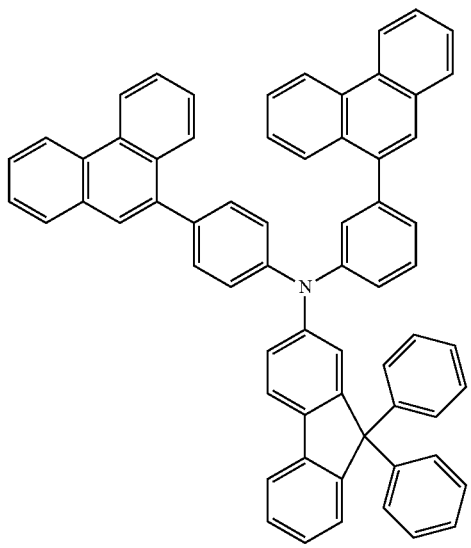
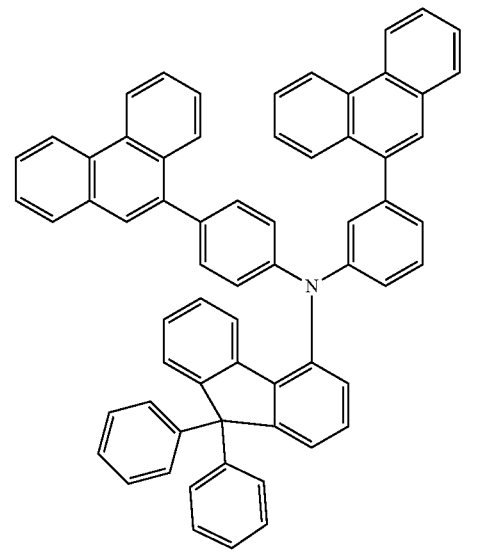

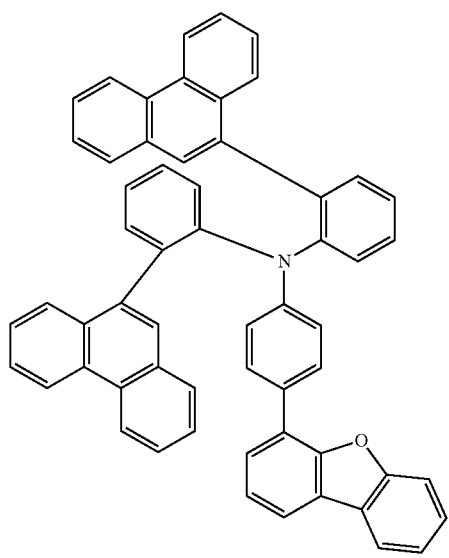
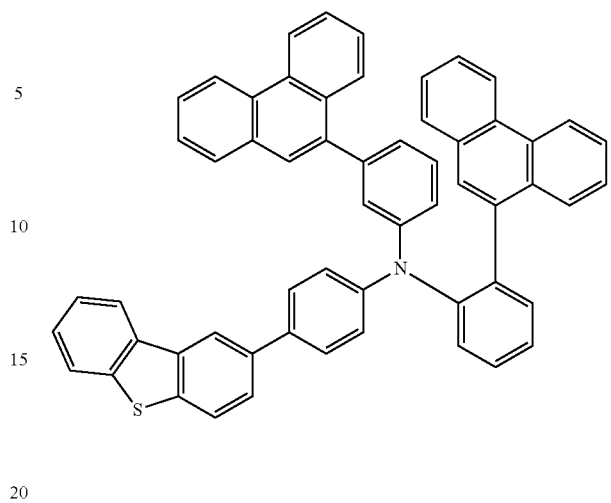
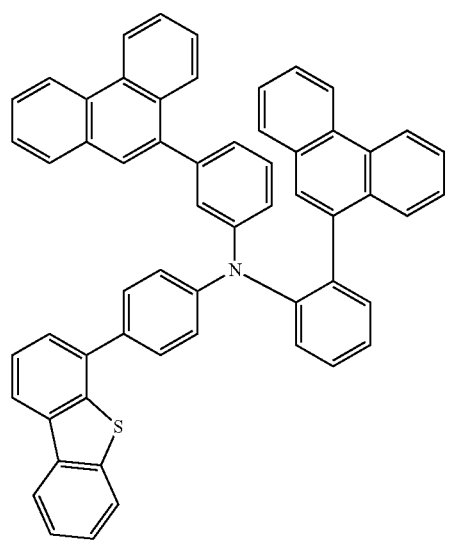
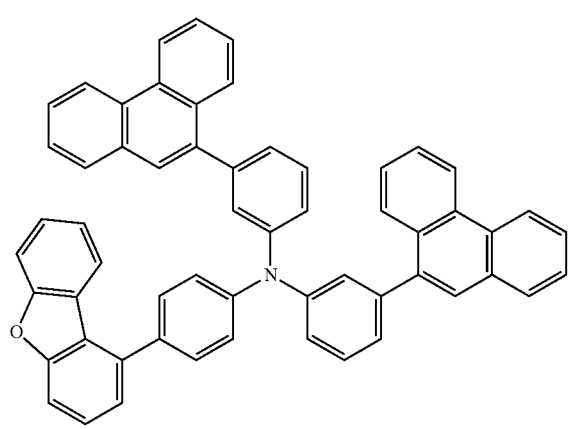
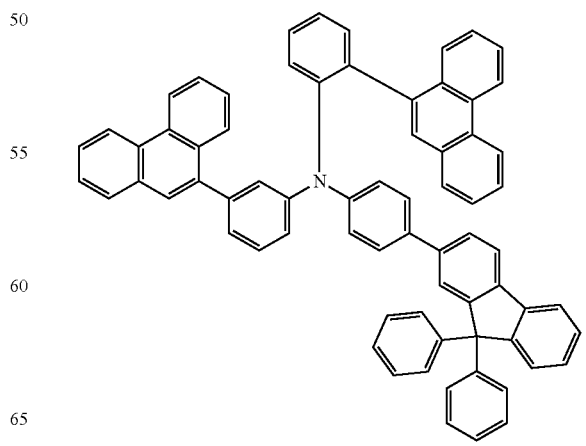

37
-continued
38
-continued
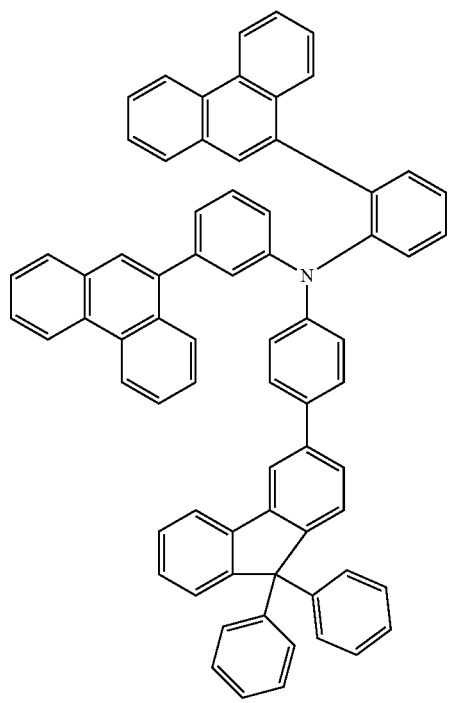
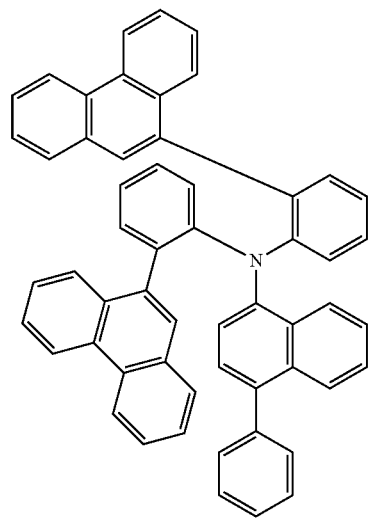
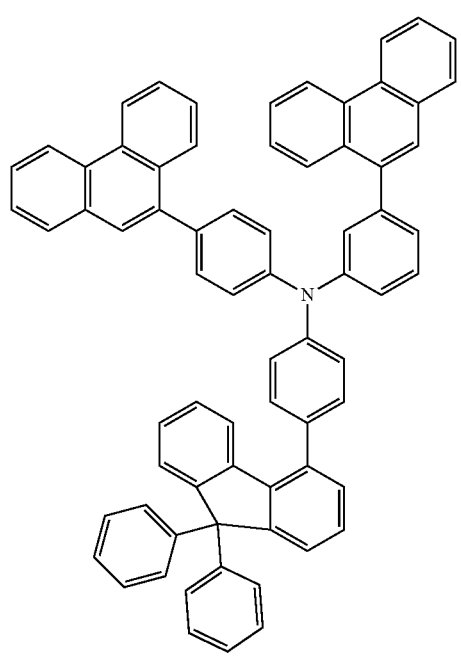

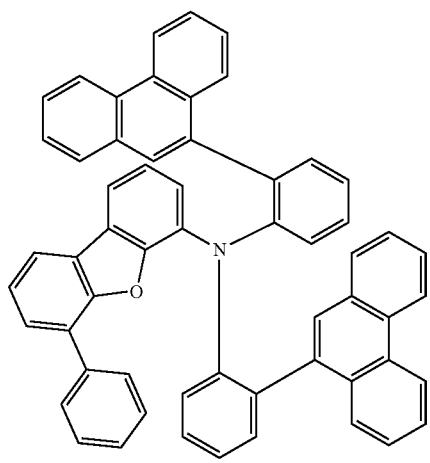
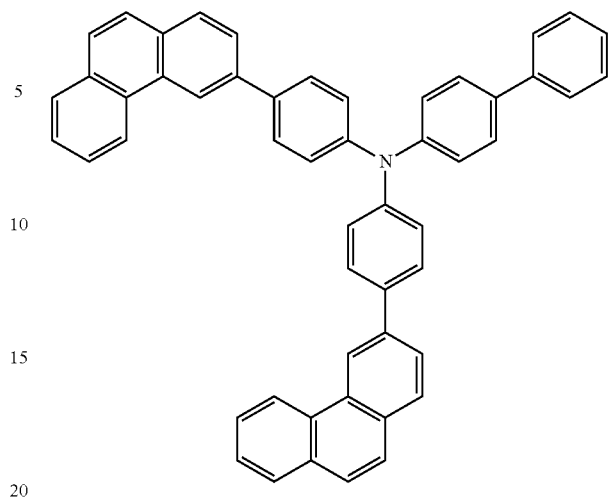
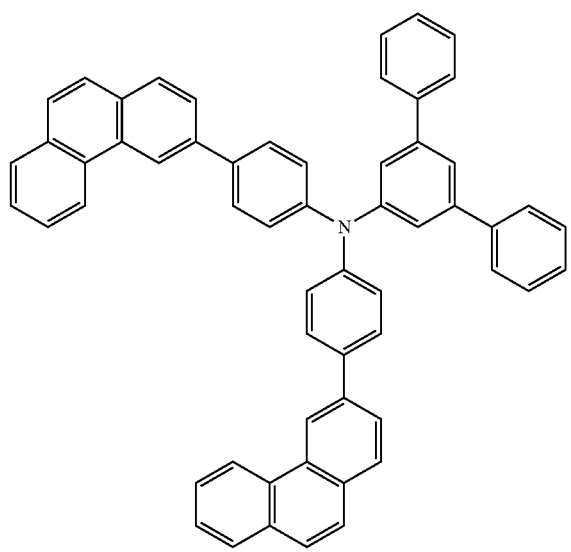
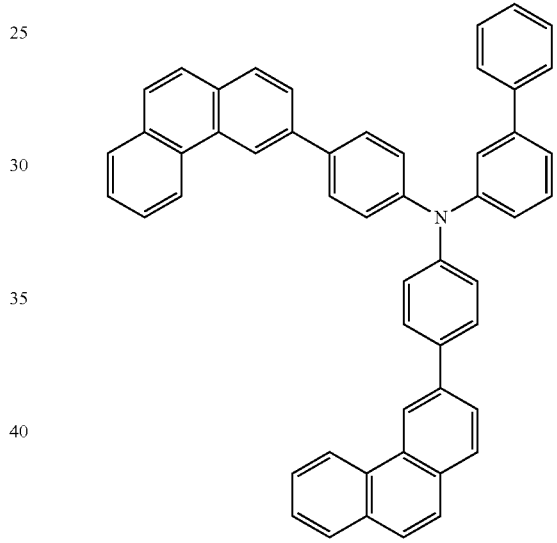
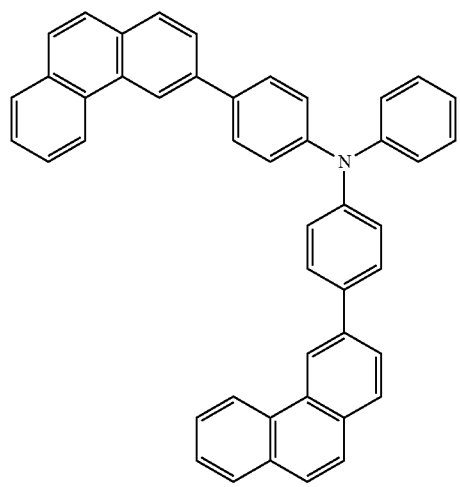
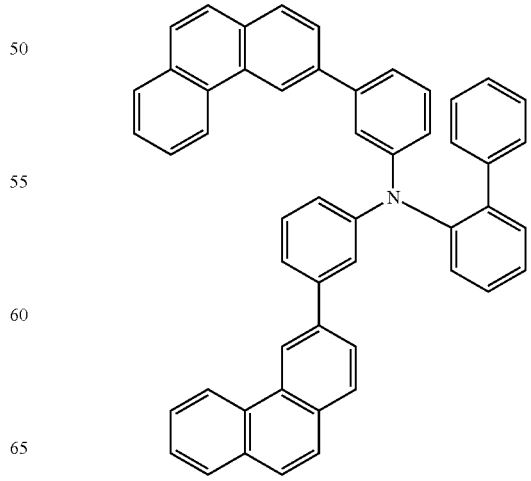

-continued
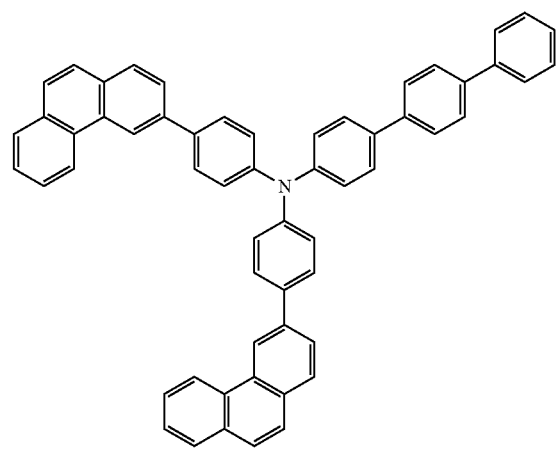
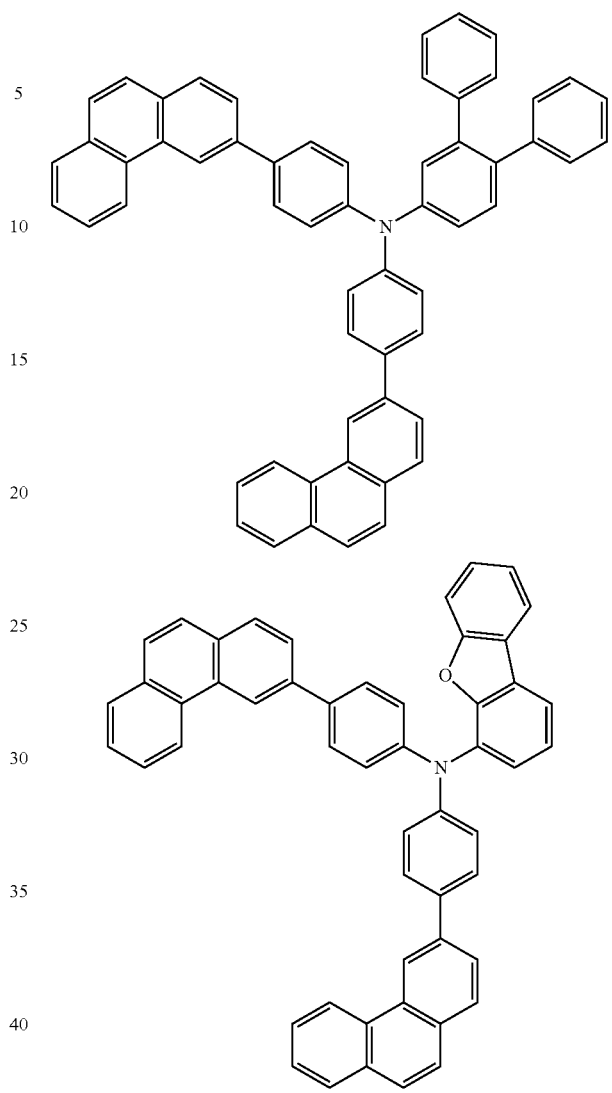
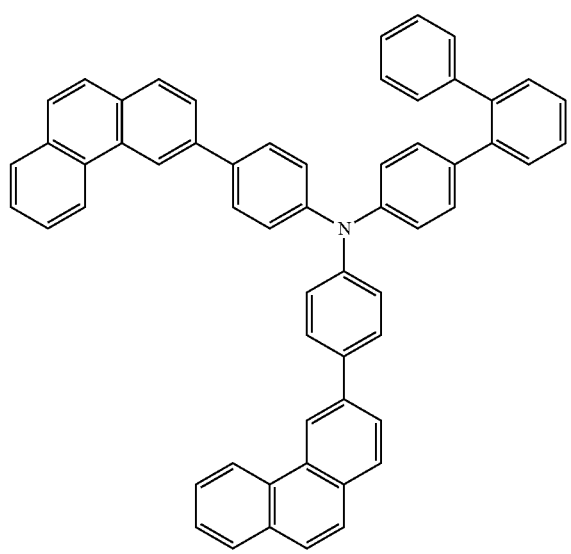
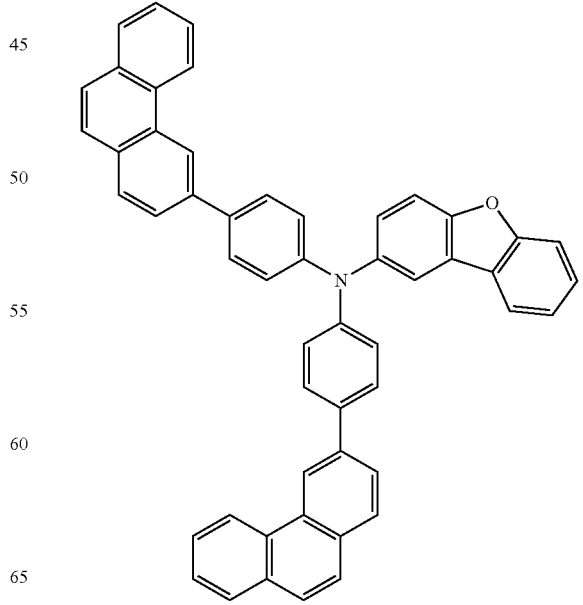

43
-continued
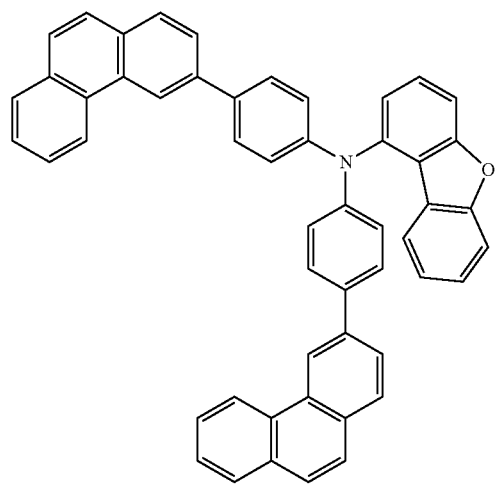
44
-continued
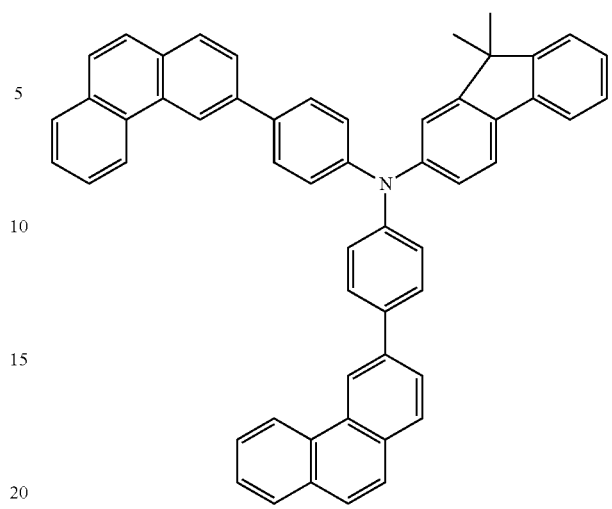
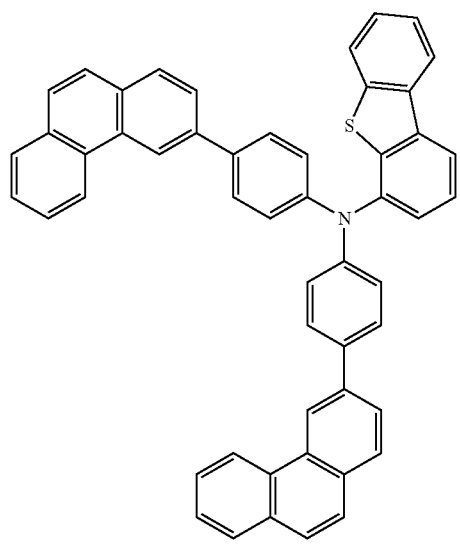
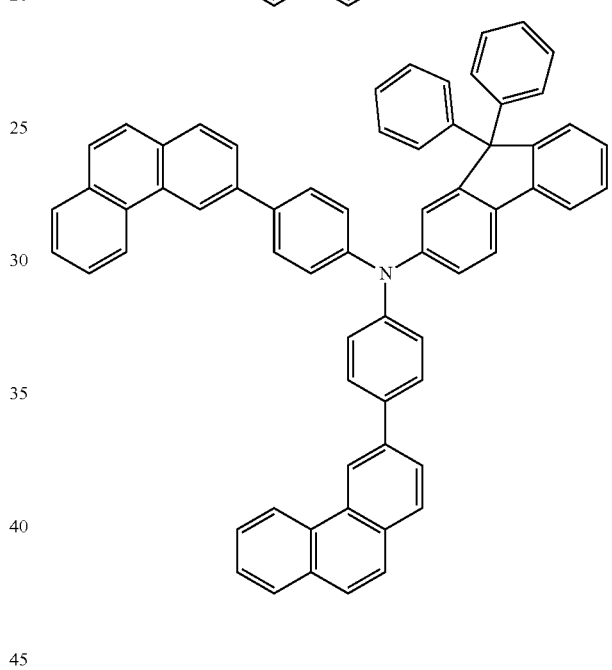
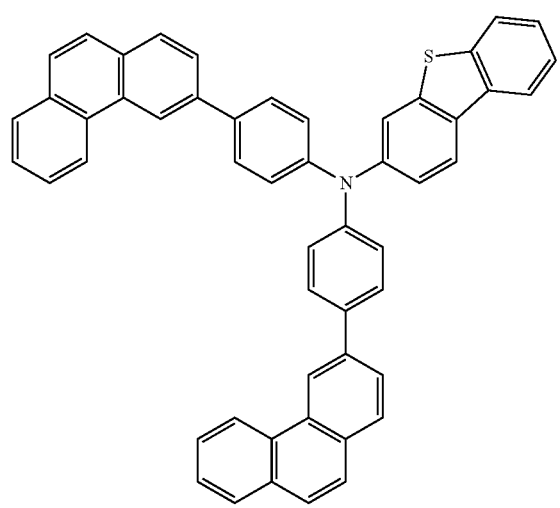
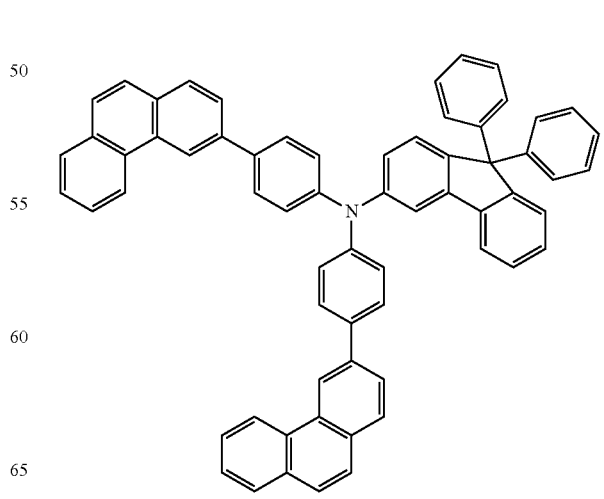

-continued
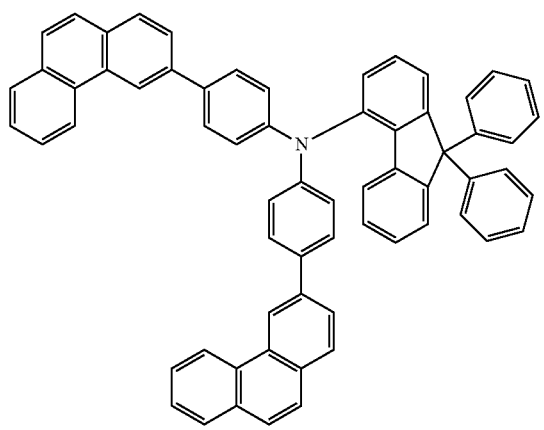
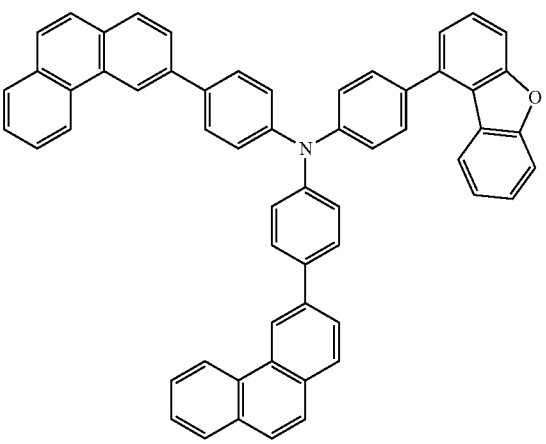
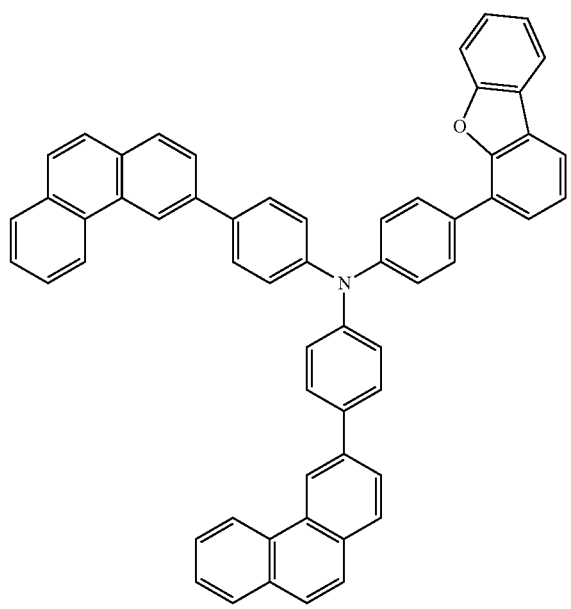
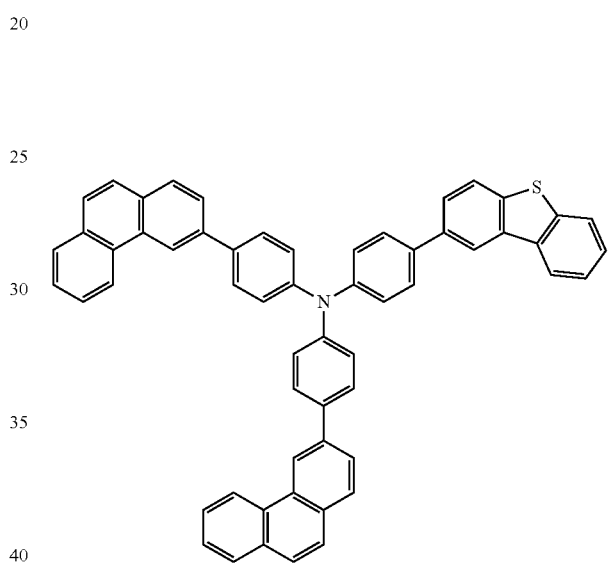
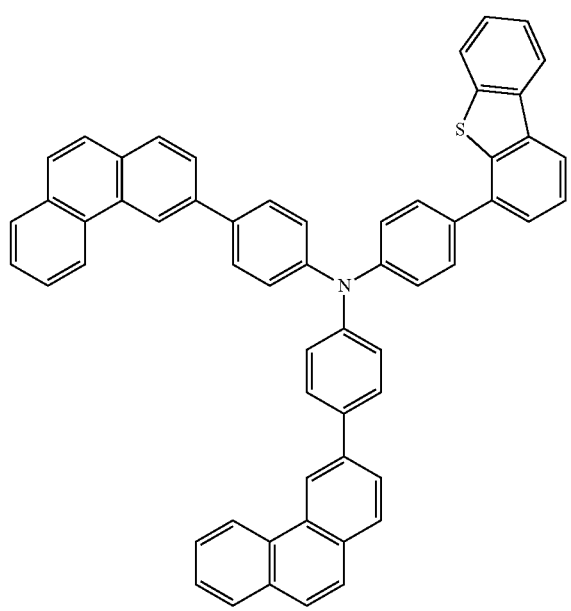
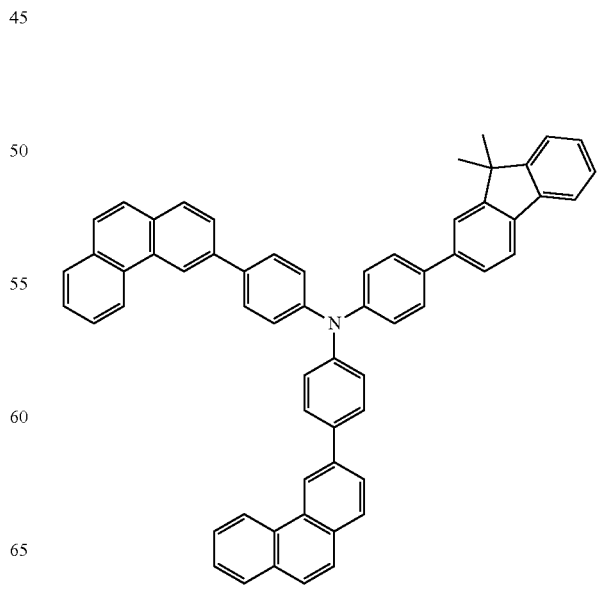

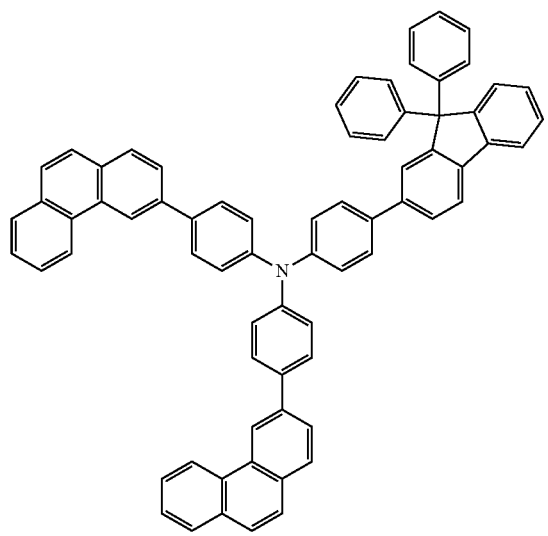
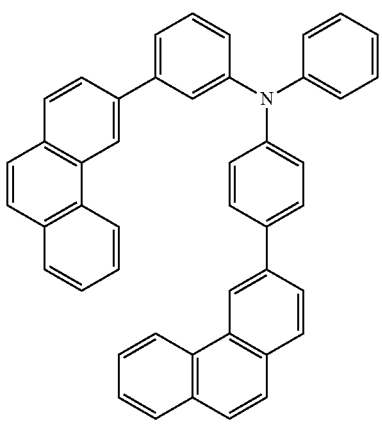
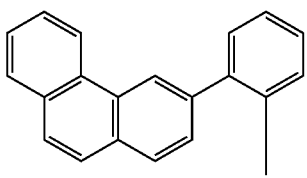
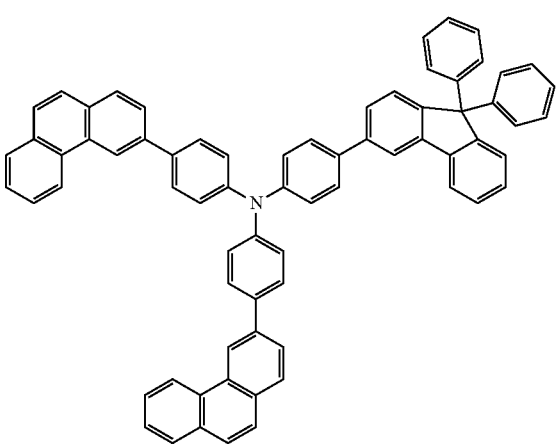
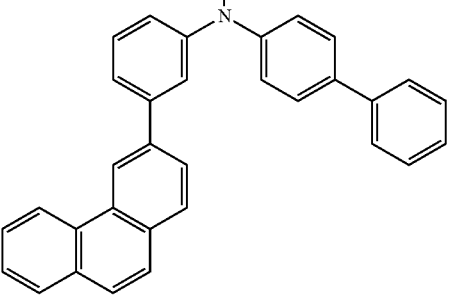
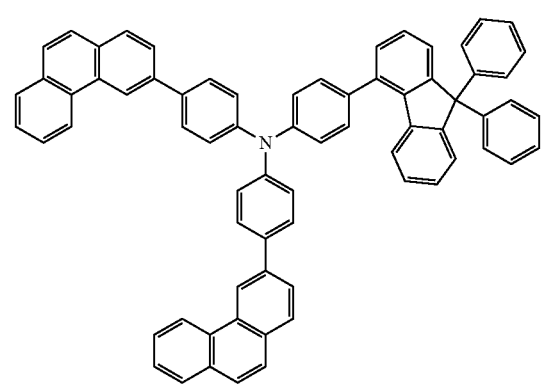
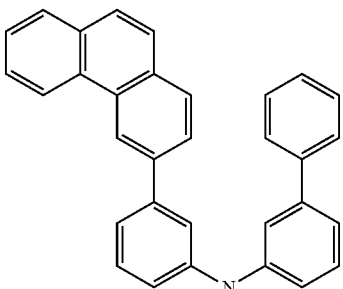

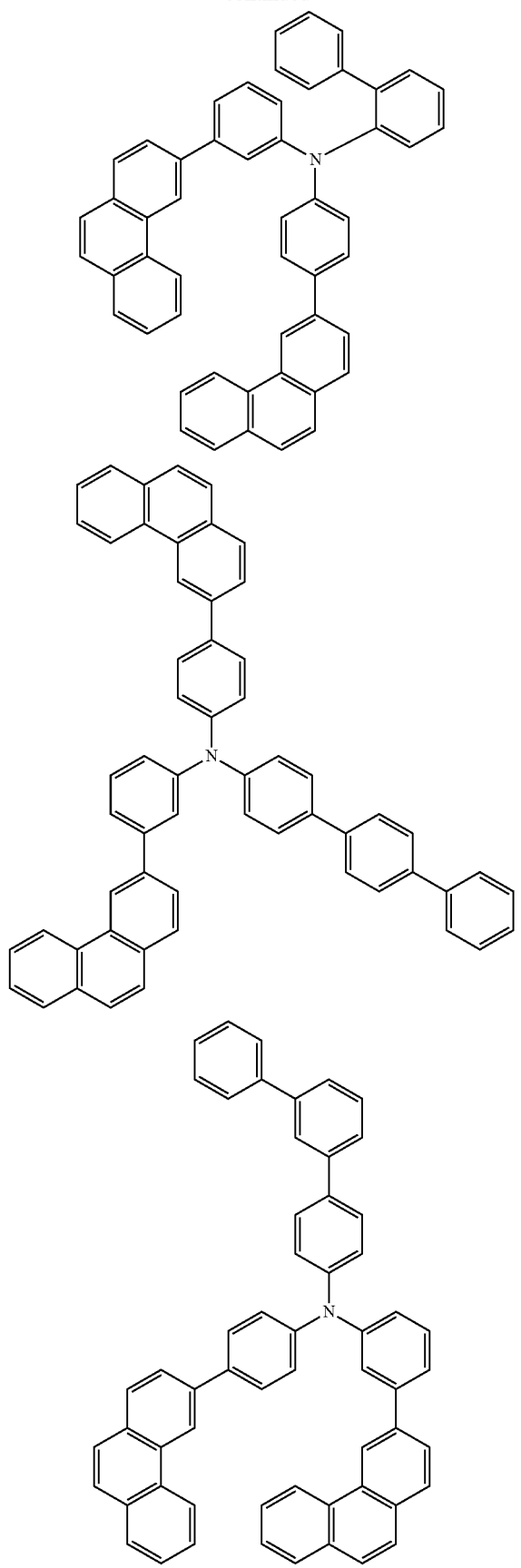
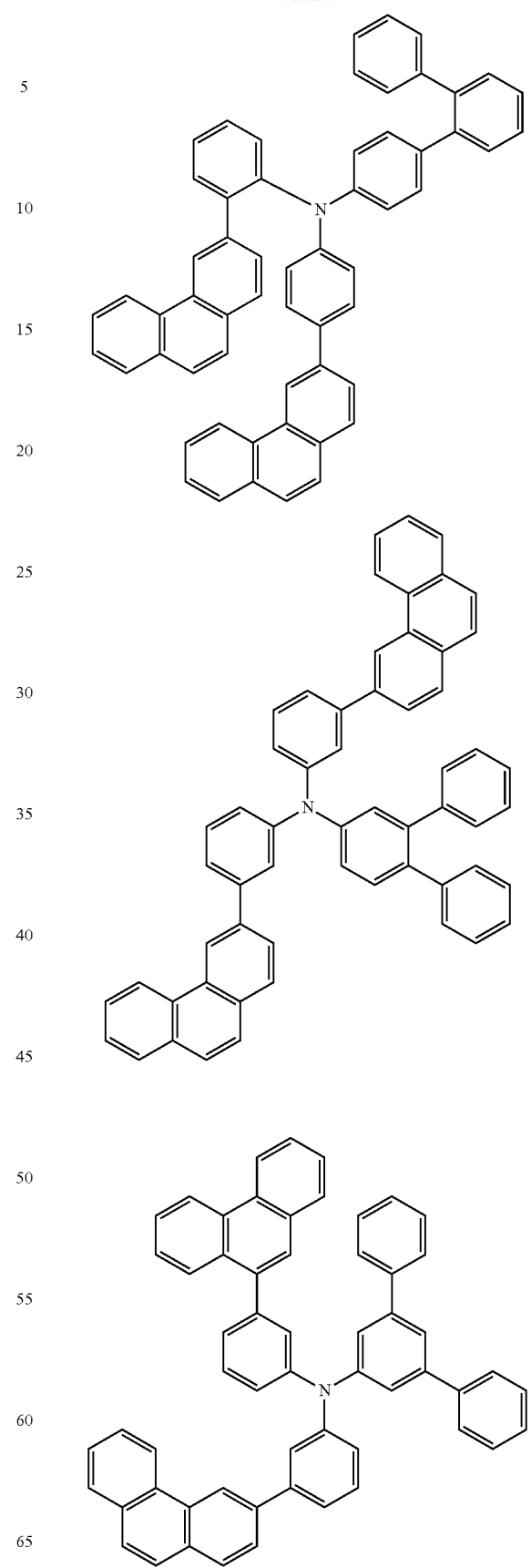

51
-continued
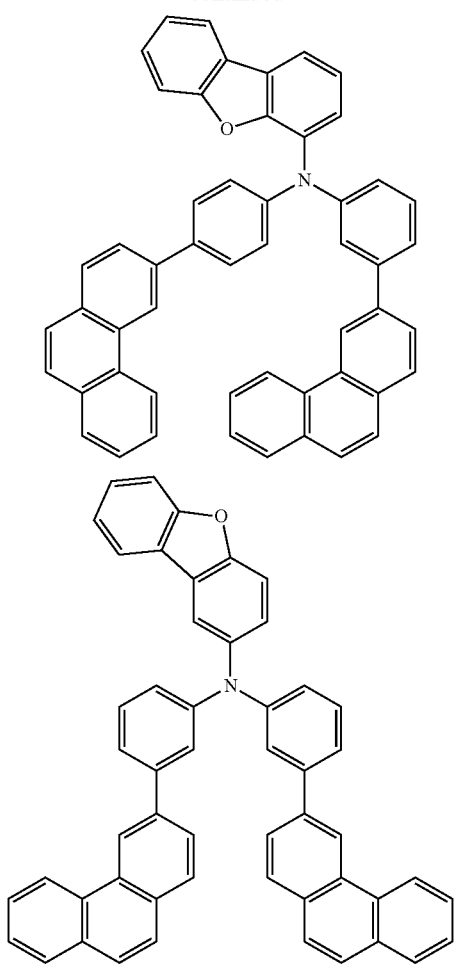
52
-continued
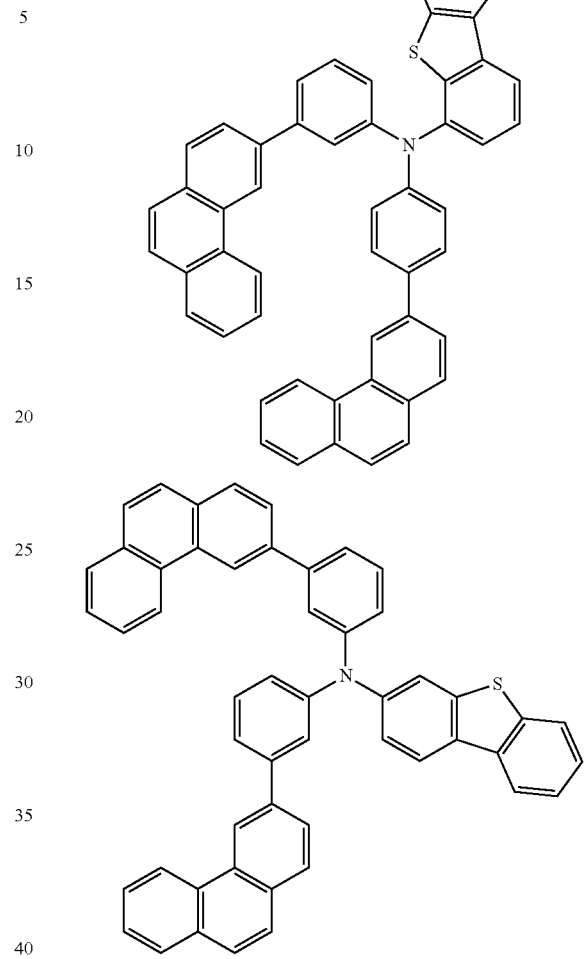
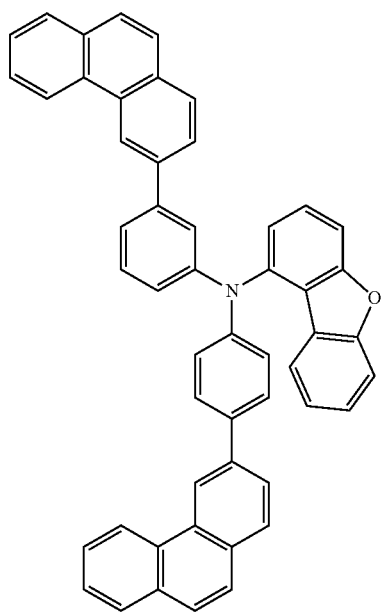
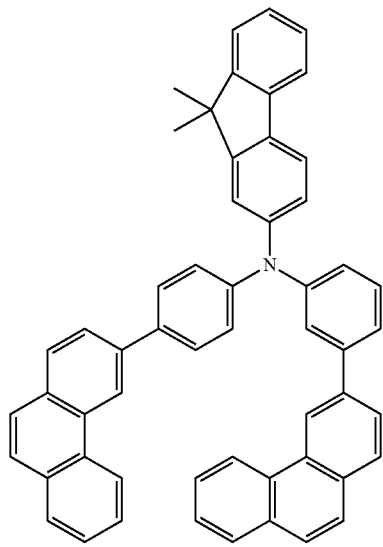

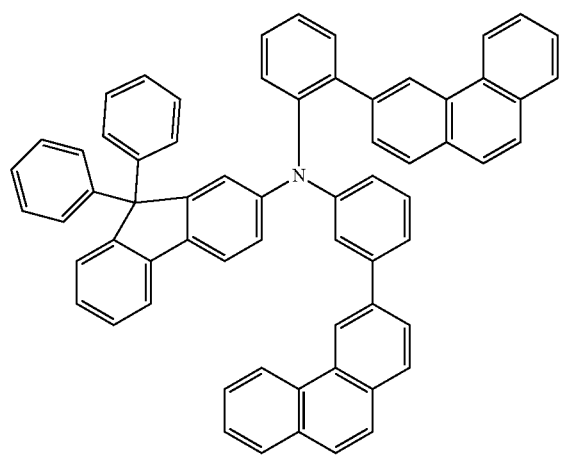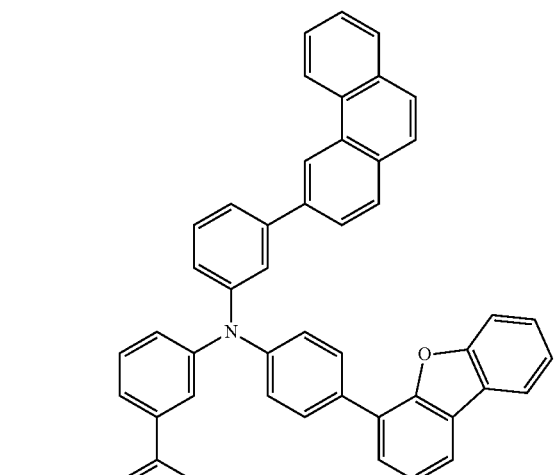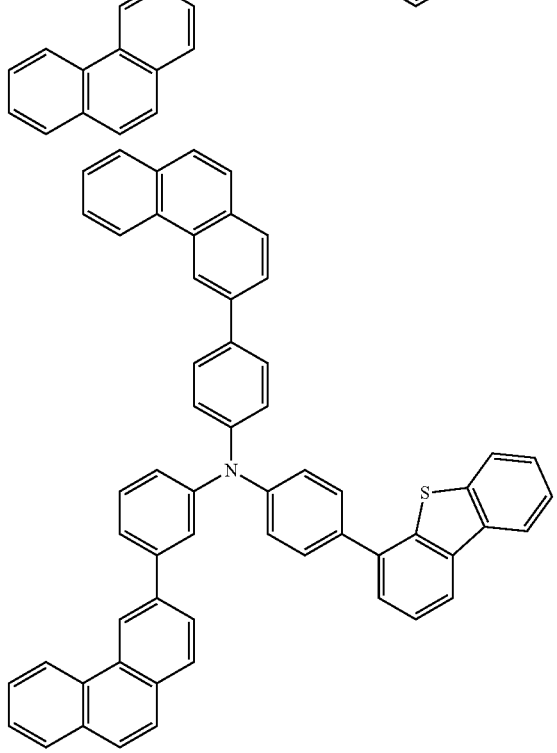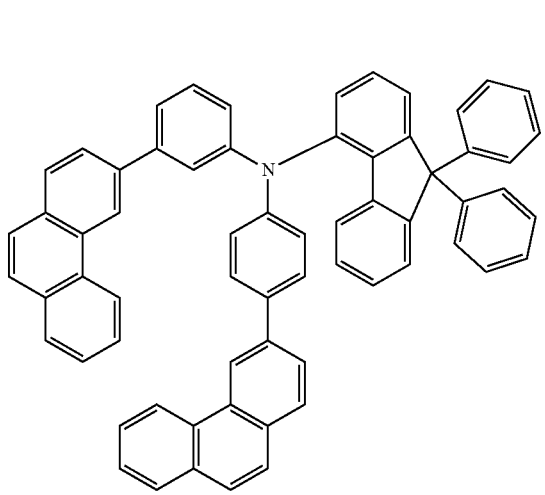

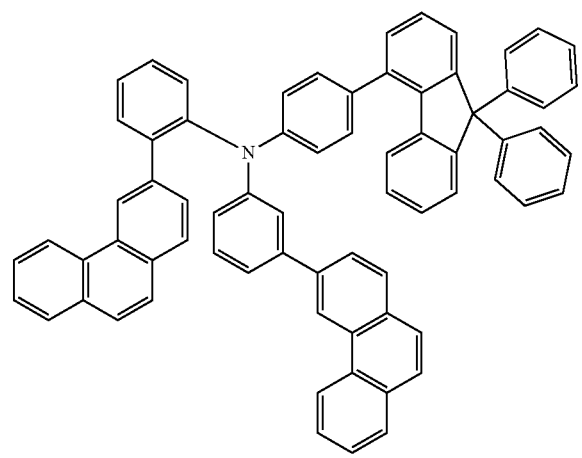
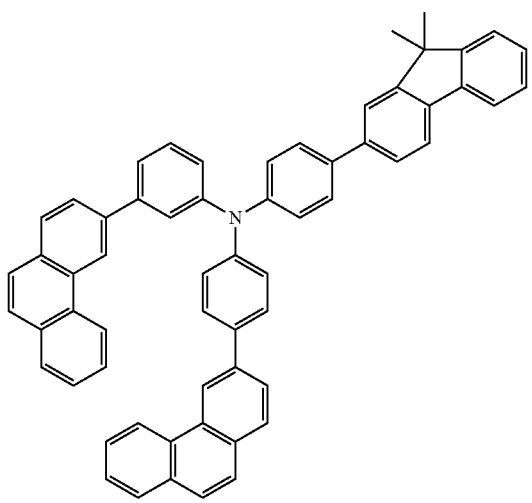
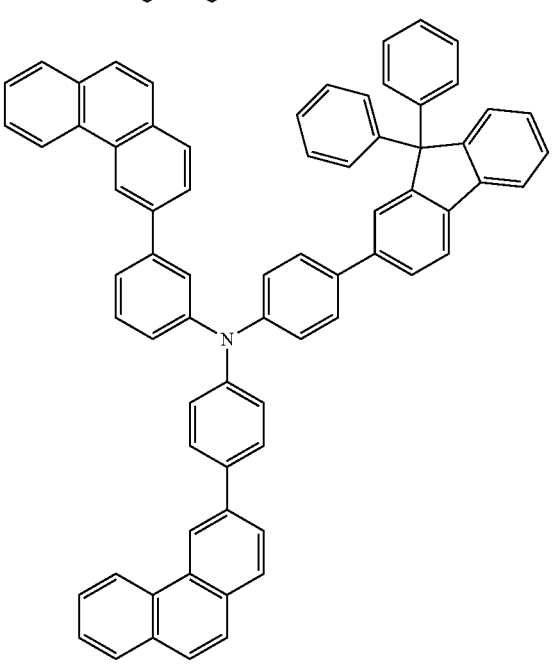
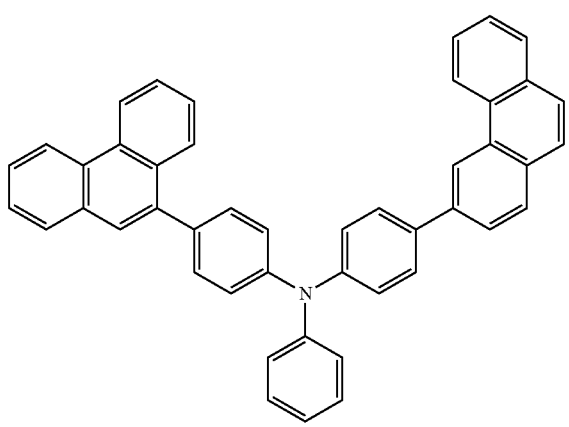

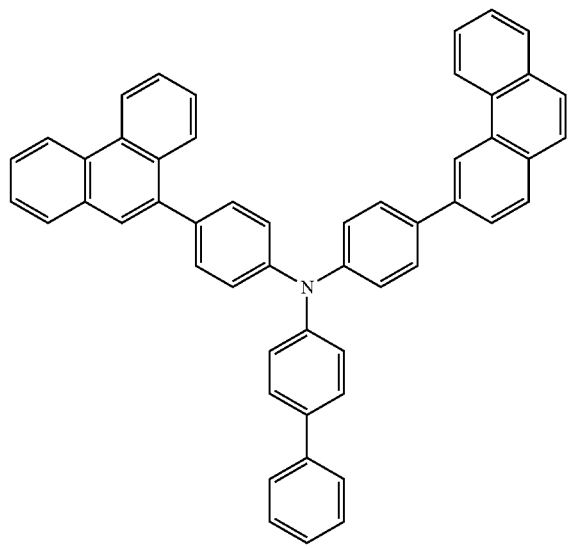
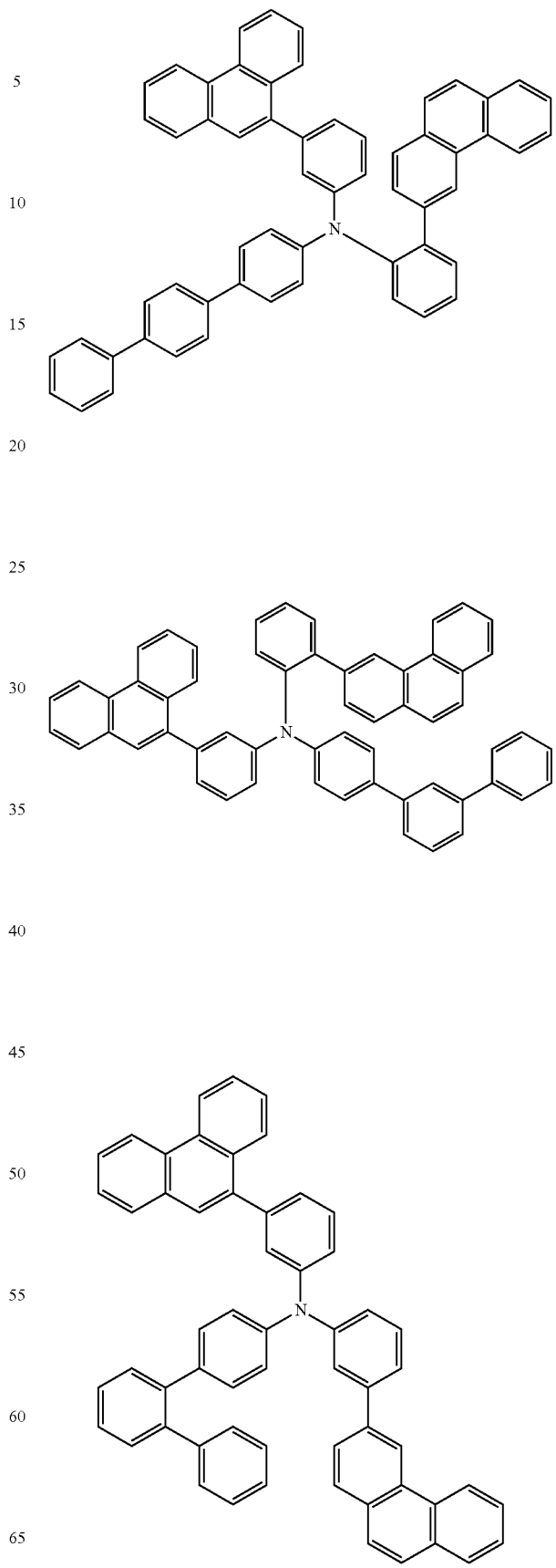

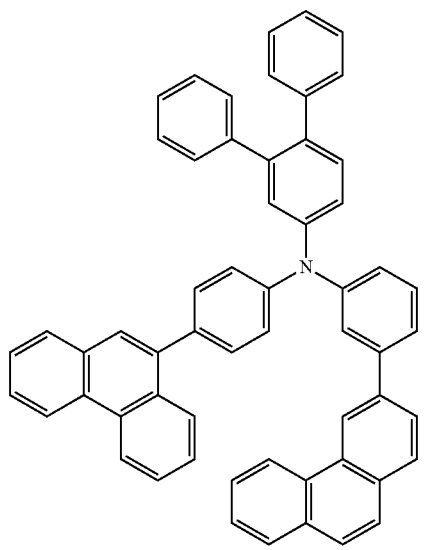
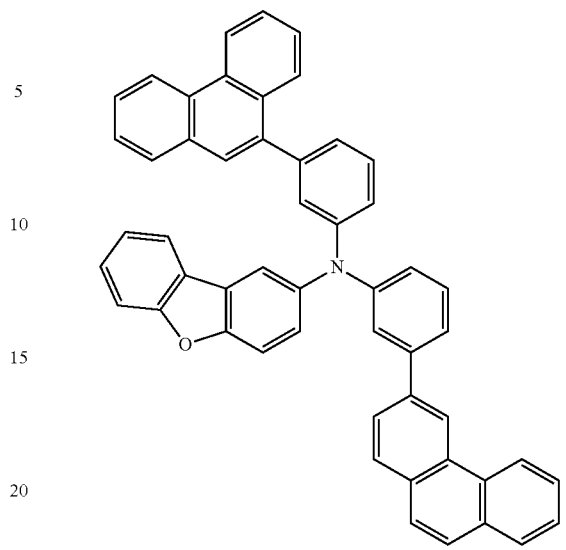
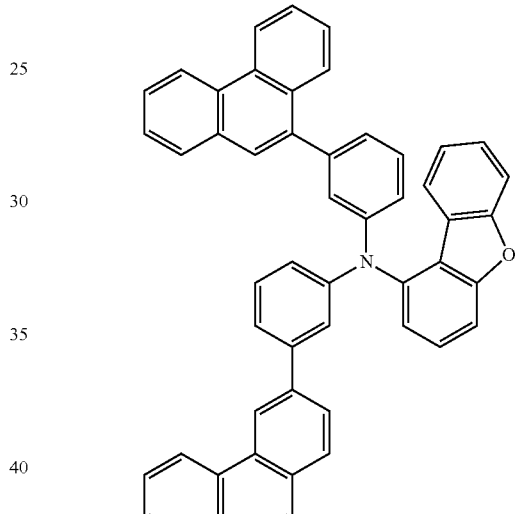
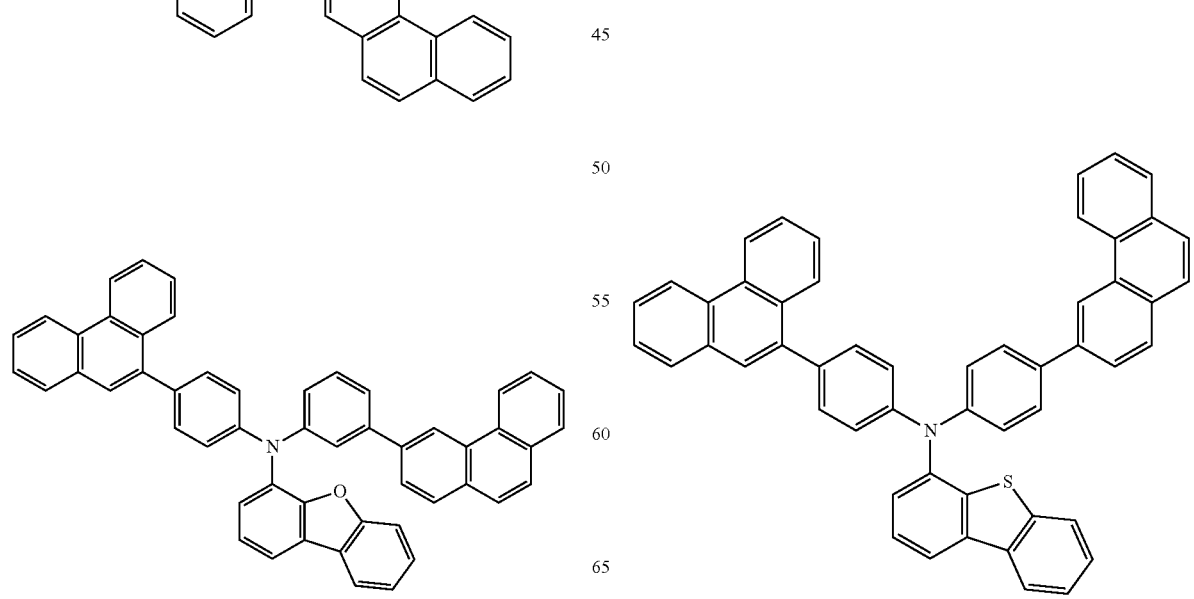

61
-continued
62
-continued
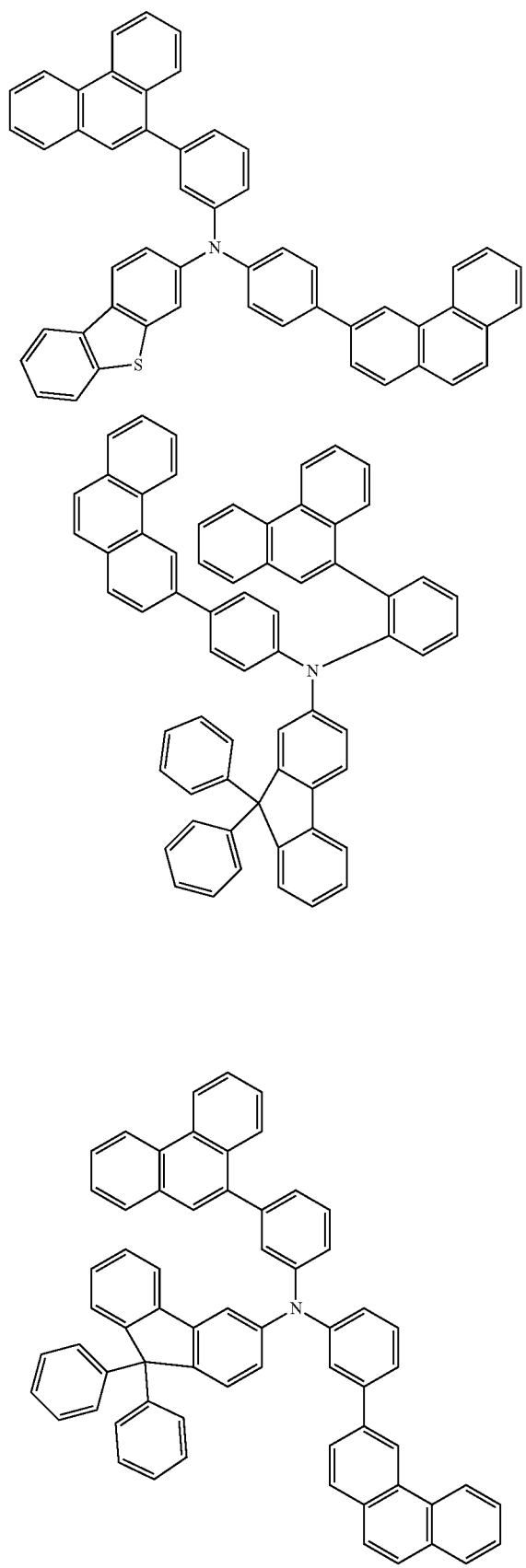
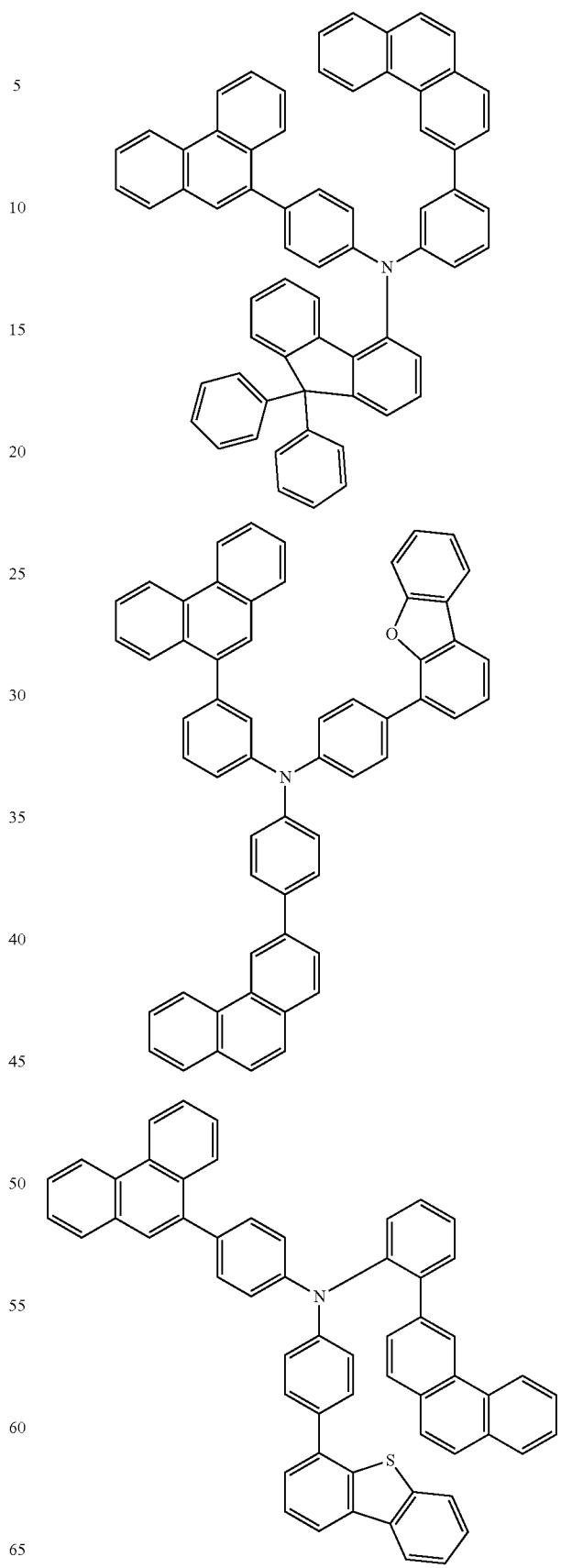

-continued
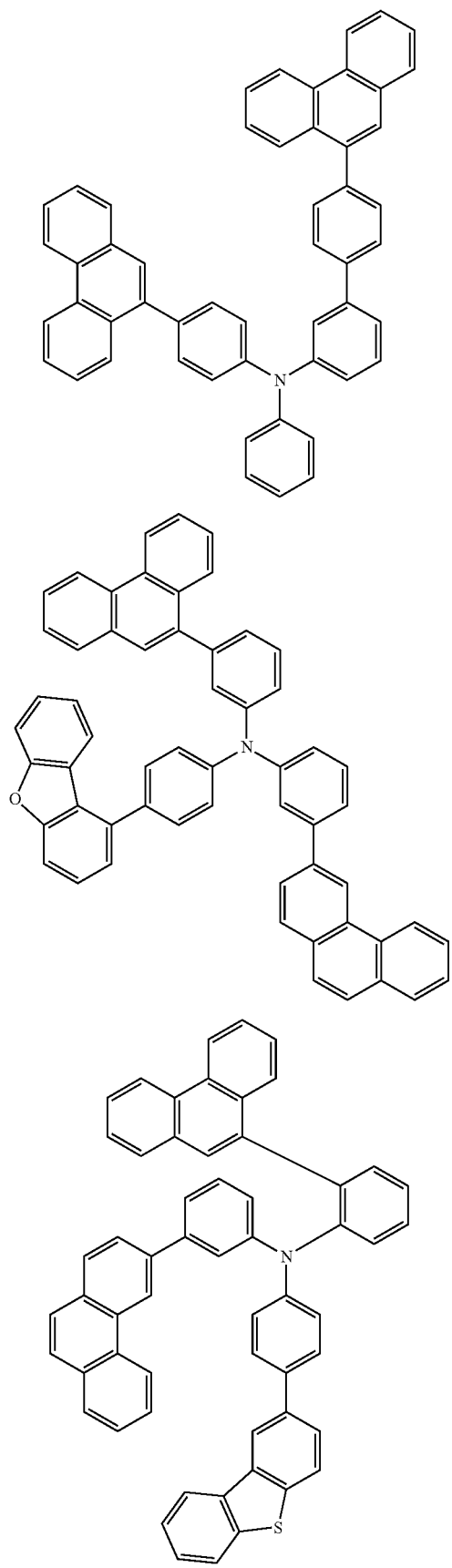
-continued
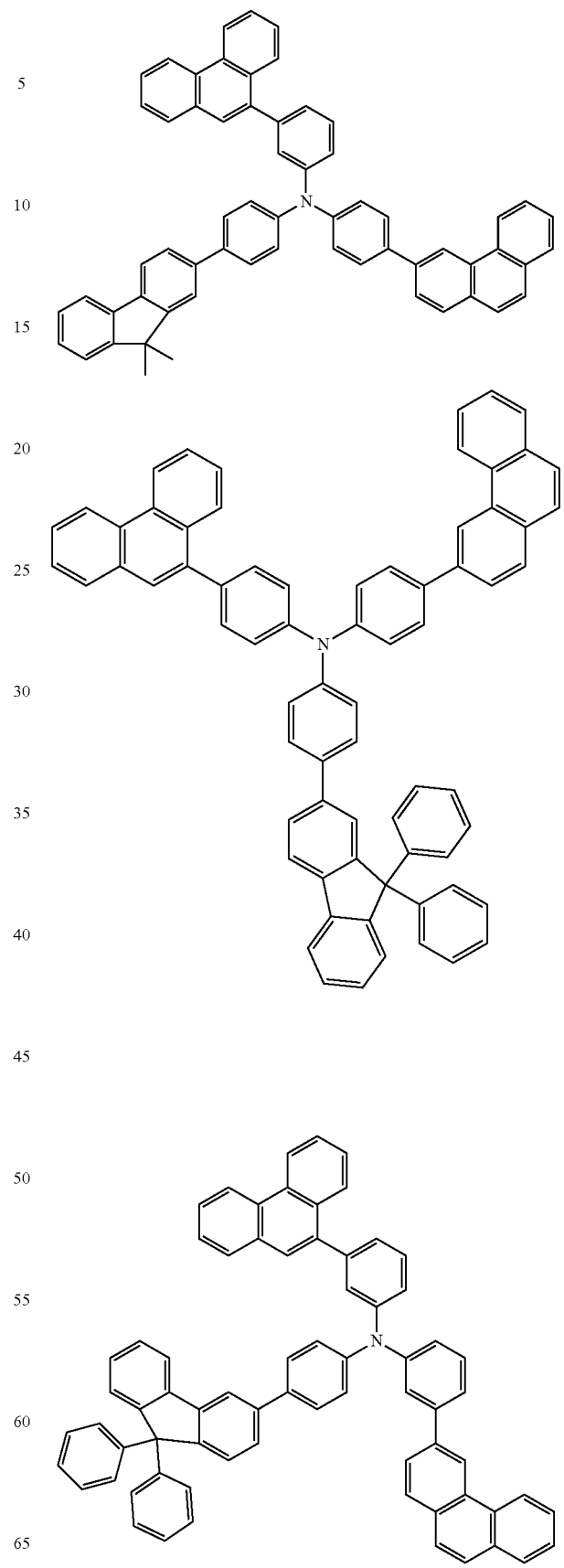

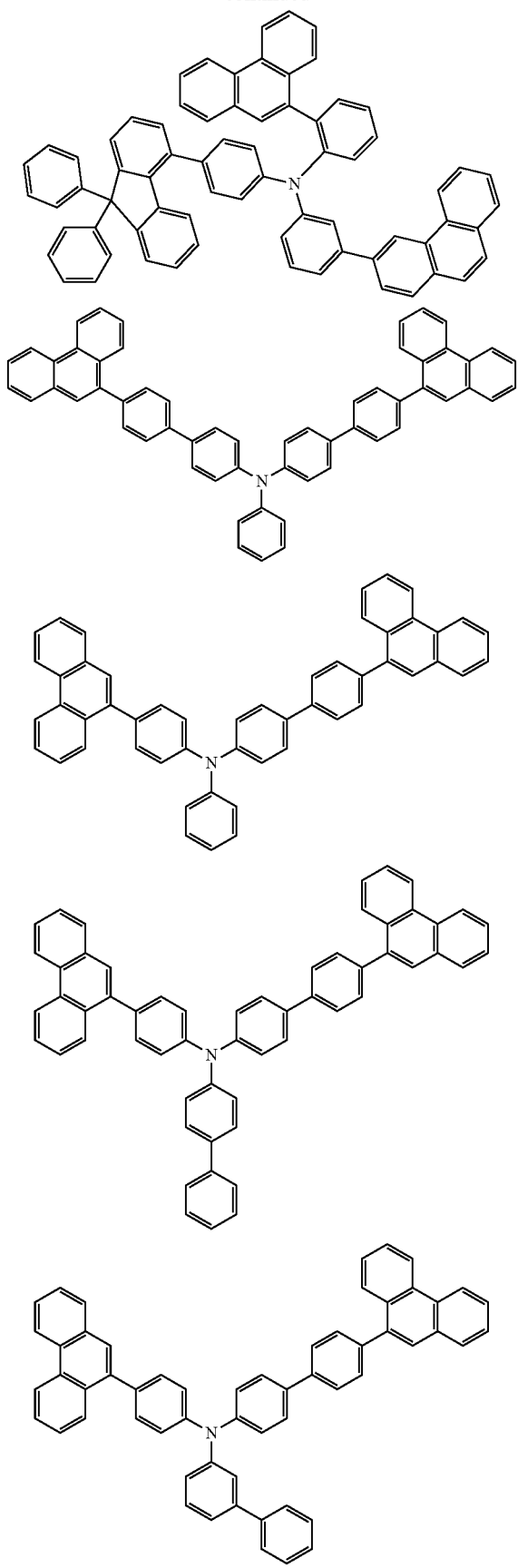
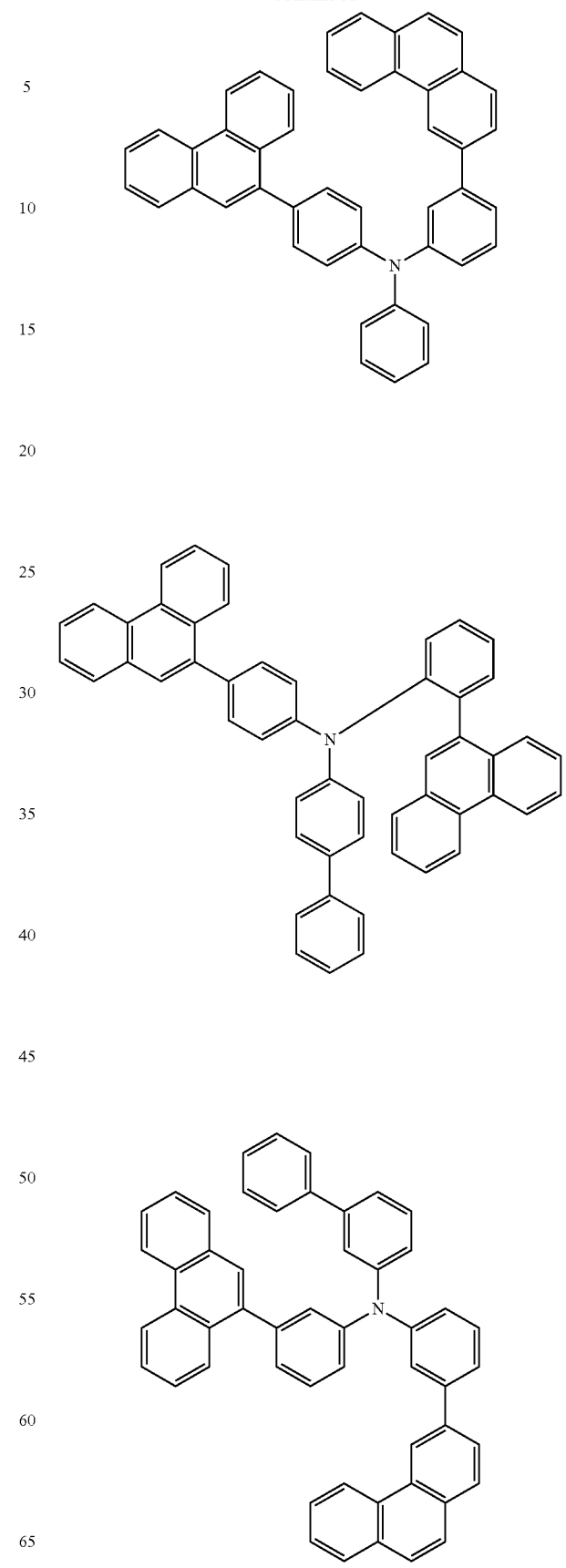

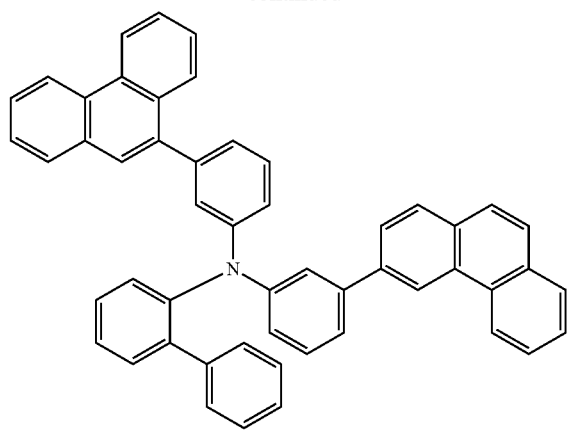
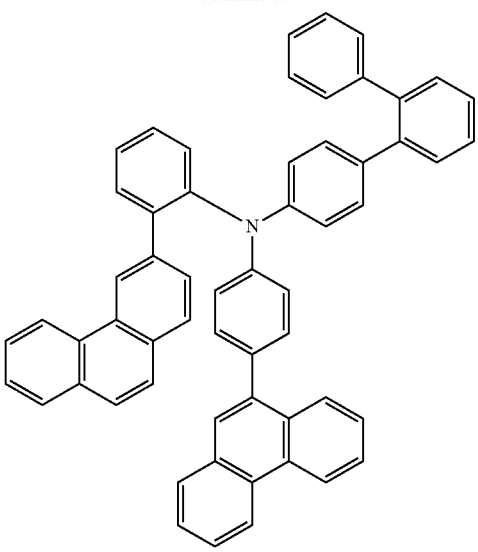
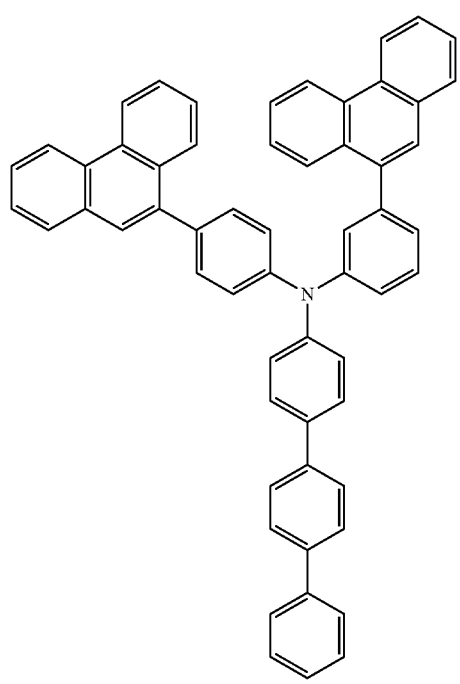
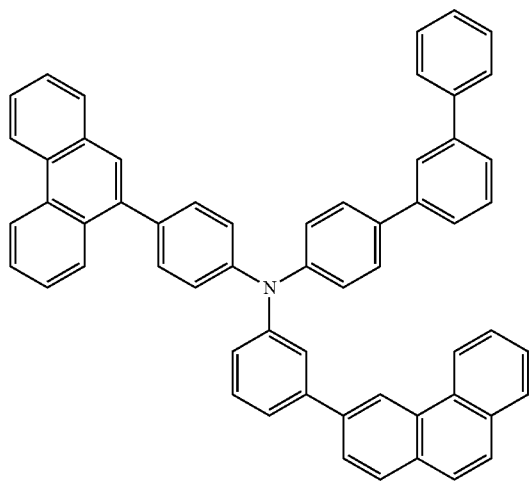
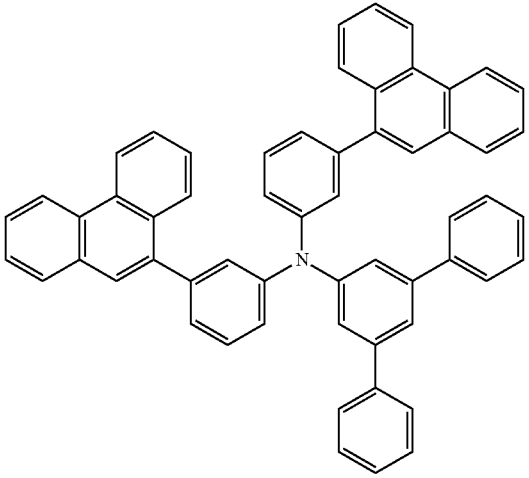

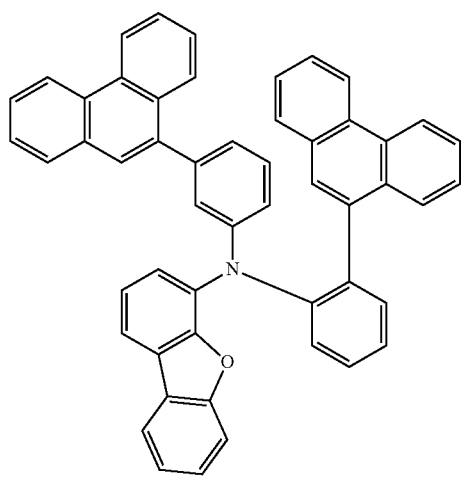
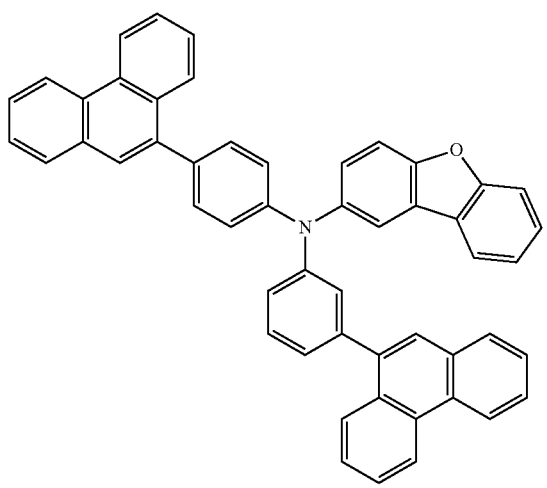
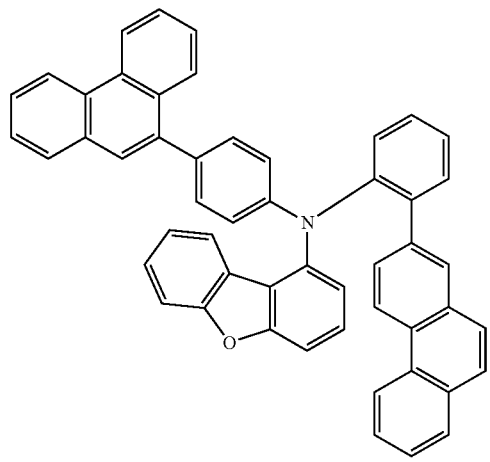
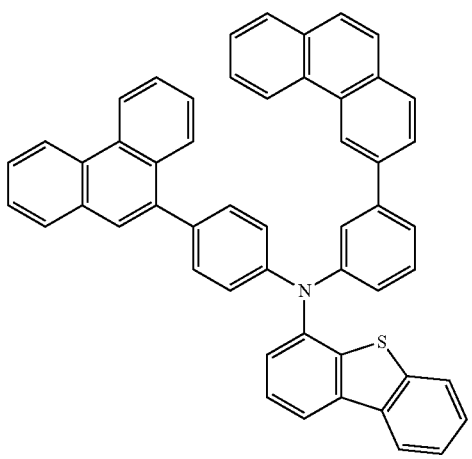
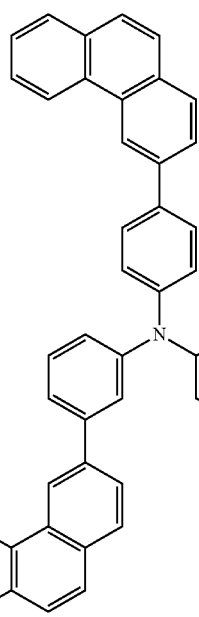
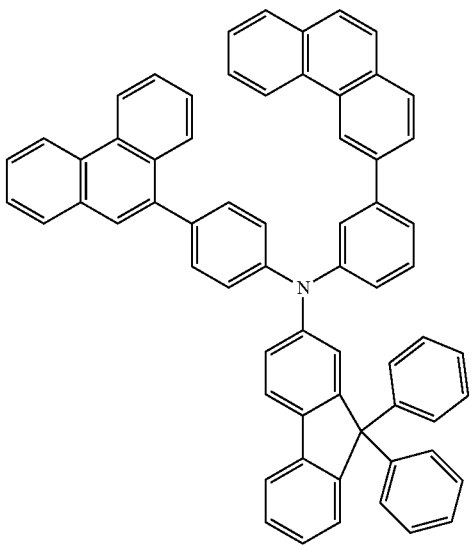

71
-continued

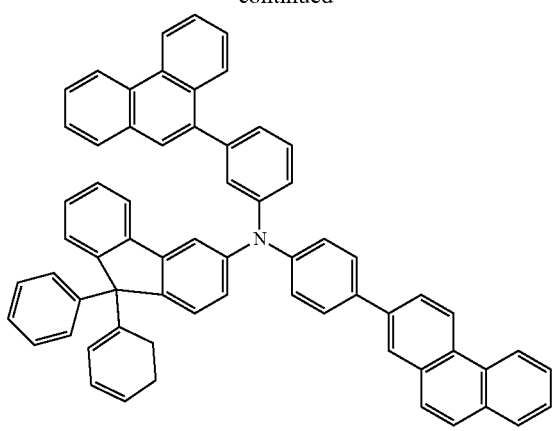

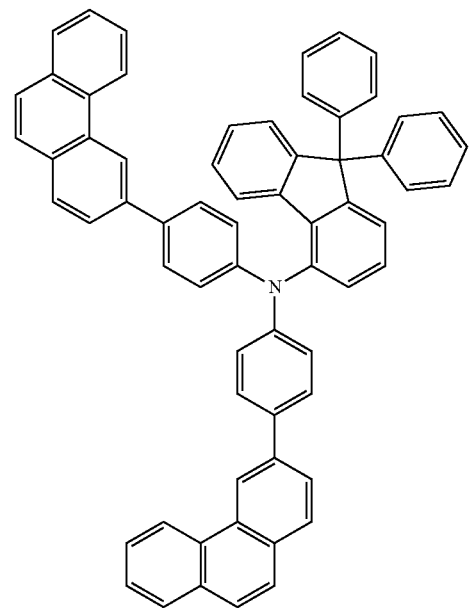

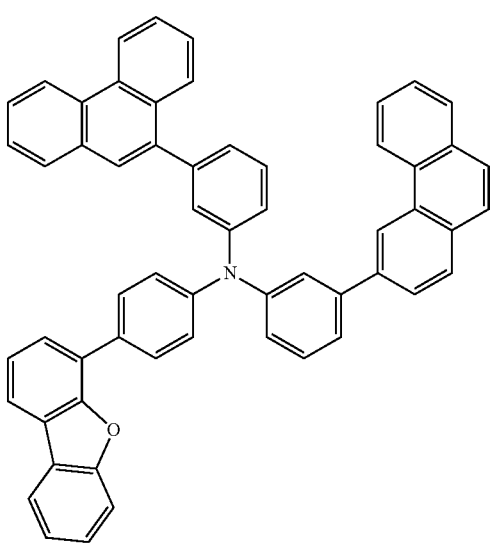

72
-continued

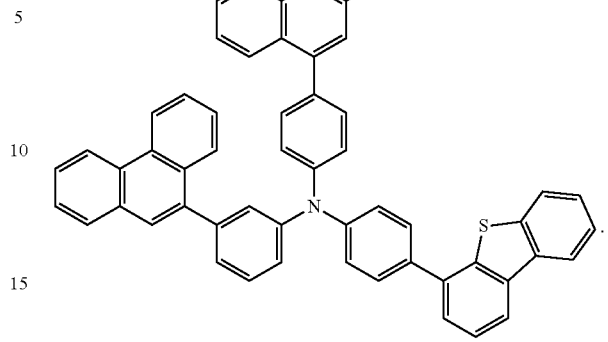

The compound of Chemical Formula 1 can be synthesized through various organic chemistry reactions well known in the art. The method for synthesizing the above compound is further specified in Preparation Examples described hereinafter.

Meanwhile, according to another embodiment of the invention, there is provided an organic electroluminescent device comprising a compound of Chemical Formula 1.

In one example, the present invention provides an organic electroluminescent device comprising a first electrode; a second electrode provided at a side opposite to the first electrode; and at least one layer of organic material layers provided between the first electrode and the second electrode, wherein the at least one layer of the organic material layers includes a compound of Chemical Formula 1.

The organic material layer of the organic electroluminescent device of the present invention can have a single layer structure, but it can have a multilayered structure in which two or more organic material layers are stacked.

For example, the organic electroluminescent device of the present invention can have a structure comprising a hole injection layer, a hole transport layer, a hole adjustment layer, a light emitting layer, an electron transport layer, an electron injection layer and the like as the organic material layer. However, the structure of the organic electroluminescent device is not limited thereto, and it can include a smaller number of organic layers.

Further, the organic material layer can include a hole injection layer, a hole transport layer, and a layer simultaneously performing a hole injection and a hole transport, or a hole adjustment layer, wherein the hole injection layer, the hole transport layer, the layer simultaneously performing a hole injection and a hole transport, or the hole adjustment layer include the compound of Chemical Formula 1.

Further, the organic material layer can include a light emitting layer, wherein the light emitting layer can include a compound of Chemical Formula 1.

Further, the organic material layer can include an electron transport layer or an electron injection layer, wherein the electron transport layer or the electron injection layer includes a compound of Chemical Formula 1.

Further, the electron transport layer, the electron injection layer and the layer simultaneously performing an electron transport and an electron injection include a compound of Chemical Formula 1.

Further, the organic material layer includes a light emitting layer and an electron transport layer, and the electron transport layer can include a compound of Chemical Formula 1.

Further, the organic electroluminescent device according to the present invention can be a normal type organic electroluminescent device in which an anode, at least one organic material layer, and a cathode are sequentially stacked on a substrate.

Further, the organic electroluminescent device according to the present invention can be an inverted type organic electroluminescent device in which a cathode, at least one organic material layer and an anode are sequentially stacked on a substrate.

For example, the structure of an organic electroluminescent device according to an embodiment of the present invention is illustrated in FIGS. 1 and 2.

FIG. 1 shows an example of an organic electroluminescent device comprising a substrate 1, an anode 2, a light emitting layer 3, and a cathode 4. In such a structure, the compound of Chemical Formula 1 can be included in the light emitting layer.

FIG. 2 shows an example of an organic electroluminescent device comprising a substrate 1, an anode 2, a hole injection layer 5, a hole transport layer 6, a light emitting layer 7, an electron transport layer 8, and a cathode 4. In the structure shown in FIG. 2, the compound of Chemical Formula 1 can be included in at least one of the hole injection layer, the hole transport layer, and the electron transport layer; and preferably, in the hole transport layer.

FIG. 3 shows an example of an organic electroluminescent device comprising a substrate 1, an anode 2, a hole injection layer 5, a hole transport layer 6, a hole adjustment layer 9, a light emitting layer 7, an electron transport layer 8, and a cathode 4. In the structure shown in FIG. 3, the compound of Chemical Formula 1 can be included in hole injection layer, or the hole transport layer.

Meanwhile, the organic electroluminescent device according to the present invention can be manufactured by materials and methods known in the art, except that at least one layer of the organic material layers includes the compound of Chemical Formula 1.

In addition, when the organic electroluminescent device includes a plurality of organic material layers, the organic material layers can be formed of the same material or different materials.

For example, the organic electroluminescent device according to the present invention can be manufactured by sequentially stacking a first electrode, an organic material layer and a second electrode on a substrate.

In this case, the organic electroluminescent device can be manufactured by depositing a metal, metal oxides having conductivity, or an alloy thereof on the substrate using a PVD (physical vapor deposition) method such as a sputtering method or an e-beam evaporation method to form an anode, forming an organic material layer including the hole injection layer, the hole transport layer, the light emitting layer, and the electron transport layer thereon, and then depositing a material that can be used as the cathode thereon.

In addition to such a method, the organic electroluminescent device can be manufactured by sequentially depositing a cathode material, an organic material layer and an anode material on a substrate.

In addition, the compound of Chemical Formula 1 can be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic electroluminescent device can be manufactured by sequentially depositing a cathode material, an organic material layer, and an anode material on a substrate (International Publication WO 2003/012890).

As one example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has an ability of transporting the holes, thus a hole injecting effect in the anode and an excellent hole injecting effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is a material capable of emitting light in the visible light region by combining holes and electrons respectively transported from the hole transport layer and the electron transport layer, and having good quantum efficiency for fluorescence or phosphorescence. Specific examples of the light emitting material include 8-hydroxy-quinoline aluminum complex (Alga); carbazole-based compounds; dimerized styryl compounds; BAlq; 10-hydroxybenzoquinoline-metal compounds; benzoxazole, benzthiazole and benzimidazole-based compounds; poly(p- phenylenevinylene)(PPV)-based polymers; Spiro compounds; polyfluorene, rubrene, and the like, but are not limited thereto.

The light emitting layer can include a host material and a dopant material. The host material can be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds and the like. Examples of heterocyclic compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specific examples of the aromatic amine derivatives include substituted or unsubstituted fused aromatic ring derivatives having an arylamino group, examples thereof include pyrene, anthracene, chrysene, and periflanthene having the arylamino group, and the like, the styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer receiving the electrons from the electron injection layer and transporting the electrons to the light emitting layer, the electron transport material is a material that can receive the electrons well from the cathode and transport the electrons to the light emitting layer, and a material having large mobility to the electrons is suitable. Specific examples thereof include an 8-hydroxyquinoline Al complex; a complex including Alga; an organic radical compound; a hydroxyflavone-metal complex, and the like, but are not limited thereto. The electron transport layer can be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injecting effect from the cathode, and an excellent electron injecting effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and its derivative, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxy-benzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)-(2-naphtholato)gallium, and the like, but are not limited thereto.

The organic electroluminescent device according to the present invention can be a front side emission type, a back side emission type, or a double side emission type according to the used material.

In addition, the compound of Chemical Formula 1 can be included in an organic solar cell or an organic transistor in addition to an organic electroluminescent device.

Hereinafter, preferred examples are provided for better understanding of the invention. However, these Examples are given for illustrative purposes only and are not intended to limit the scope of the present invention thereto.

Synthesis Example 1

(Synthesis of Compound A1)

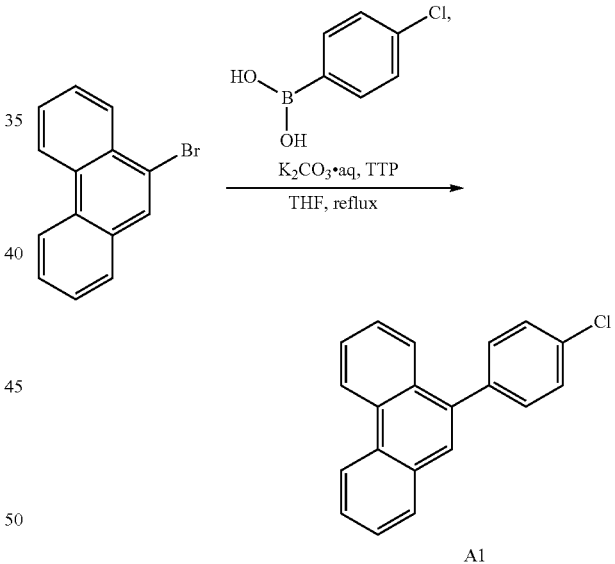

9-Bromophenanthrene (25 g, 68.83 mmol) and 4-chlorophenylboronic acid (11.30 g, 72.27 mmol) were added to tetrahydrofuran (300 ml), to which a 2M aqueous potassium carbonate solution (150 ml) was added and tetrakistriphenylphosphinopalladium (1.59 g, 2 mol %) was added, and the mixture was heated and stirred for 10 hours. The reaction temperature was then lowered to room temperature. After completion of the reaction, the aqueous potassium carbonate solution was removed and the layers were separated. After removal of the solvent, a white solid was recrystallized from acetate to obtain Compound A1 (9-(4-chlorophenyl)phenanthrene, 23.1 g, yield 85%).

MS[M+H]$^+$=289.77

Synthesis Example 2

(Synthesis of Compound A2)

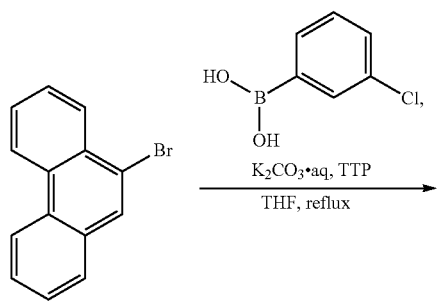

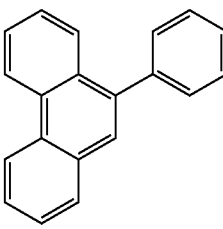

A2

Compound A2 (9-(3-chlorophenyl)phenanthrene) was obtained in the same manner as in Synthesis Example 1, except that 3-chlorophenylboronic acid was used instead of 4-chlorophenylboronic acid.

MS[M+H]$^+$=289.77

Synthesis Example 3

(Synthesis of Compound A3)

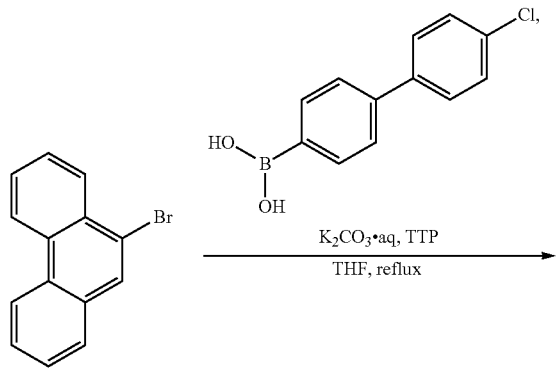

A3

Compound A3 (9-(4'-chloro-[1,1'-biphenyl]-4-yl)phenanthrene) was obtained in the same manner as in Synthesis Example 1, except that (4'-chloro-[1,1-biphenyl]-4-yl)boronic acid was used instead of 4-chlorophenylboronic acid.

MS[M+H]$^+$=345.87

Synthesis Example 4

(Synthesis of Compound B1)

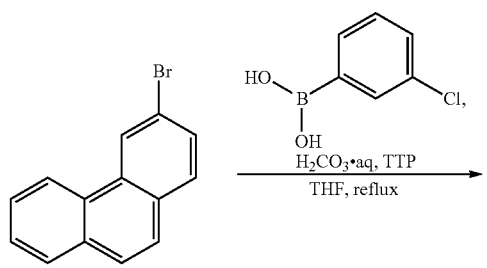

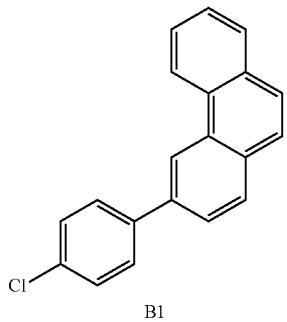

B1

Compound B1 (3-(4-chlorophenyl)phenanthrene) was obtained in the same manner as in Synthesis Example 1, except that 3-bromophenanthrene was used instead of 9-bromophenanthrene.

MS[M+H]$^+$=289.77

Synthesis Example 5

(Synthesis of Compound B2)

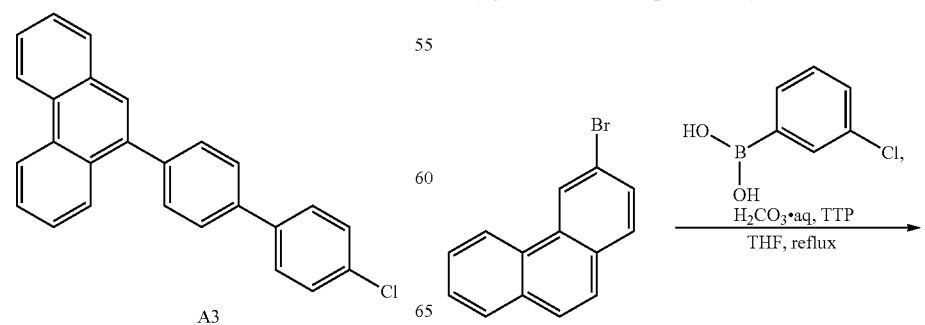

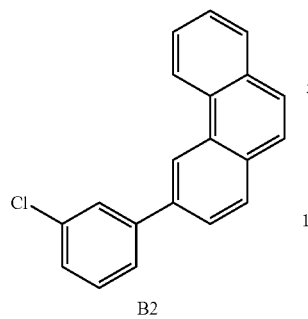

B2

Compound B2 (3-(3-chlorophenyl)phenanthrene) was obtained in the same manner as in Synthesis Example 4, except that 3-chlorophenylboronic acid was used instead of 4-chlorophenylboronic acid.

MS[M+H]$^+$=289.77

Synthesis Example 6

(Synthesis of Compound 1)

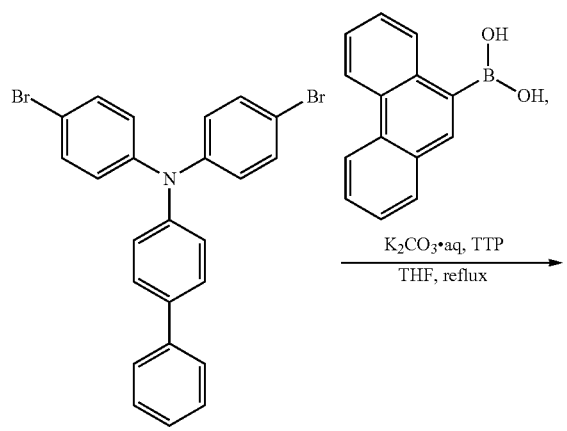

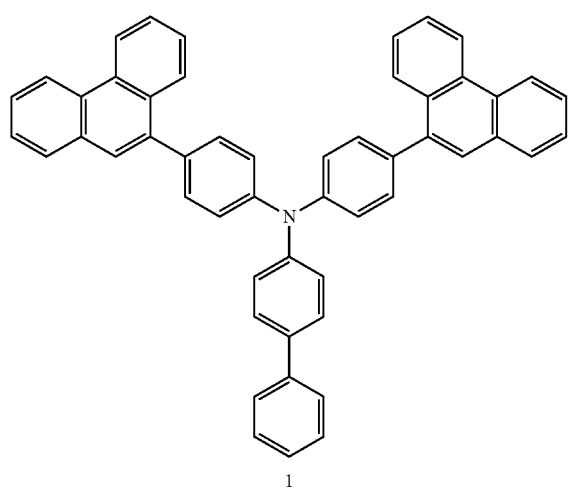

1

The compound B1 (25 g, 68.83 mmol) and 4-chlorophenylboronic acid (11.30 g, 72.27 mmol) were added to tetrahydrofuran (300 ml), to which a 2M aqueous potassium carbonate solution (150 ml) was added and tetrakistriphenylphosphinopalladium (1.59 g, 2 mol %) was added, and the mixture was heated and stirred for 10 hours. The reaction temperature was then lowered to room temperature. After completion of the reaction, the aqueous potassium carbonate solution was removed and the layers were separated. After removal of the solvent, a white solid was recrystallized from acetate to obtain Compound 1 (N,N-bis(4-(phenanthren-9-yl)phenyl)-[1,1'-biphenyl]-4-amine, 23.1 g, yield 85%).

MS[M+H]$^+$=674.28

Synthesis Example 7

(Synthesis of Compound 2)

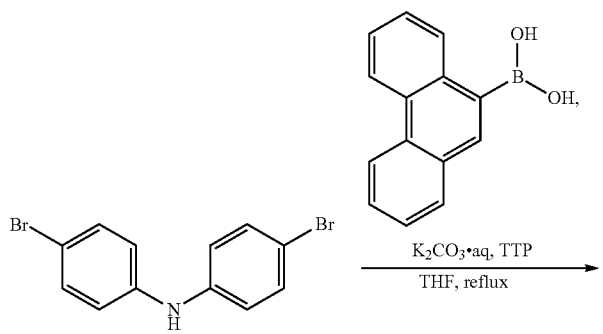

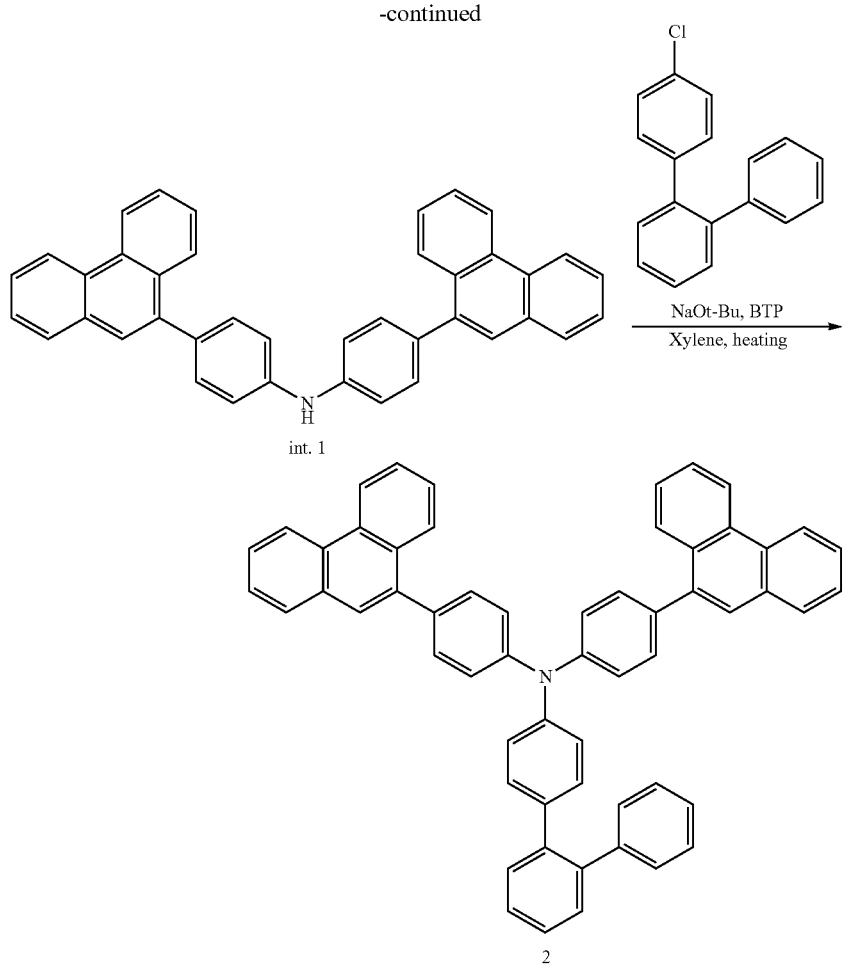

(1) The compound int. 1 (bis(4-(phenanthren-9-yl)phenyl) amine) was obtained in the same manner as in Synthesis Example 1, except that bis(4-bromophenyl)amine was used instead of bromophenanthrene, and phenanthrene-9-boronic acid was used instead of 4-chlorophenylboronic acid.

MS[M+H]$^+$=522.66

(2) The compound int. 1 (15 g, 29.9 mmol), 4-chloro-1,1'; 2',1''-terphenyl (9.81 g, 30.5 mmol), and sodium-t-butoxide (4.03 g, 41.8 mol) were added to xylene, and the mixture was heated, stirred and then refluxed. [Bis(tri-t-butylphosphine)]palladium (170 mg, 1 mol %) was then added thereto, and the reaction temperature was lowered to room temperature. After completion of the reaction, recrystallization from tetrahydrofuran and ethyl acetate gave Compound 2 (N,N-bis(4-(phenanthren-9-yl)phenyl)-[1,1':2',1''-terphenyl]-4-amine, 16.4 g, 74%)

MS[M+H]$^+$=750.96

Synthesis Example 8

(Synthesis of Compound 3)

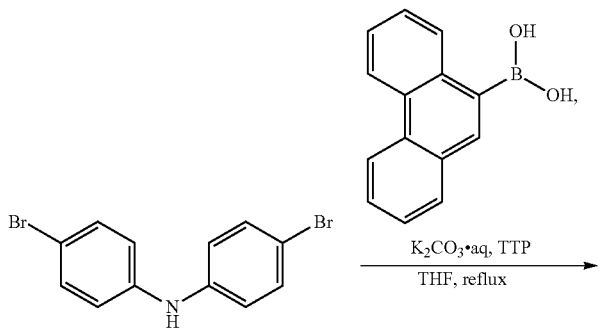

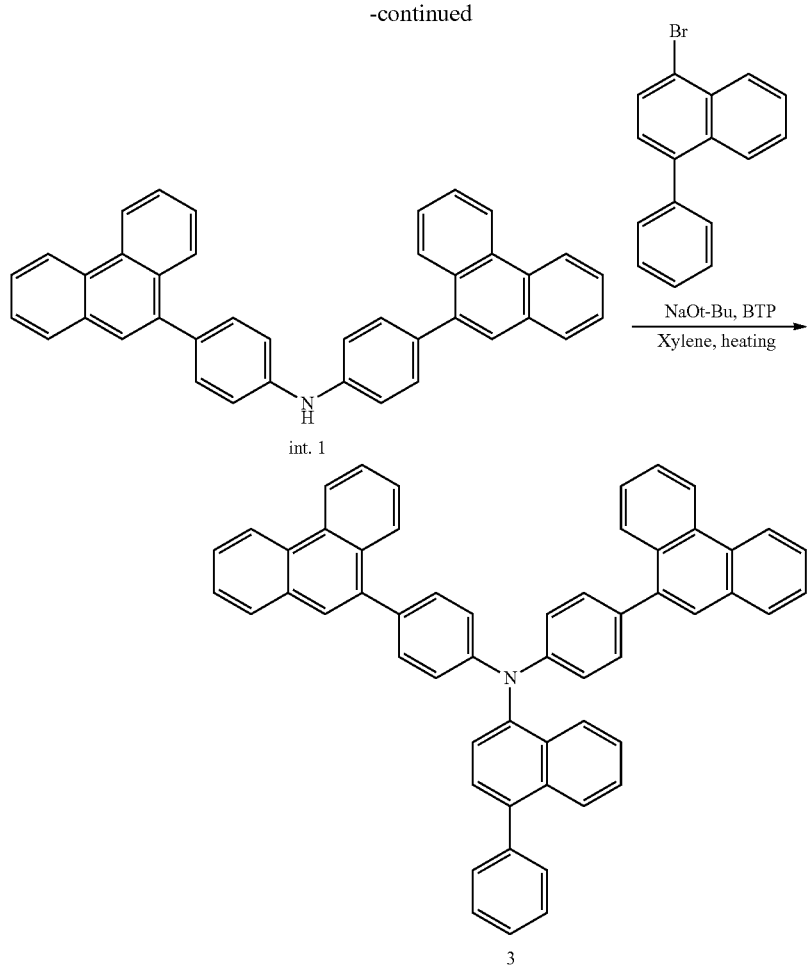

The compound (N,N-bis(4-(phenanthren-9-yl)phenyl)-4-phenylnaphthalen-1-amine) was obtained in the same manner as in Synthesis Example 7, except that 1-bromo-4-phenylnaphthalene was used instead of 4-chloro-1,1'; 2',1''-terphenyl.

MS[M+H]$^+$=724.92

Synthesis Example 9

(Synthesis of Compound 4)

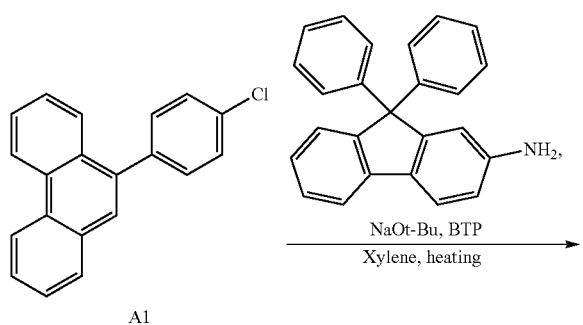

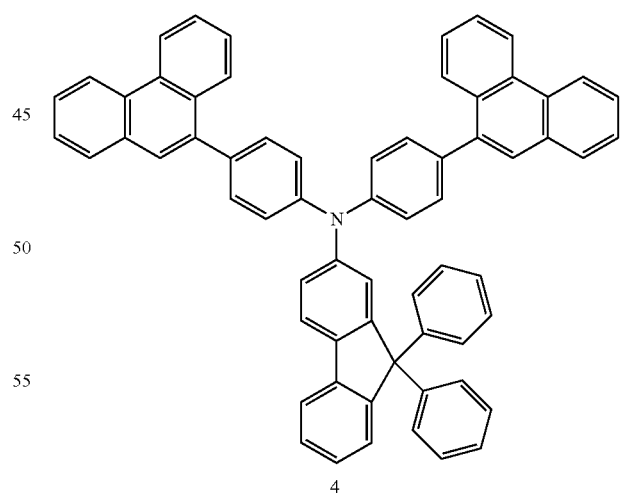

The compound 4 (N,N-bis(4-(phenanthren-9-yl)phenyl)-9,9-diphenyl-9H-fluoren-2-amine) was obtained in the same manner as in Synthesis Example 7, except that 9,9-diphenyl-9H-fluoren-2-amine was used instead of the compound int. 1, and the compound A1 was used instead of 4-chloro-1,1'; 2',1''-terphenyl.

MS[M+H]$^+$=839.07

Synthesis Example 10

(Synthesis of Compound 5)

Synthesis Example 11

(Synthesis of Compound 6)

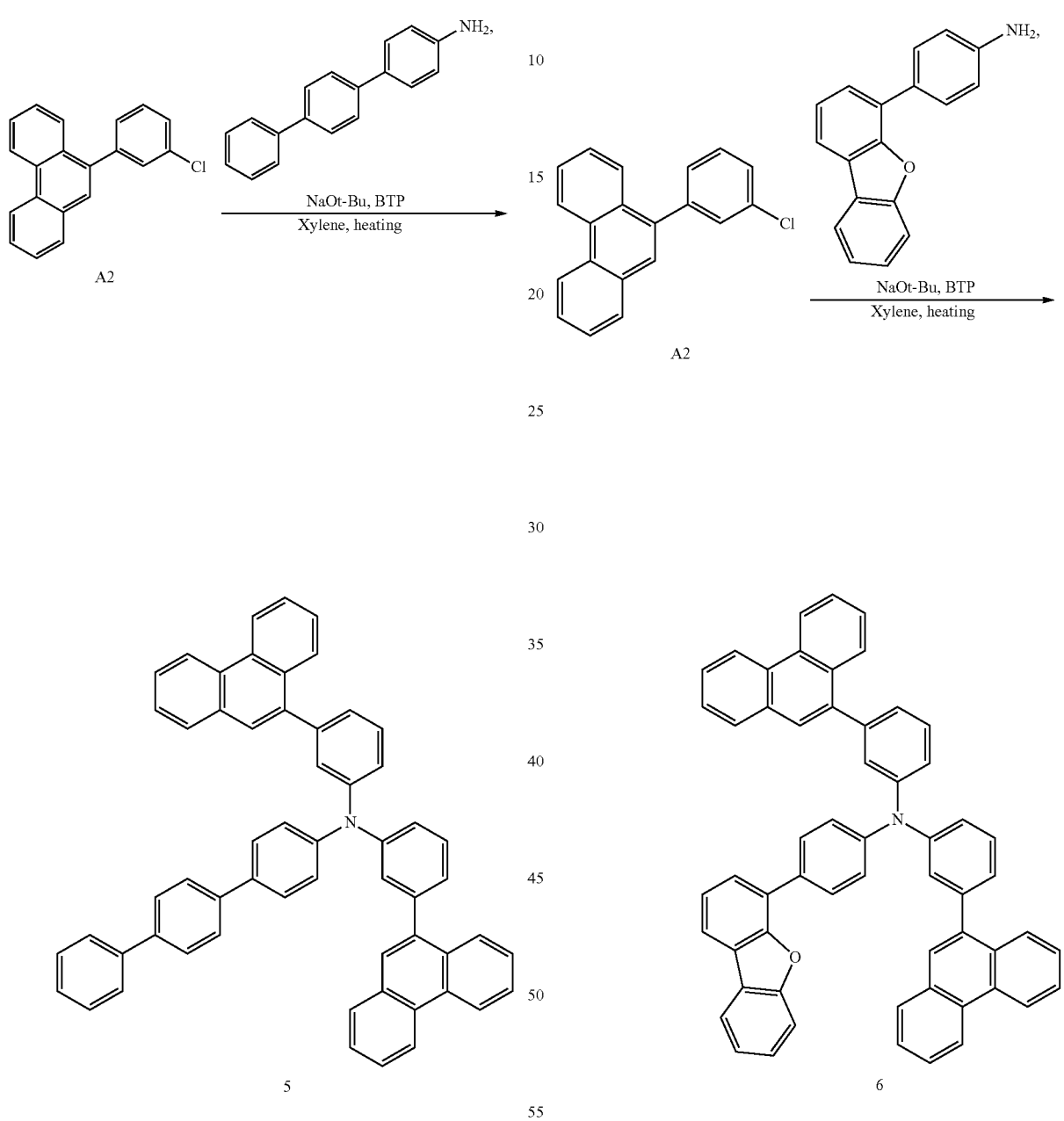

The compound 5 (N,N-bis(3-(phenanthren-9-yl)phenyl)-[1,1':4',1''-terphenyl]-4-amine) was obtained in the same manner as in Synthesis Example 7, except that [1,1'; 4',1''-terphenyl]-4-amine was used instead of the compound int. 1, and the compound A2 was used instead of 4-chloro-1,1'; 2',1''-terphenyl.

MS[M+H]$^+$=750.96

The compound 6 (N-(4-(dibenzo[b,d]furan-4-yl)phenyl)-3-(phenanthren-9-yl)-N-(3-(phenanthren-9-yl)phenyl)aniline) was obtained in the same manner as in Synthesis Example 7, except that 4-(dibenzo[b,d]furan-4-yl)aniline was used instead of the compound int. 1, and the compound A2 was used instead of 4-chloro-1,1'; 2',1''-terphenyl.

MS[M+H]$^+$=764.94

Synthesis Example 12

(Synthesis of Compound 7)

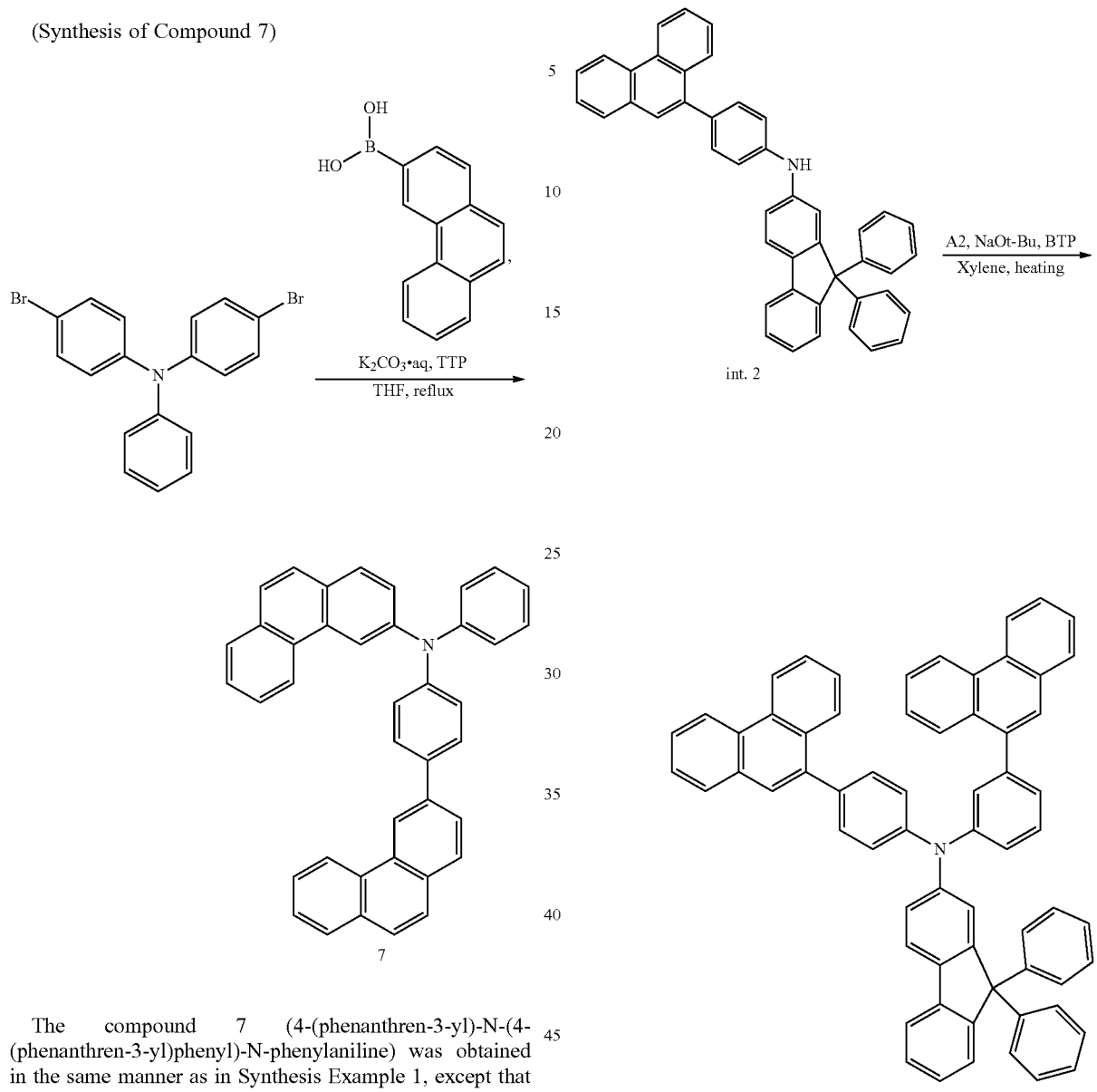

The compound 7 (4-(phenanthren-3-yl)-N-(4-(phenanthren-3-yl)phenyl)-N-phenylaniline) was obtained in the same manner as in Synthesis Example 1, except that 4-bromo-N-(4-bromophenyl)-N-phenylaniline was used instead of 9-bromophenanthrene, and phenanthrene-3-boronic acid was used instead of 4-chlorophenylboronic acid.

MS[M+H]$^+$=598.76

Synthesis Example 13

(Synthesis of Compound 8)

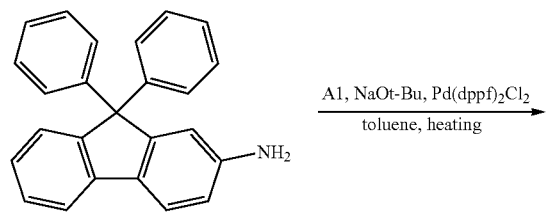

(1) The compound int. 2 (N-(4-(phenanthren-9-yl)phenyl)-9,9-Biphenyl-9H-fluoren-2-amine) was obtained in the same manner as in Synthesis Example 7, except that 9,9-diphenyl-9H-fluoren-2-amine was used instead of the compound int. 1, and the compound A1 was used instead of 4-chloro-1,1'; 2',1"-terphenyl.

MS[M+H]$^+$=586.75

(2) The compound 8 (N-(3-(phenanthren-9-yl)phenyl)-N-(4-(phenanthren-9-yl)phenyl)-9,9-diphenyl-9H-fluoren-2-amine) was obtained in the same manner as in Synthesis Example 7, except that the compound int. 2 was used instead of the compound int. 1, and the compound A2 was used instead of 4-chloro-1,1'; 2',1"-terphenyl.

MS[M+H]$^+$=839.07

Synthesis Example 14

(Synthesis of Compound 9)

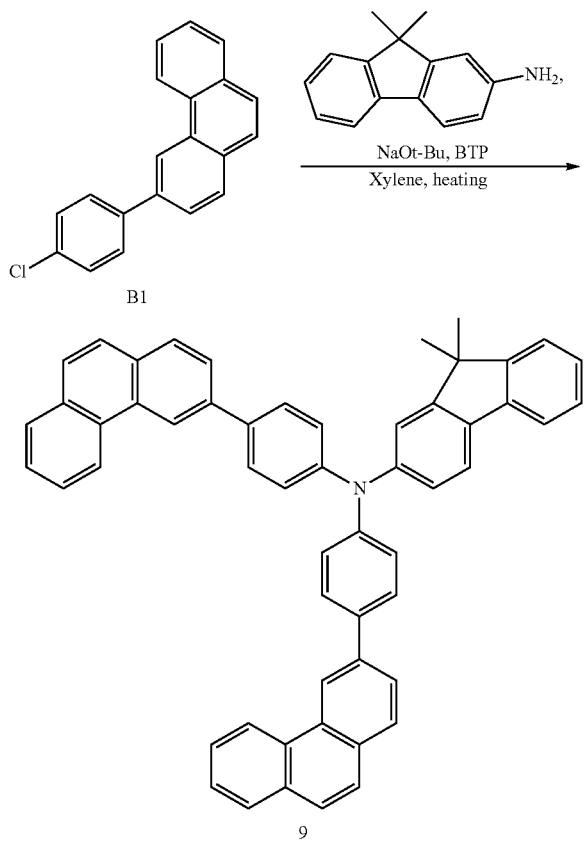

The compound 9 (9,9-dimethyl-N,N-bis(4-(phenanthren-3-yl)phenyl)-9H-fluoren-2-amine) was obtained in the same manner as in Synthesis Example 7, except that 9,9-dimethyl-9H-fluoren-2-amine was used instead of the compound int. 1, and the compound B1 was used instead of 4-chloro-1,1'; 2',1''-terphenyl.

MS[M+H]$^+$=839.07

Synthesis Example 15

(Synthesis of Compound 10)

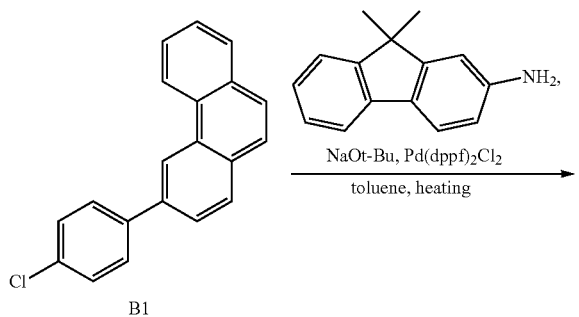

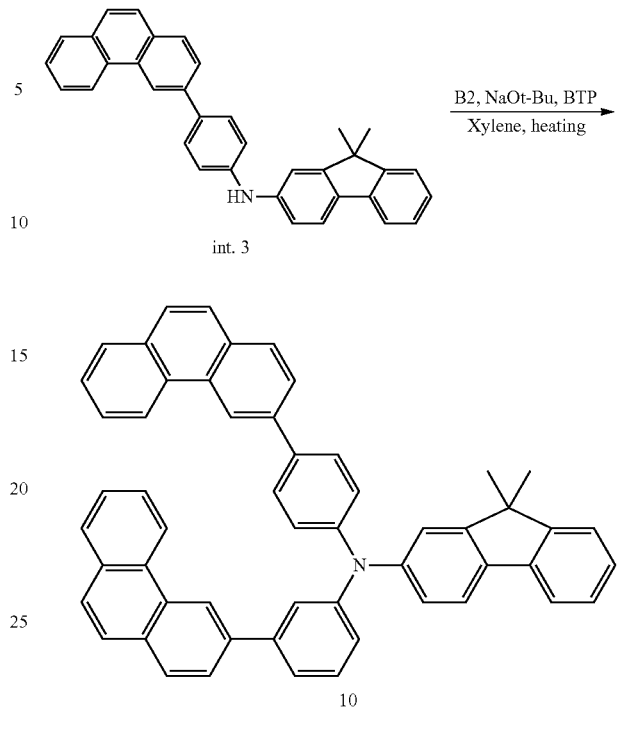

(1) The compound int. 3 (9,9-dimethyl-N-(4-(phenanthren-3-yl)phenyl)-9H-fluoren-2-amine) was obtained in the same manner as in Synthesis Example 7, except that 9,9-dimethyl-9H-fluoren-2-amine was used instead of the compound int. 1, and the compound B1 was used instead of 4-chloro-1,1'; 2',1''-terphenyl.

MS[M+H]$^+$=462.61

(2) The compound 10 (9,9-dimethyl-N-(3-(phenanthren-3-yl)phenyl)-N-(4-(phenanthren-3-yl)phenyl)-9H fluoren-2-amine) was obtained in the same manner as in Synthesis Example 7, except that the compound int. 3 was used instead of the compound int. 1, and the compound B2 was used instead of 4-chloro-1,1'; 2',1''-terphenyl.

MS[M+H]$^+$=714.92

Synthesis Example 16

(Synthesis of Compound 11)

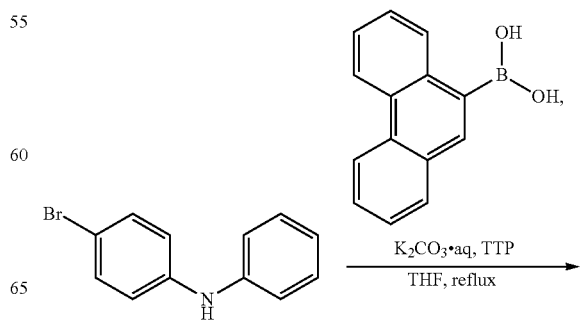

-continued

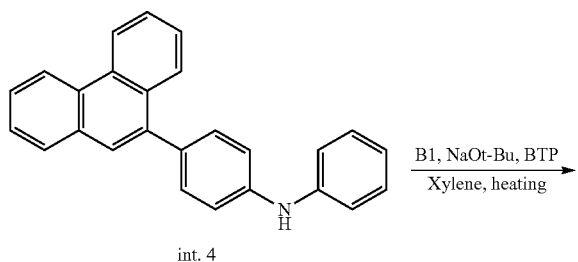

int. 4

B1, NaOt-Bu, BTP
———————————→
Xylene, heating

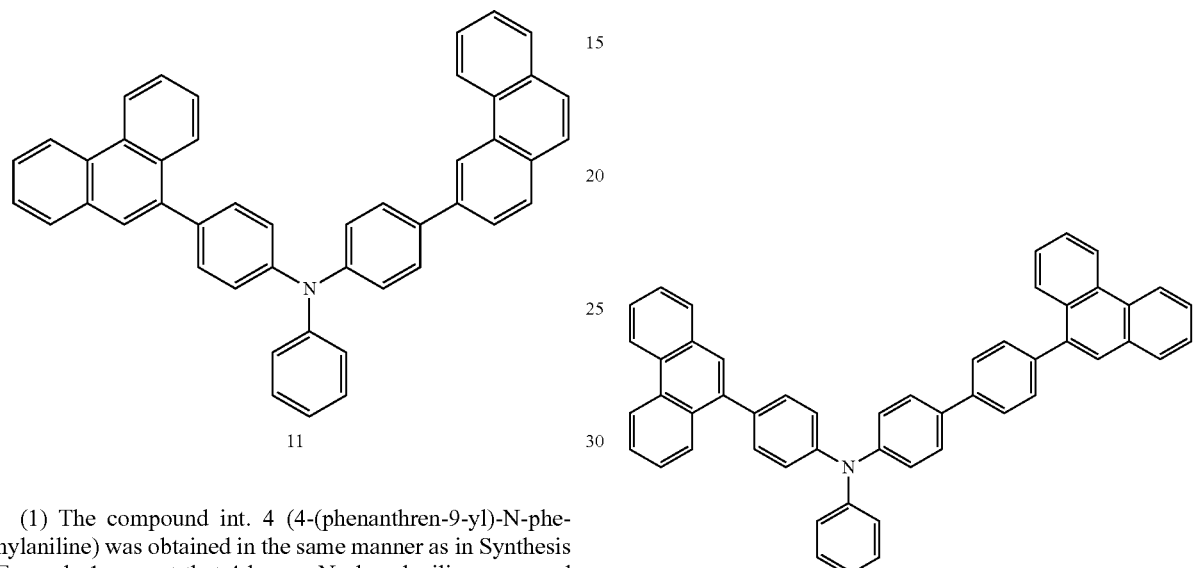

11

(1) The compound int. 4 (4-(phenanthren-9-yl)-N-phenylaniline) was obtained in the same manner as in Synthesis Example 1, except that 4-bromo-N-phenylaniline was used instead of 9-bromophenanthrene, and phenanthrene-9-boronic acid was used instead of 4-chlorophenylboronic acid.

MS[M+H]$^+$=346.46

(2) The compound 11 (4-(phenanthren-3-yl)-N-(4-(phenanthren-9-yl)phenyl)-N-phenylaniline) was obtained in the same manner as in Synthesis Example 7, except that the compound int. 4 was used instead of the compound int. 1, and the compound B3 was used instead of 4-chloro-1,1'; 2',1"-terphenyl.

MS[M+H]$^+$=598.76

Synthesis Example 17

(Synthesis of Compound 12)

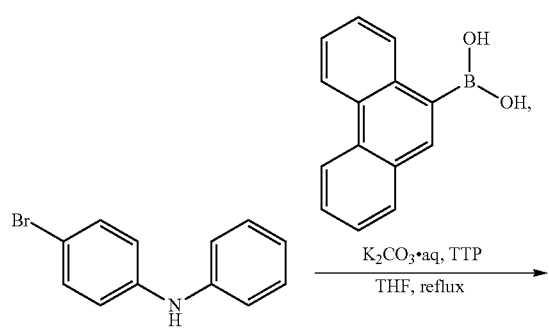

-continued

int. 4

A3, NaOt-Bu, BTP
———————————→
Xylene, heating

12

The compound 12 (4'-(phenanthren-9-yl)-N-(4-(phenanthren-9-yl)phenyl)-N-phenyl-[1,1'-biphenyl]-4-amine) was obtained in the same manner as in Synthesis Example 7, except that the compound int. 4 was used instead of the compound int. 1, and the compound A3 was used instead of 4-chloro-1,1'; 2',1"-terphenyl.

MS[M+H]$^+$=673.86

Synthesis Example 18

(Synthesis of Compound 13)

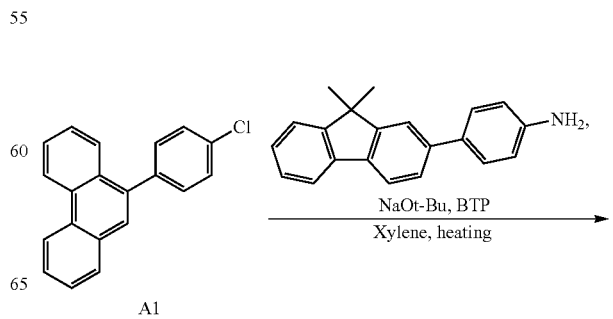

A1

-continued

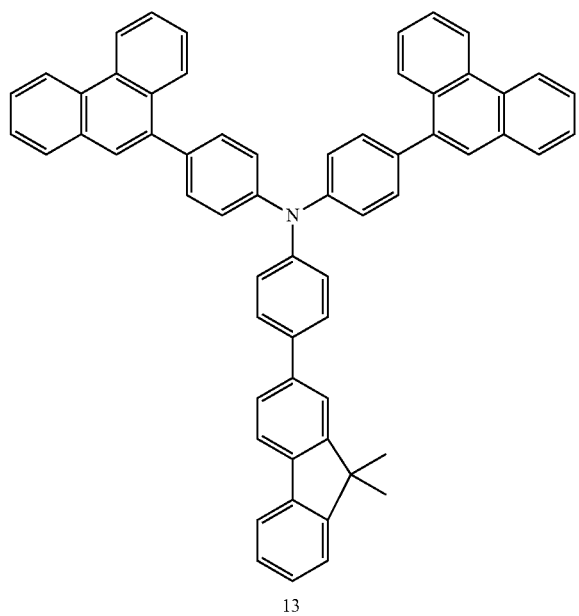

13

The compound 13 (4-(9,9-dimethyl-9H-fluoren-2-yl)-N,N-bis(4-(phenanthren-9-yl)phenyl)aniline, 68%) was obtained in the same manner as in Synthesis Example 7, except that 4-(9,9-dimethyl-9H-fluoren-2-yl)aniline was used instead of the compound int. 1, and the compound A1 was used instead of 4-chloro-1,1'; 2',1''-terphenyl.

MS[M+H]$^+$=791.02

Example 1

A glass substrate (Corning 7059 glass) on which a thin film of ITO (indium tin oxide) was coated in a thickness of 1,000 Å was put into distilled water in which a detergent was dissolved, and ultrasonically washed. As the detergent, a product manufactured by Fischer Co., was used, and as the distilled water, distilled water twice filtered using a filter manufactured by Millipore Co., was used. After the ITO was washed for 30 minutes, ultrasonic washing was conducted twice repeatedly using distilled water for 10 minutes. After the washing using distilled water was completed, ultrasonic washing was conducted sequentially using isopropyl alcohol, acetone and methanol solvents, and drying was conducted.

On the ITO transparent electrode thus prepared, the following Compound HI-1 was thermally vacuum-deposited in a thickness of 500 Å to form a hole injection layer. The Compound 4 previously prepared in Synthesis Example 9 was vacuum deposited in a thickness of 900 Å on the hole injection layer to form a hole transport layer. Subsequently, the following Compound HT2 was vacuum deposited in a thickness of 50 Å on the hole transport layer to form a hole adjustment layer. The following Compound BH1 as a host and the following Compound BD1 as a dopant were mixed at a weight ratio of 25:1 and vacuum deposited in a thickness of 300 Å on the hole adjustment layer to form a light emitting layer. The following Compound E1 (300 Å) was vacuum deposited with the following compound LiQ at a weight ratio of 1:1 on the light emitting layer and sequentially thermally vacuum-deposited into an electron injection and transport layer. Lithium fluoride (LiF) with a thickness of 12 Å and aluminum with a thickness of 2,000 Å were sequentially deposited on the electron transport layer on the electron transport layer to form a cathode, thereby manufacturing an organic light emitting device.

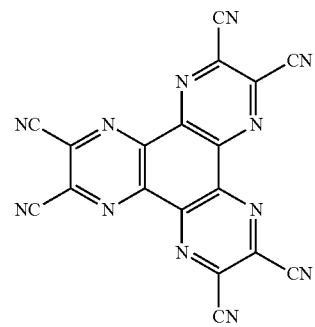

HI-1

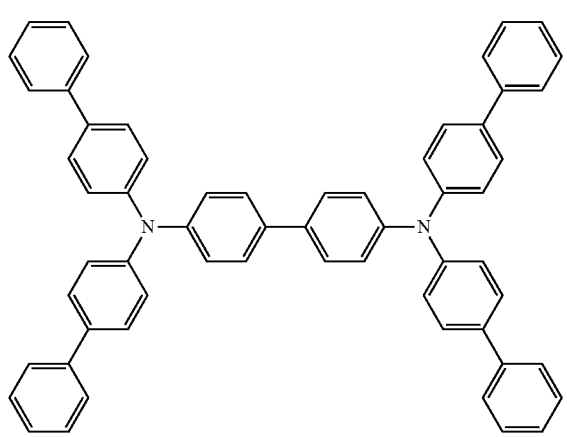

HT1

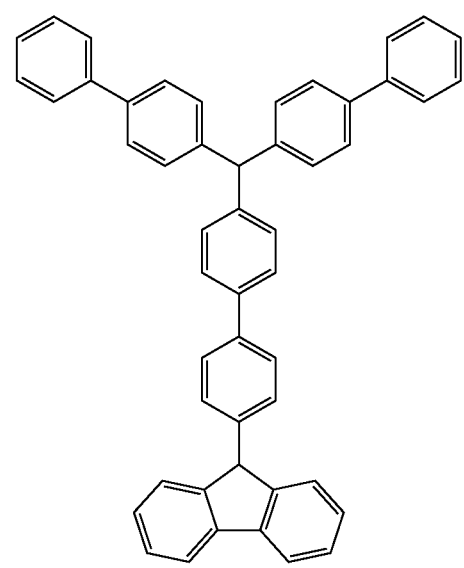

HT2

-continued

BH1

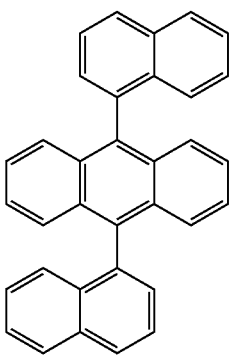

BD1

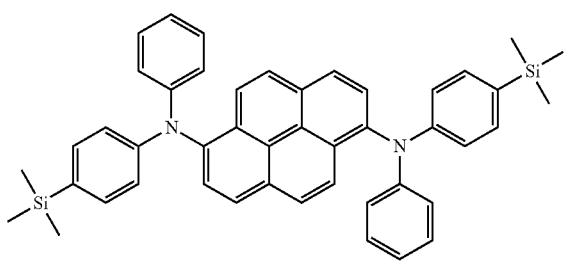

E1

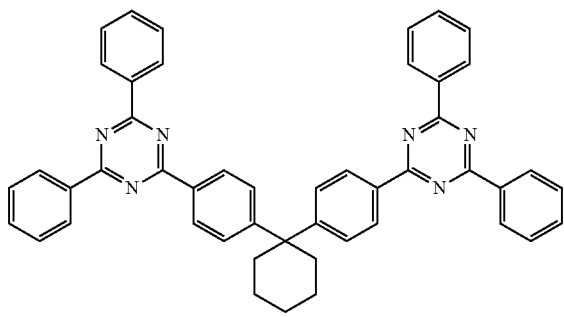

LiQ

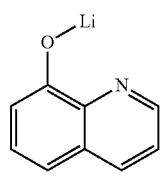

In the aforementioned procedure, the vapor deposition rate of the organic material was maintained at 1 Å/sec, the vapor deposition rate of lithium fluoride was maintained at 0.2 Å/sec, and the vapor deposition rate of aluminum was maintained at 3 to 7 Å/sec.

Examples 2 to 5

The organic light emitting devices were manufactured in the same manner as in Example 1, except that Compounds shown in Table 1 below were used instead of Compound 4.

Comparative Examples 1 to 4

The organic light emitting devices were manufactured in the same manner as in Example 1, except that Compounds shown in Table 1 below were used instead of Compound 4. In Table 1, Compounds HT4, HT5, HT6 and HT7 are as follows:

HT4

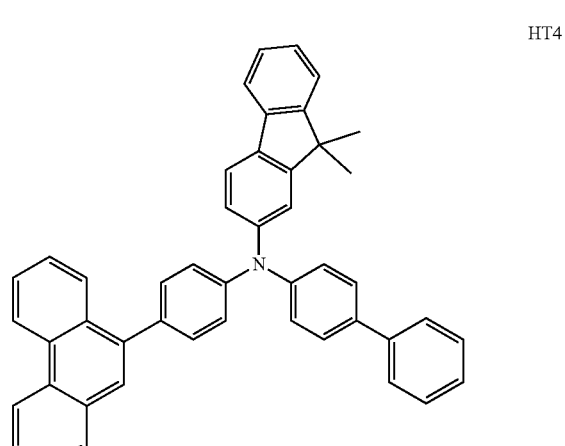

HT5

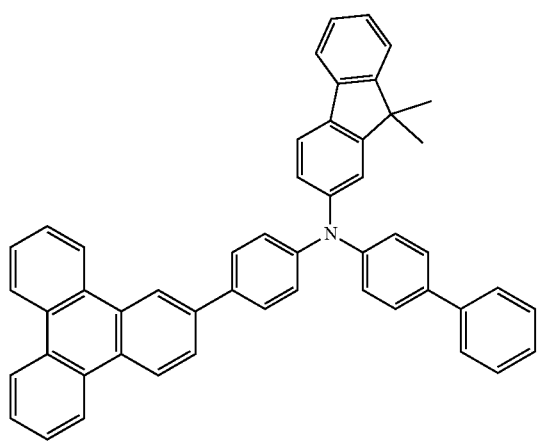

HT6

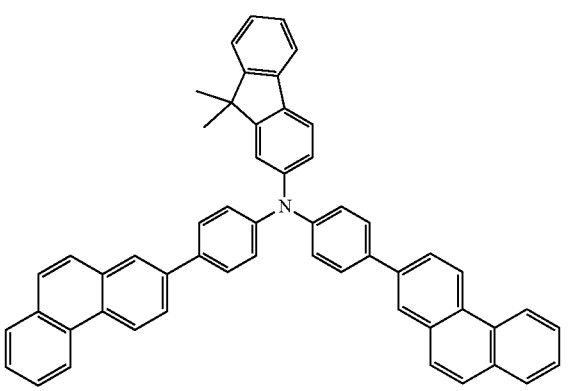

HT7

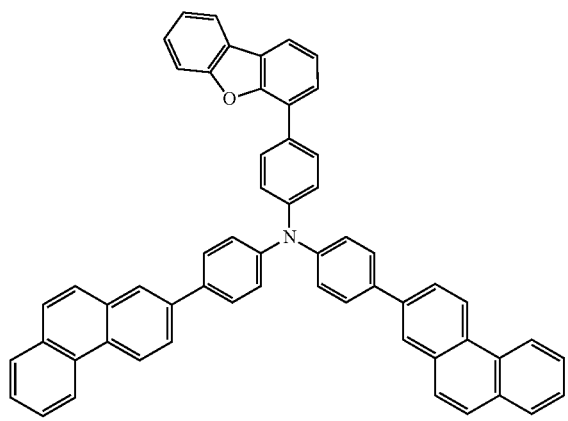

Test Example 1

A voltage, an efficiency, a color coordinate and a lifetime were measured when a current was applied to the organic light emitting devices manufactured in Examples 1 to 5 and Comparative Examples 1 to 4, and the results are shown in Table 1 below. T95 refers to the elapsed time for the luminance to decrease to 95% of its initial value (1600 nit).

On the ITO transparent electrode thus prepared, the following Compound HI-1 was thermally vacuum-deposited in a thickness of 500 Å to form a hole injection layer. The following Compound HT1 was vacuum deposited in a thickness of 900 Å on the hole injection layer to form a hole transport layer. Subsequently, the Compound 1 previously prepared in Synthesis Example 6 was vacuum deposited in a thickness of 50 Å on the hole transport layer to form a hole adjustment layer. The following Compound BH1 as a host and the following Compound BD1 as a dopant were mixed at a weight ratio of 25:1 and vacuum deposited in a thickness of 300 Å on the hole adjustment layer to form a light emitting layer. The following Compound E1 (300 Å) was vacuum deposited with the following compound LiQ at a weight ratio of 1:1 on the light emitting layer and sequentially thermally vacuum-deposited into an electron injection and transport layer. Lithium fluoride (LiF) with a thickness of 12 Å and aluminum with a thickness of 2,000 Å were sequentially deposited on the electron transport layer on the electron transport layer to form a cathode, thereby manufacturing an organic light emitting device.

TABLE 1

| | Hole transport layer | Hole adjustment layer | Voltage (V@20 mA/cm$^2$) | Efficiency (cd/A@20 mA/cm$^2$) | color coordinate (x,y) | T95 (hr) |
|---|---|---|---|---|---|---|
| Example 1 | Compound 4 | HT2 | 3.45 | 6.63 | (0.134, 0.137) | 50.2 |
| Example 2 | Compound 6 | HT2 | 3.41 | 6.58 | (0.135, 0.138) | 55.2 |
| Example 3 | Compound 9 | HT2 | 3.34 | 6.82 | (0.134, 0.138) | 51.2 |
| Example 4 | Compound 10 | HT2 | 3.42 | 6.72 | (0.136, 0.139) | 48.9 |
| Example 5 | Compound 13 | HT2 | 3.51 | 6.71 | (0.135, 0.138) | 49.0 |
| Comparative Example 1 | HT4 | HT2 | 3.82 | 5.70 | (0.134, 0.139) | 28.1 |
| Comparative Example 2 | HT5 | HT2 | 3.94 | 5.81 | (0.135, 0.138) | 21.0 |
| Comparative Example 3 | HT6 | HT2 | 3.78 | 5.98 | (0.134, 0.139) | 20.8 |
| Comparative Example 4 | HT7 | HT2 | 3.98 | 5.78 | (0.135, 0.138) | 29.1 |

Example 6

A glass substrate (Corning 7059 glass) on which a thin film of ITO (indium tin oxide) was coated in a thickness of 1,000 Å was put into distilled water in which a detergent was dissolved, and ultrasonically washed. As the detergent, a product manufactured by Fischer Co., was used, and as the distilled water, distilled water twice filtered using a filter manufactured by Millipore Co., was used. After the ITO was washed for 30 minutes, ultrasonic washing was conducted twice repeatedly using distilled water for 10 minutes. After the washing using distilled water was completed, ultrasonic washing was conducted sequentially using isopropyl alcohol, acetone, and methanol solvents, and drying was conducted.

HI-1

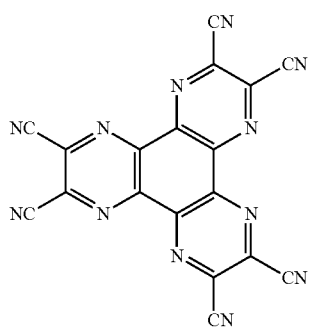

HT1
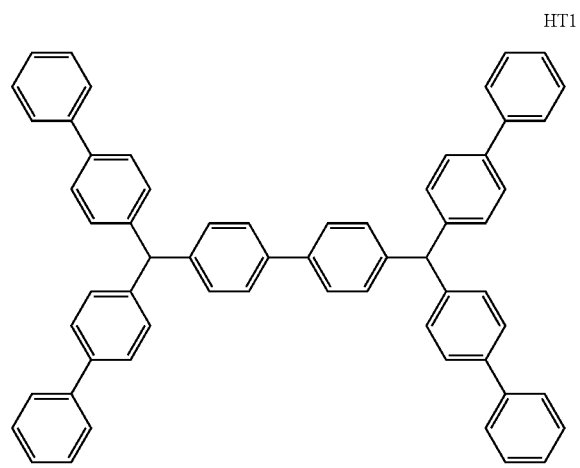

BH1
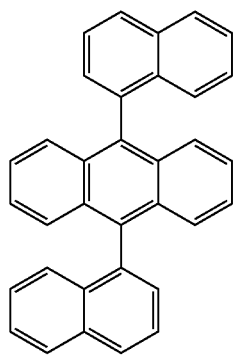

BD1
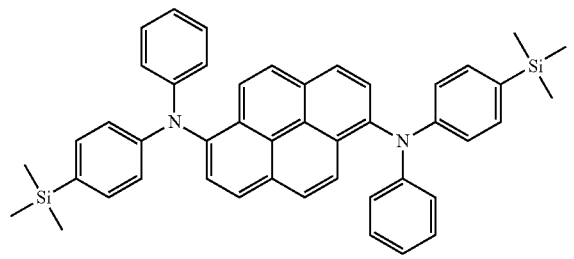

E1
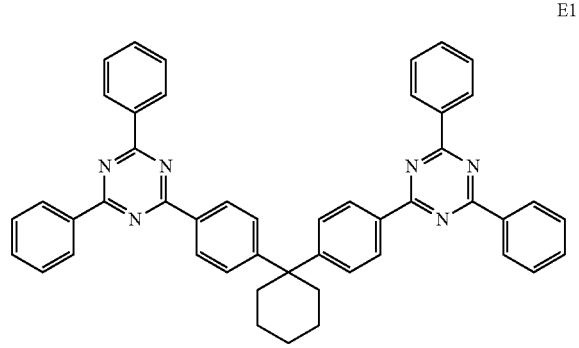

LiQ
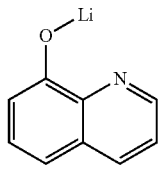

In the aforementioned procedure, the vapor deposition rate of the organic material was maintained at 1 Å/sec, the vapor deposition rate of lithium fluoride was maintained at 0.2 Å/sec, and the vapor deposition rate of aluminum was maintained at 3 to 7 Å/sec.

Examples 7 to 18

The organic light emitting devices were manufactured in the same manner as in Example 6, except that Compounds shown in Table 2 below were used instead of Compound 1

Example 19

An organic light emitting device was manufactured in the same manner as in Example 5, except that Compound 4 was used instead of Compound HT1, and Compound 5 was used instead of Compound 1.

Example 20

An organic light emitting device was manufactured in the same manner as in Example 6, except that Compound 13 was used instead of Compound HT1.

Comparative Examples 5 to 10

The organic light emitting devices were manufactured in the same manner as in Example 6, except that Compounds shown in Table 2 below were used instead of Compound 1. In Table 2, Compounds HT4, HT5, HT6, and HT7 are as follows:

HT2
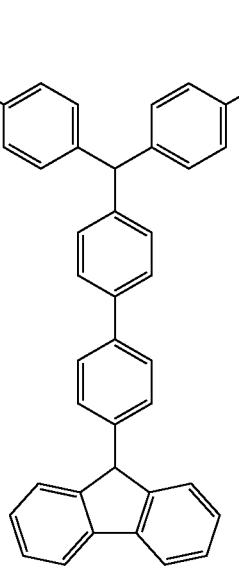

HT3

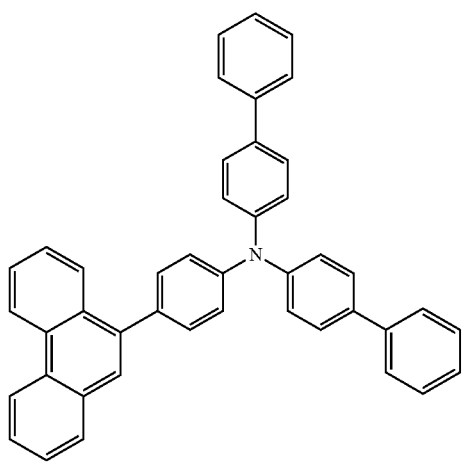

HT4

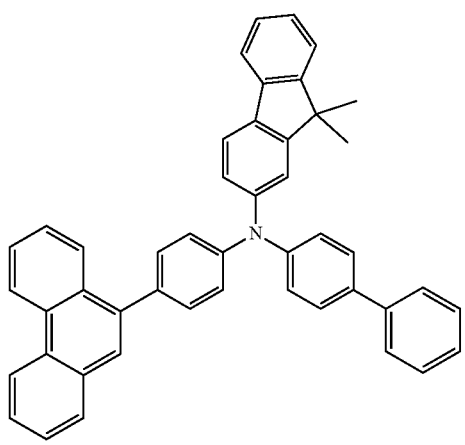

HT5

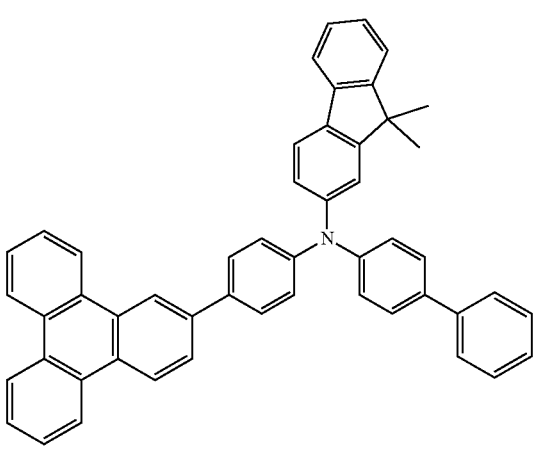

HT6

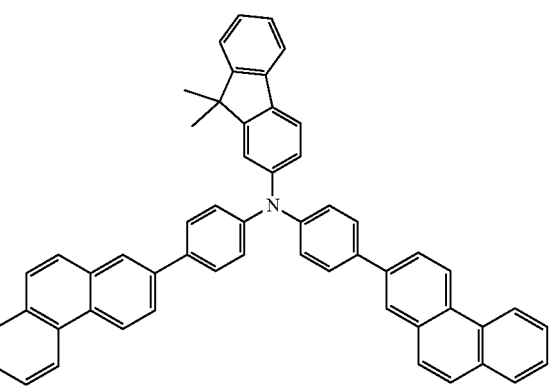

HT7

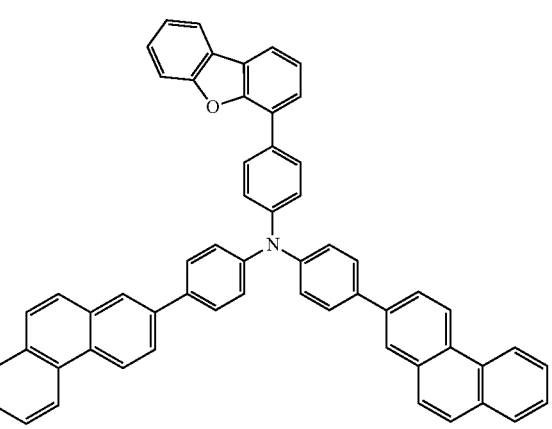

Test Example 2

A voltage, an efficiency, a color coordinate and a lifetime were measured when a current was applied to the organic light emitting devices manufactured in Examples 6 to 20 and Comparative Examples 5 to 10, and the results are shown in Table 2 below. T95 refers to the elapsed time for the luminance to decrease to 95% of its initial value (1600 nit).

TABLE 2

| | Hole transport layer | Hole adjustment layer | Voltage (V@20 mA/cm²) | Efficiency (cd/A@20 mA/cm²) | Color coordinate (x,y) | T95 (hr) |
|---|---|---|---|---|---|---|
| Example 6 | HT1 | Compound 1 | 3.33 | 6.89 | (0.135, 0.138) | 52.0 |
| Example 7 | HT1 | Compound 2 | 3.52 | 6.79 | (0.134, 0.138) | 48.0 |

TABLE 2-continued

| | Hole transport layer | Hole adjustment layer | Voltage (V@20 mA/cm$^2$) | Efficiency (cd/A@20 mA/cm$^2$) | Color coordinate (x,y) | T95 (hr) |
|---|---|---|---|---|---|---|
| Example 8 | HT1 | Compound 3 | 3.44 | 6.67 | (0.134, 0.138) | 46.8 |
| Example 9 | HT1 | Compound 4 | 3.52 | 6.87 | (0.138, 0.138) | 42.5 |
| Example 10 | HT1 | Compound 5 | 3.38 | 6.82 | (0.135, 0.139) | 46.5 |
| Example 11 | HT1 | Compound 6 | 3.39 | 6.81 | (0.135, 0.138) | 49.7 |
| Example 12 | HT1 | Compound 7 | 3.51 | 6.71 | (0.135, 0.139) | 50.1 |
| Example 13 | HT1 | Compound 8 | 3.45 | 6.63 | (0.134, 0.138) | 49.8 |
| Example 14 | HT1 | Compound 9 | 3.41 | 6.58 | (0.134, 0.138) | 47.4 |
| Example 15 | HT1 | Compound 10 | 3.43 | 7.01 | (0.135, 0.139) | 50.2 |
| Example 16 | HT1 | Compound 11 | 3.38 | 6.88 | (0.135, 0.138) | 48.3 |
| Example 17 | HT1 | Compound 12 | 3.41 | 6.78 | (0.135, 0.139) | 49.3 |
| Example 18 | HT1 | Compound 13 | 3.45 | 6.58 | (0.137, 0.134) | 47.1 |
| Example 19 | Compound 4 | Compound 5 | 3.49 | 6.71 | (0.135, 0.139) | 48.8 |
| Example 20 | Compound 13 | Compound 1 | 3.52 | 6.72 | (0.135, 0.138) | 50.1 |
| Comparative Example 5 | HT1 | HT2 | 3.82 | 5.71 | (0.134, 0.138) | 33.5 |
| Comparative Example 6 | HT1 | HT3 | 3.78 | 5.89 | (0.137, 0.135) | 28.2 |
| Comparative Example 7 | HT1 | HT4 | 3.75 | 5.91 | (0.134, 0.138) | 35.1 |
| Comparative Example 8 | HT1 | HT5 | 3.70 | 5.84 | (0.135, 0.137) | 29.4 |
| Comparative Example 9 | HT1 | HT6 | 4.13 | 5.13 | (0.137, 0.135) | 22.8 |
| Comparative Example 10 | HT1 | HT7 | 3.98 | 5.68 | (0.134, 0.138) | 23.1 |

Referring to Tables 1 and 2 above, it is confirmed that the compounds of Chemical Formula 1 play a role of hole transport and hole adjustment in organic electronic devices including organic light emitting devices, and can exhibit excellent characteristics in terms of efficiency, driving voltage, and stability.

DESCRIPTION OF SYMBOLS

1: substrate
2: anode,
3: light emitting layer
4: cathode
5: hole injection layer
6: hole transport layer
7: light emitting layer
8: electron transport layer
9: hole adjustment layer

The invention claimed is:

1. A compound of Chemical Formula 1:

[Chemical Formula 1]

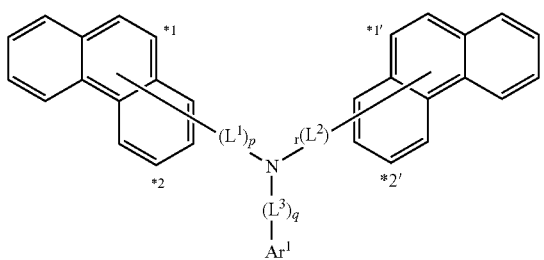

wherein in Chemical Formula 1:

L¹ is bonded to position *1, or *2;

L² is bonded to position *1', or *2';

L¹ is phenylene, biphenylene, terphenylene, 1-naphthylene, 2-naphthylene, dibenzofuranylene, dibenzothiophenylene, or carbazolylene, wherein the L¹ is unsubstituted or substituted with halogen, amino, nitrile, nitro, $C_{1-30}$ alkyl, $C_{2-30}$ alkenyl, $C_{2-30}$ alkynyl, $C_{1-30}$ alkoxy, $C_{6-30}$ aryloxy, or $C_{6-30}$ aryl;

L² is phenylene, terphenylene, 1-naphthylene, 2-naphthylene, dibenzofuranylene, dibenzothiophenylene, or carbazolylene, wherein the L² is unsubstituted or substituted with halogen, amino, nitrile, nitro, $C_{1-30}$ alkyl, $C_{2-30}$ alkenyl, $C_{2-30}$ alkynyl, $C_{1-30}$ alkoxy, $C_{6-30}$ aryloxy, or $C_{6-30}$ aryl;

L³ is phenylene, biphenylene, 1-naphthylene, 2-naphthylene, fluorenylene, dibenzofuranylene, dibenzothiophenylene, or carbazolylene, wherein the L³ is unsubstituted or substituted with deuterium, halogen, amino, nitrile, nitro, $C_{1-3}n$ alkyl, $C_{2-30}$ alkenyl, $C_{2-30}$ alkynyl, $C_{1-30}$ alkoxy, or $C_{6-30}$ aryloxy;

Ar¹ is:

(a) phenyl, biphenyl, fluorenyl, 9,9-dimethylfluorenyl, 9,9-diphenylfluorenyl, dibenzofuranyl, or dibenzothiophenyl, wherein the Ar¹ is unsubstituted or substituted with phenyl; or (b) terphenyl that is unsubstituted;

p and r are each independently 1;

q is 0 or 1;

provided that when Ar¹ is 9,9-dimethylfluorenyl, (i) L¹ and L² are respectively bonded to *2 and *2', or (ii) q is 1.

2. The compound of claim 1, wherein:

the Chemical Formula 1 is any one selected from the group consisting of the following Chemical Formulas 2-a, 2-b, and 2-c:

[Chemical Formula 2-a]

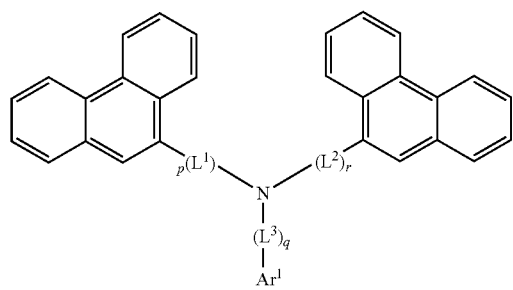

[Chemical Formula 2-b]

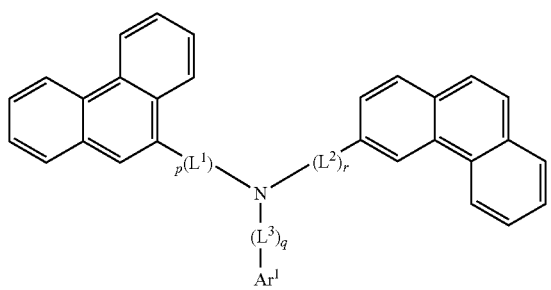

[Chemical Formula 2-c]

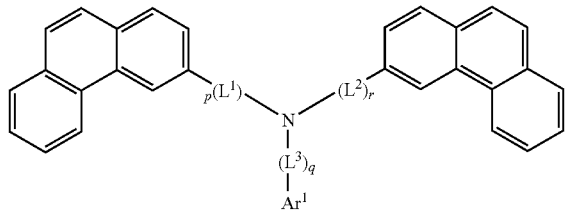

wherein in Chemical Formulas 2-a, 2-b and 2-c:

L¹, L², L³, Ar¹, p, r, and q are as defined in claim 1, respectively.

3. An organic electroluminescent device, comprising:

a first electrode;

a second electrode provided at a side opposite to the first electrode; and at least one layer of the organic material layers provided between the first electrode and the second electrode, wherein the at least one layer of the organic material layers includes the compound of claim 2.

4. The compound of claim 1, wherein:

the p and r are each independently 1; and

L¹ is phenylene or biphenylene; and

L² is phenylene.

5. An organic electroluminescent device, comprising:

a first electrode;

a second electrode provided at a side opposite to the first electrode; and at least one layer of the organic material layers provided between the first electrode and the second electrode, wherein the at least one layer of the organic material layers includes the compound of claim 4.

6. The compound of claim 1, wherein:

the q is 0 or 1; and the L³ is phenylene or naphthylene.

7. An organic electroluminescent device, comprising:

a first electrode;

a second electrode provided at a side opposite to the first electrode; and at least one layer of the organic material layers provided between the first electrode and the second electrode, wherein the at least one layer of the organic material layers includes the compound of claim 6.

8. An organic electroluminescent device, comprising:

a first electrode;

a second electrode provided at a side opposite to the first electrode; and at least one layer of the organic material layers provided between the first electrode and the second electrode, wherein the at least one layer of the organic material layers includes the compound of claim 1.

9. A compound selected from the group consisting of the following compounds:
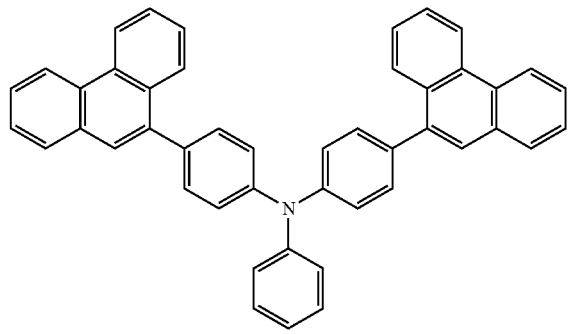
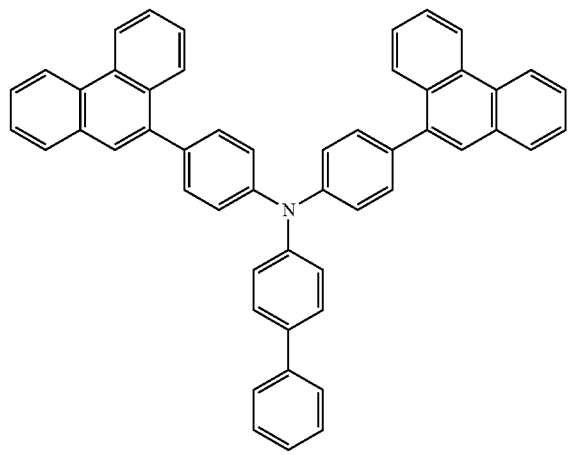
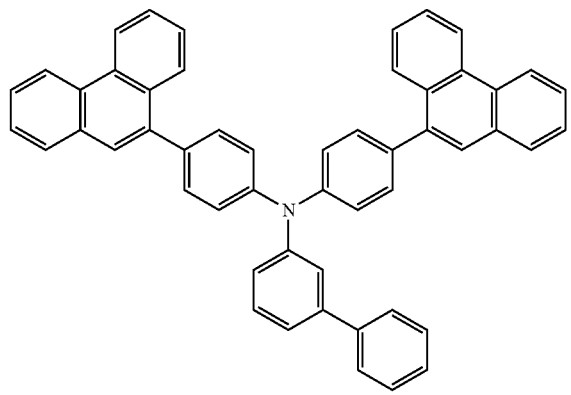
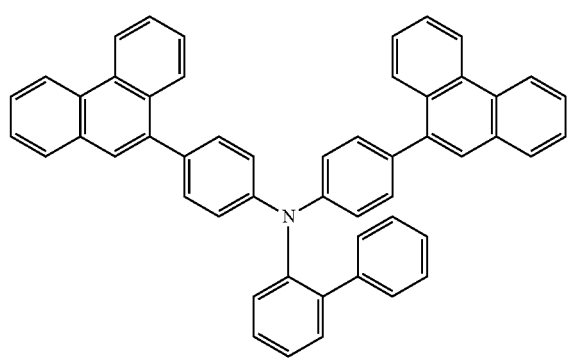
-continued
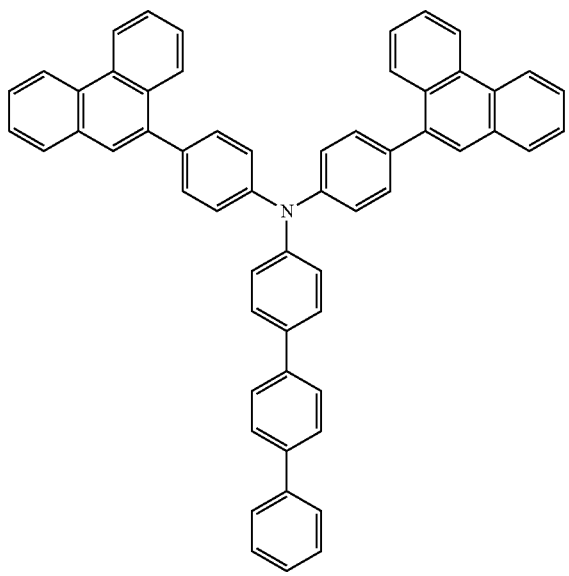
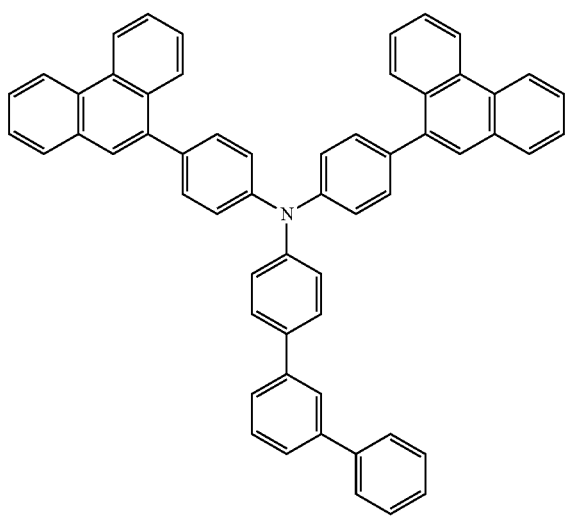
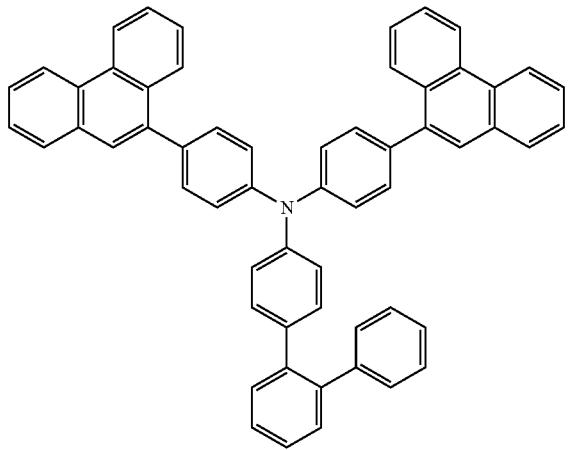

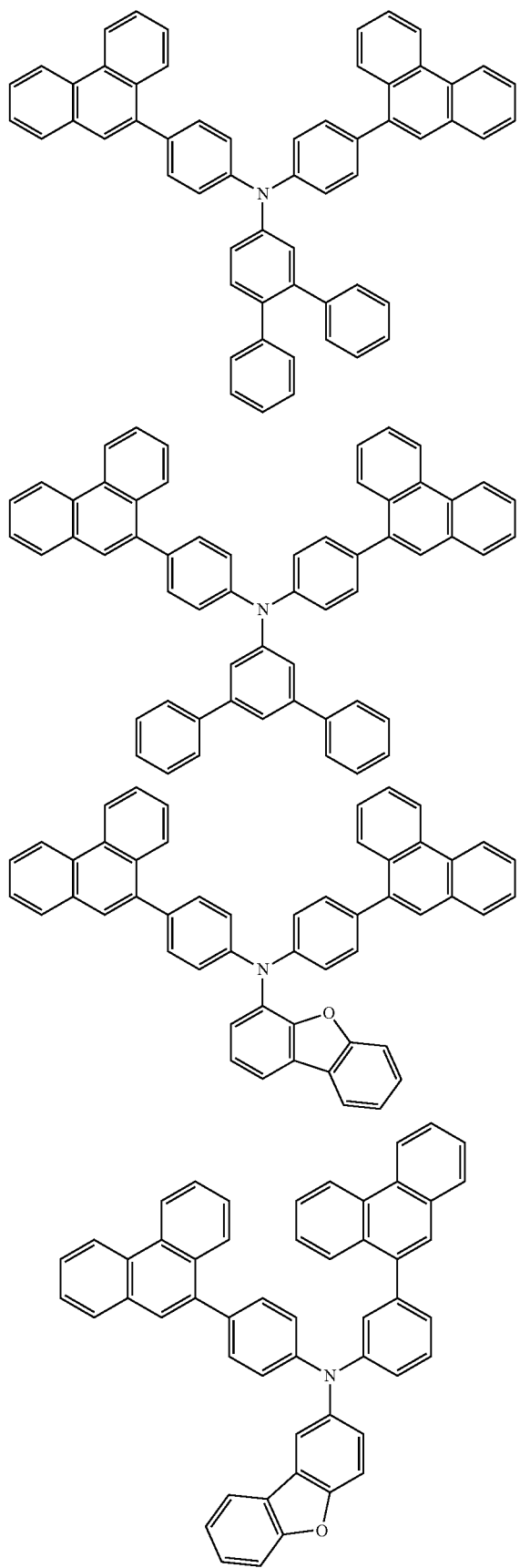
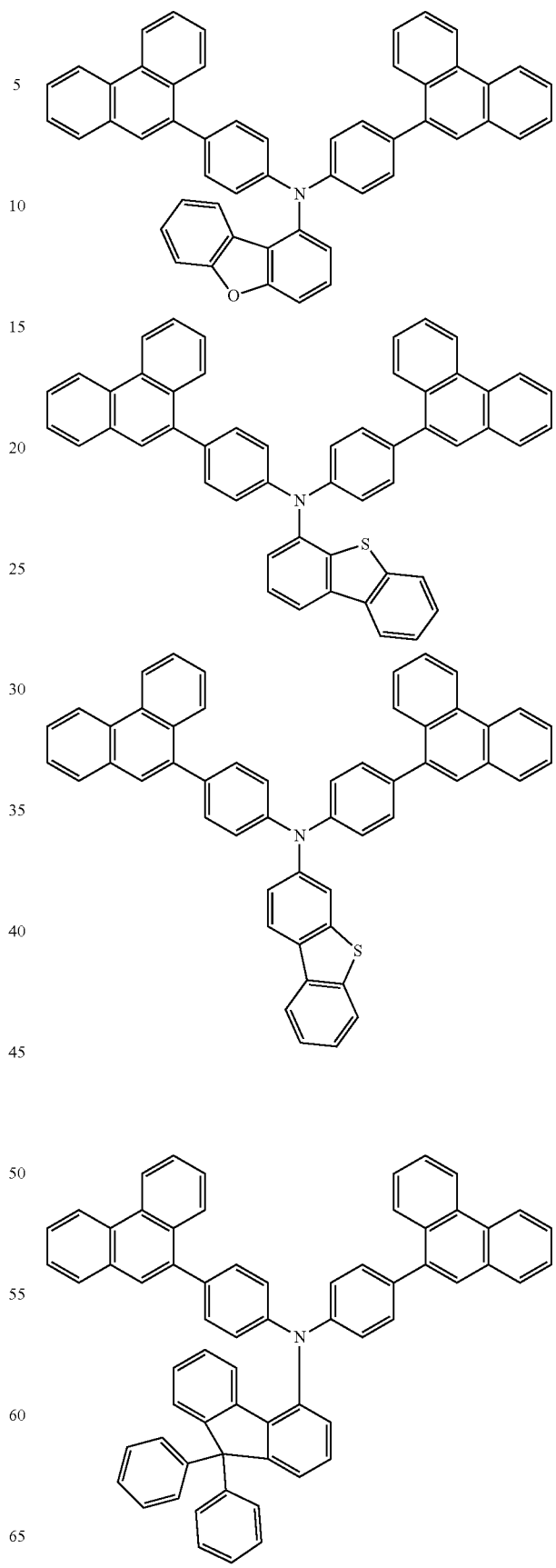

111
-continued
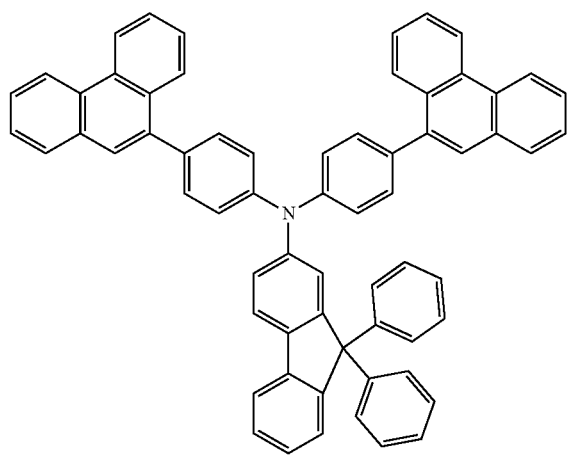
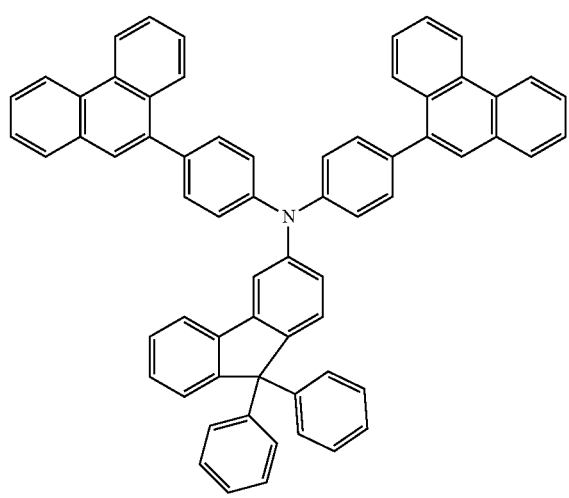
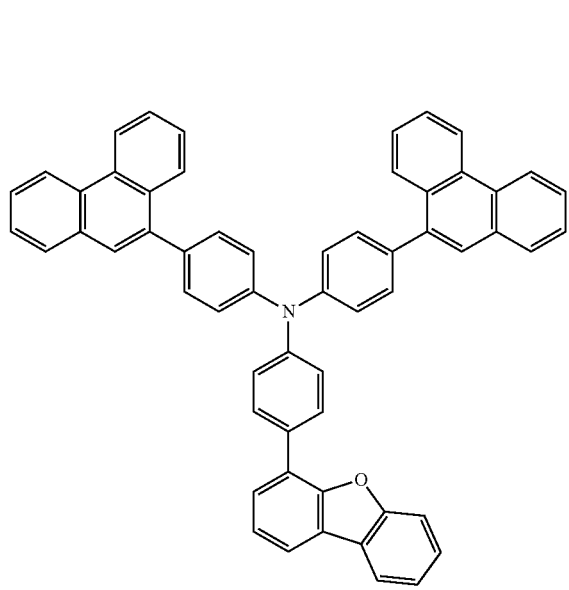
112
-continued
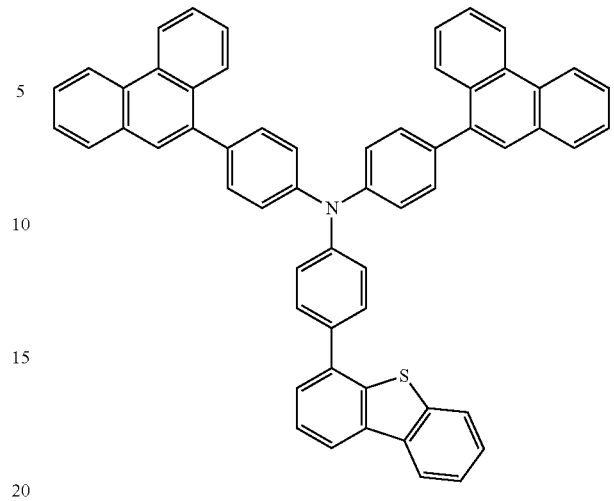
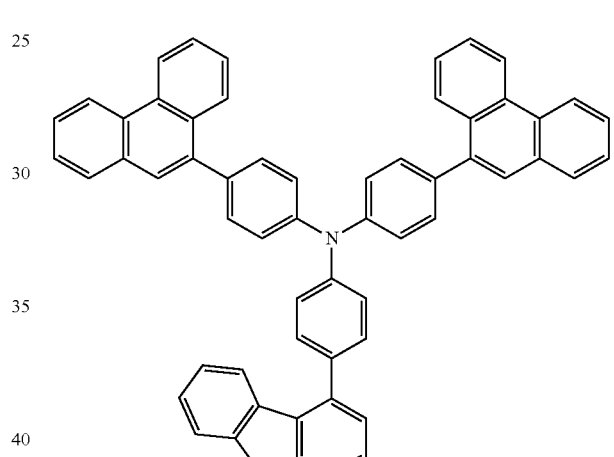
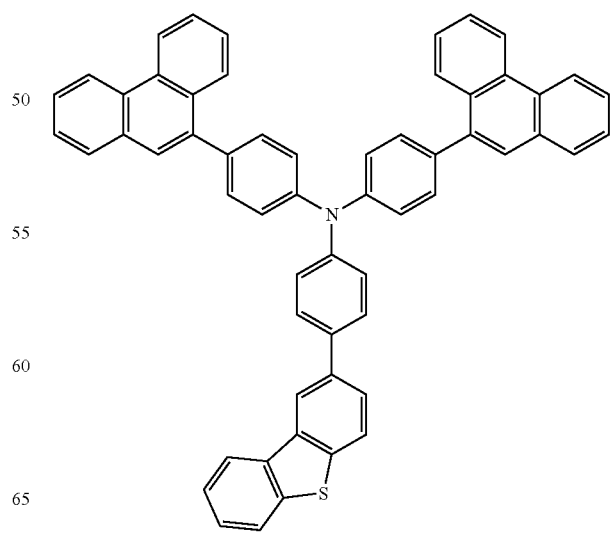

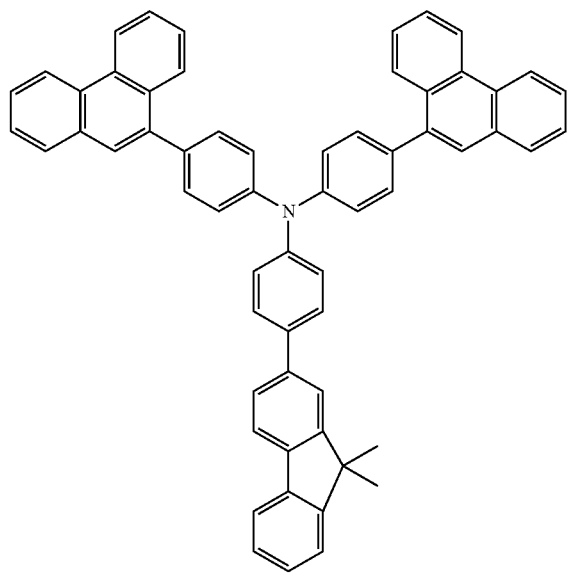
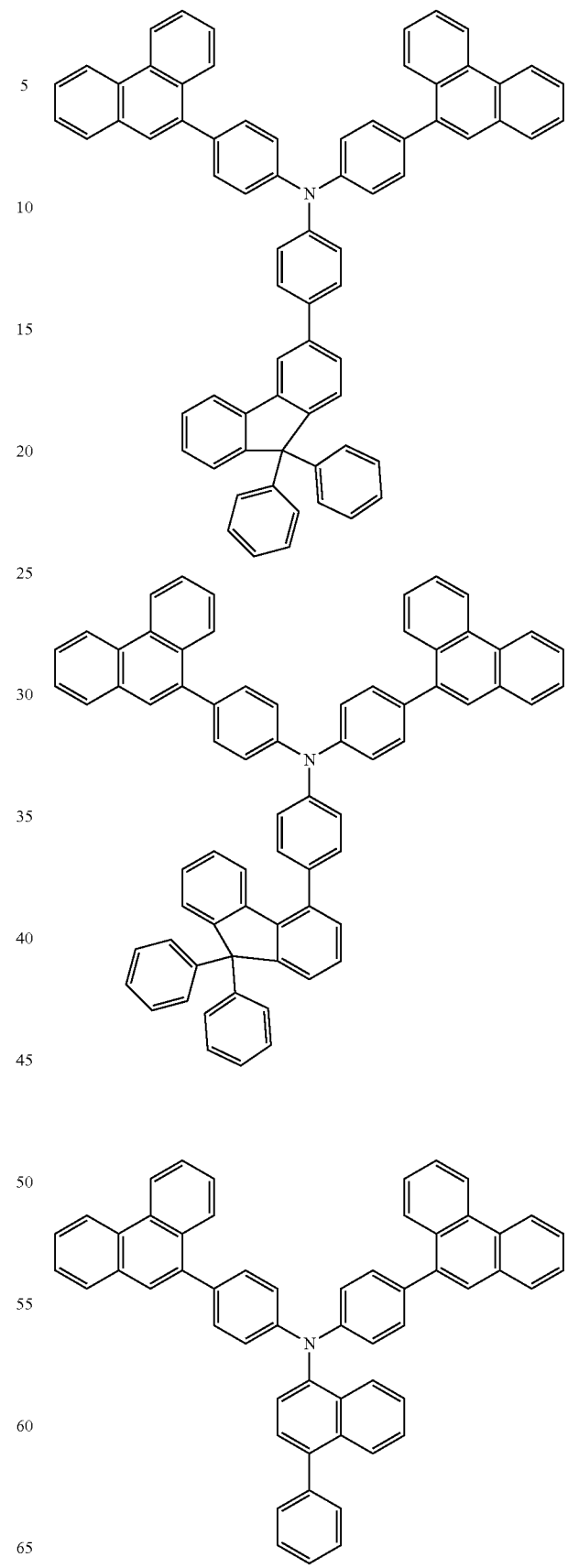

115
-continued
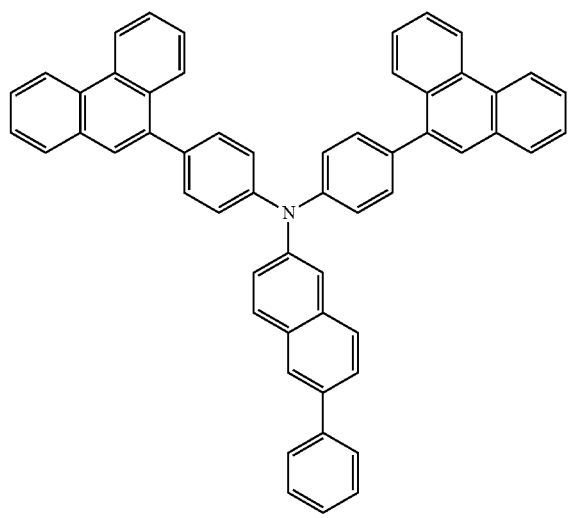
116
-continued
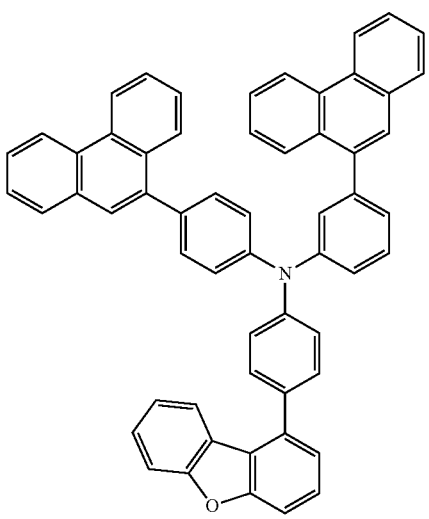
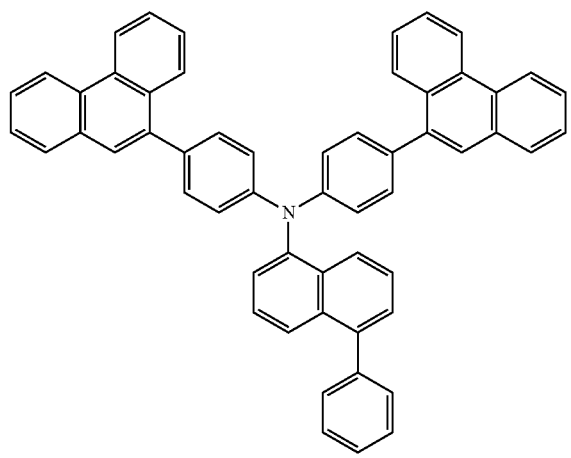
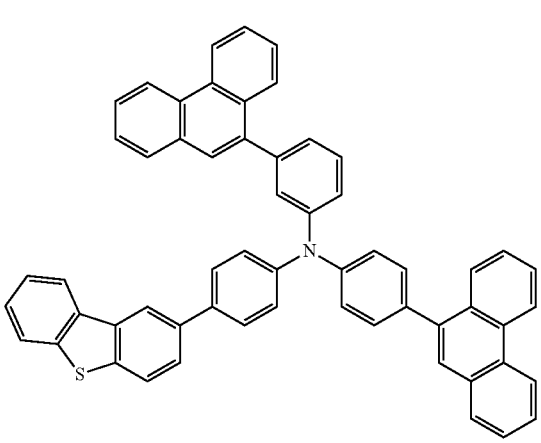
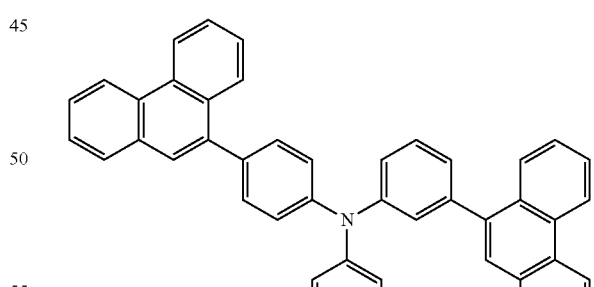
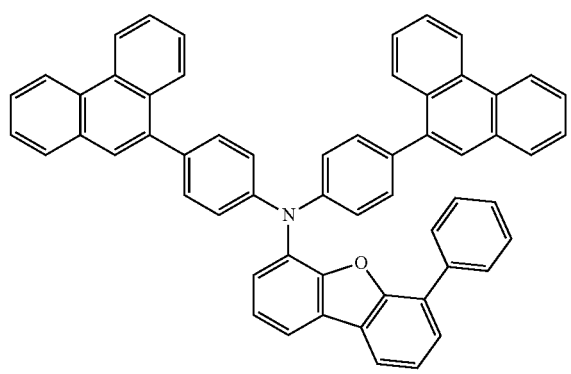
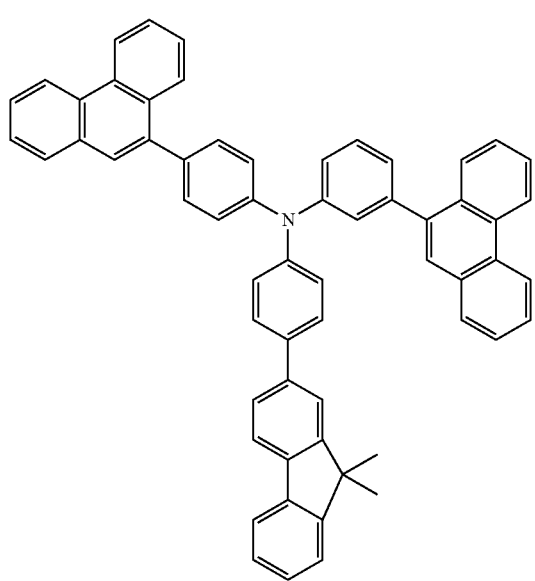

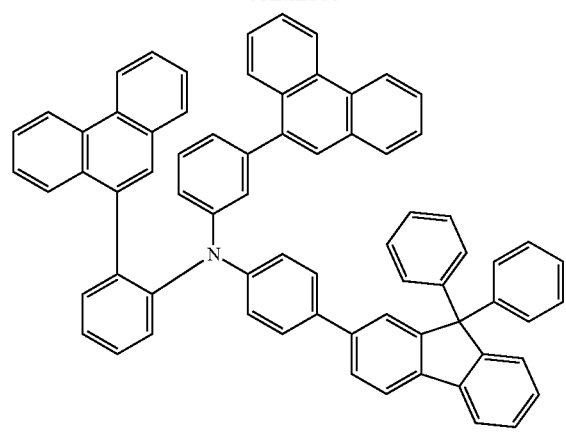
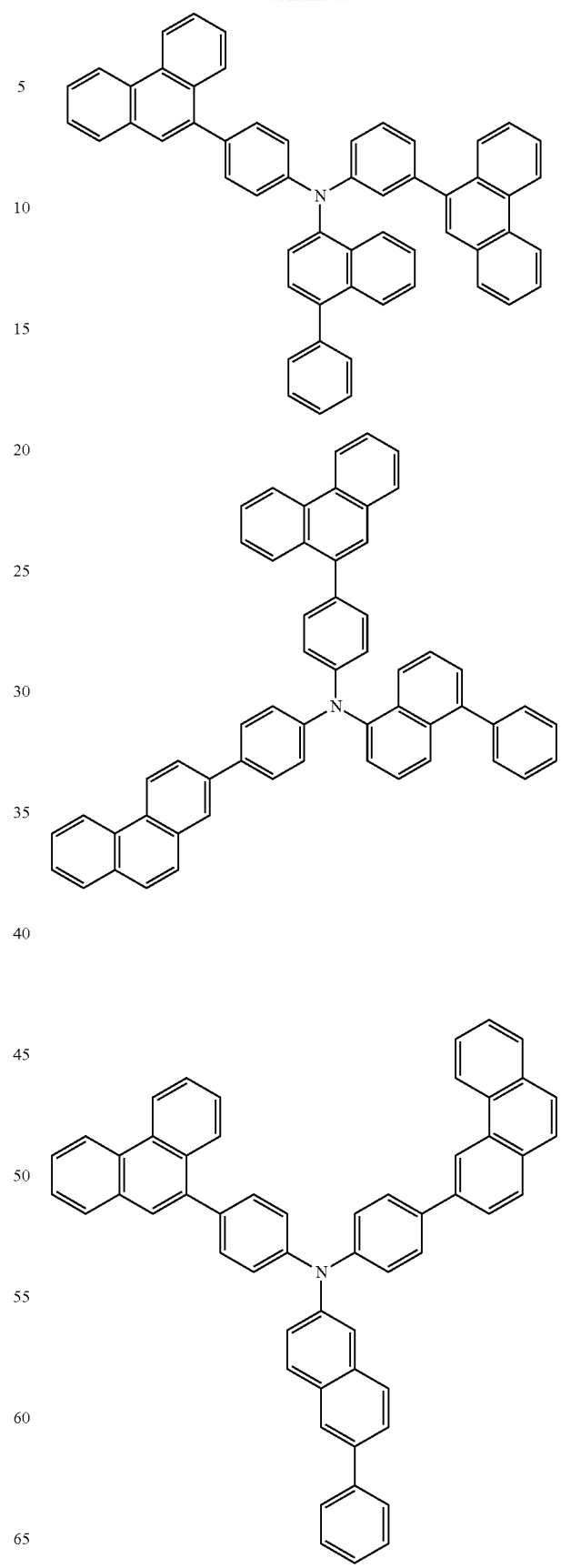

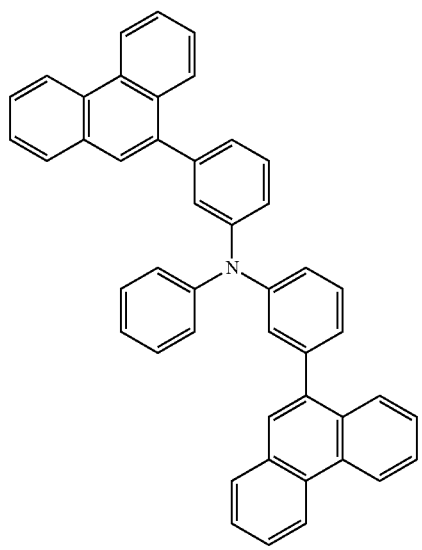
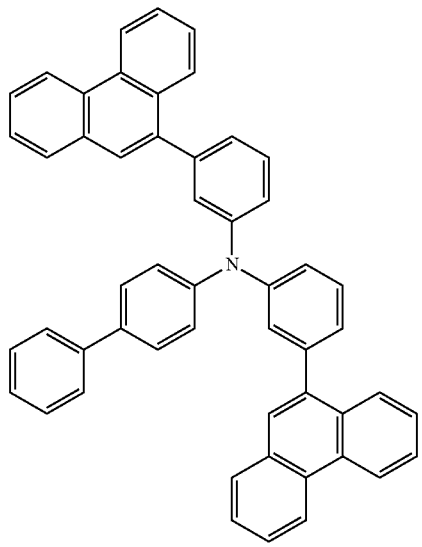
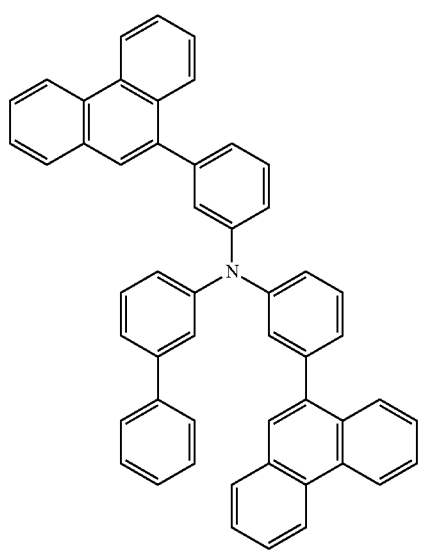
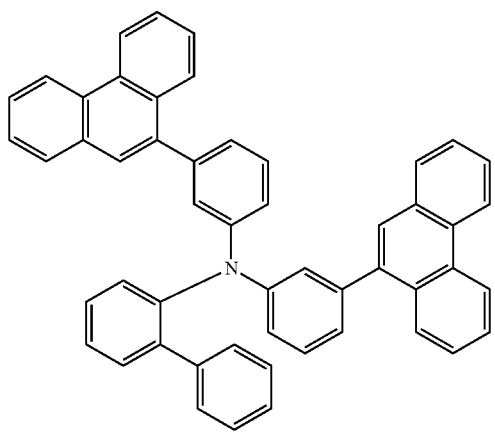
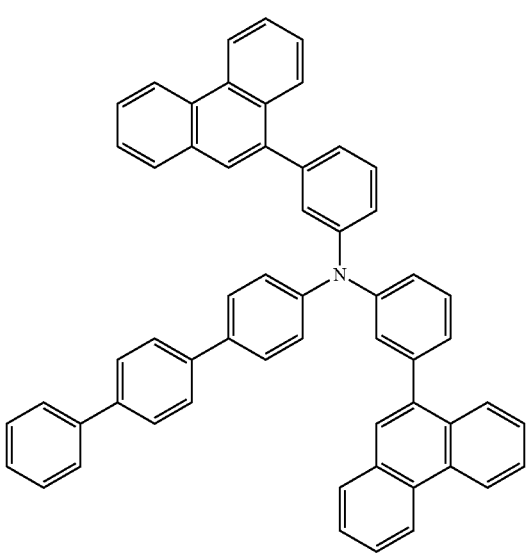
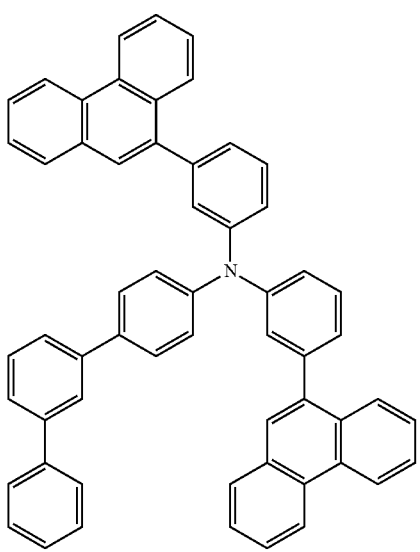

121
-continued
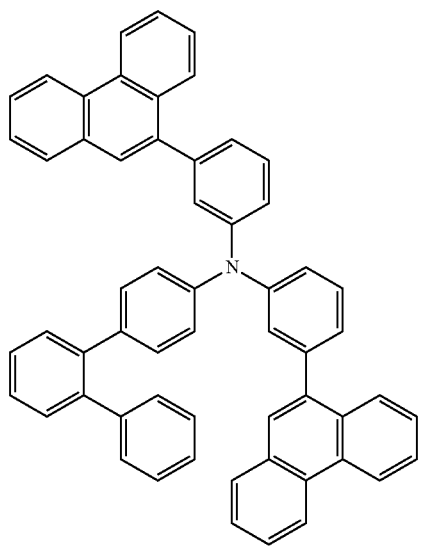
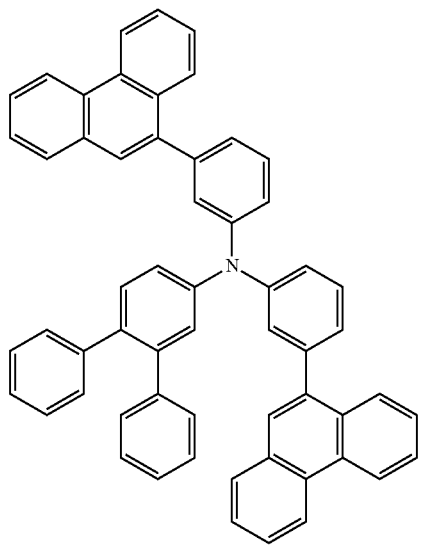
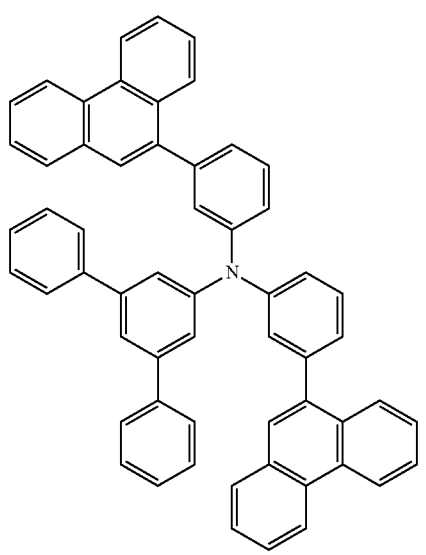
122
-continued
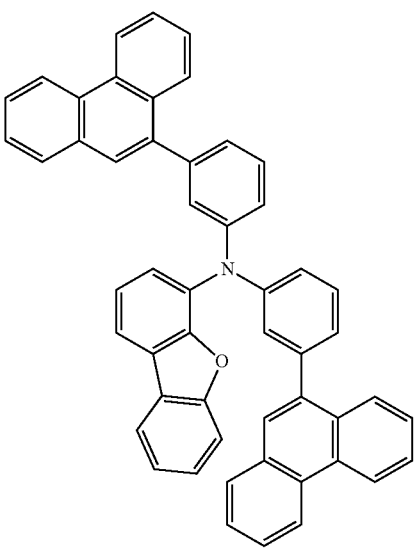
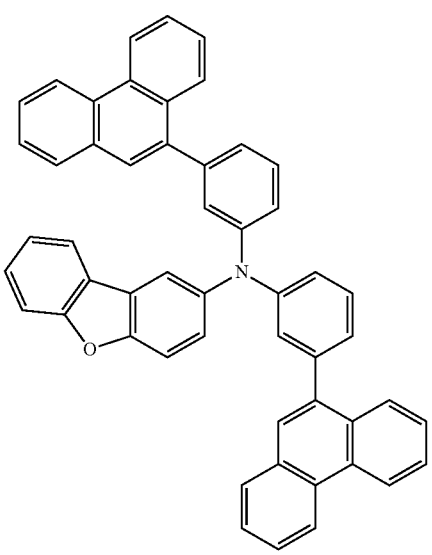
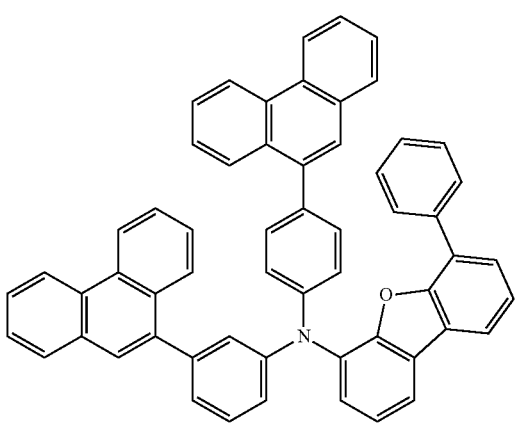

123
-continued
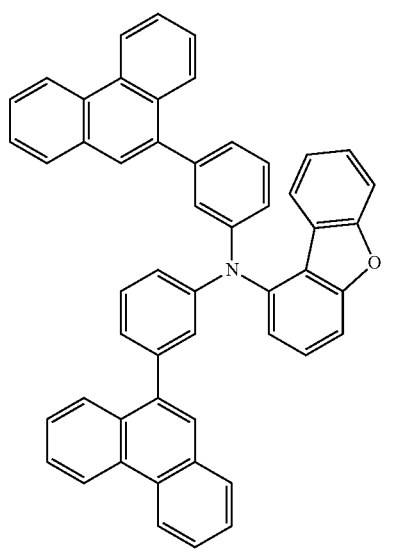
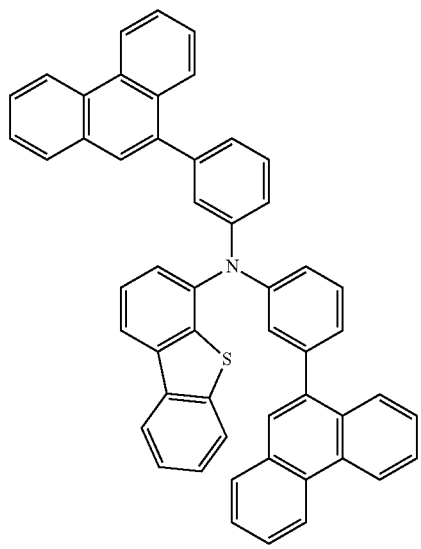
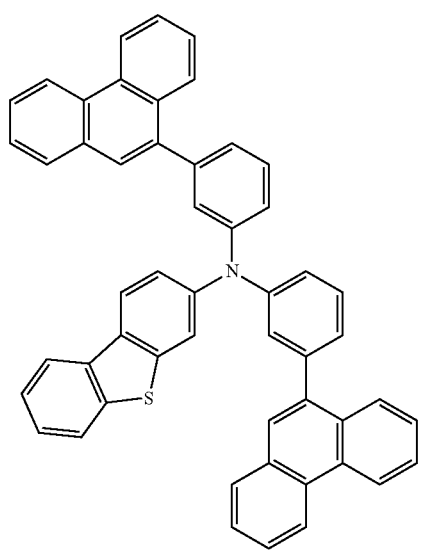
124
-continued
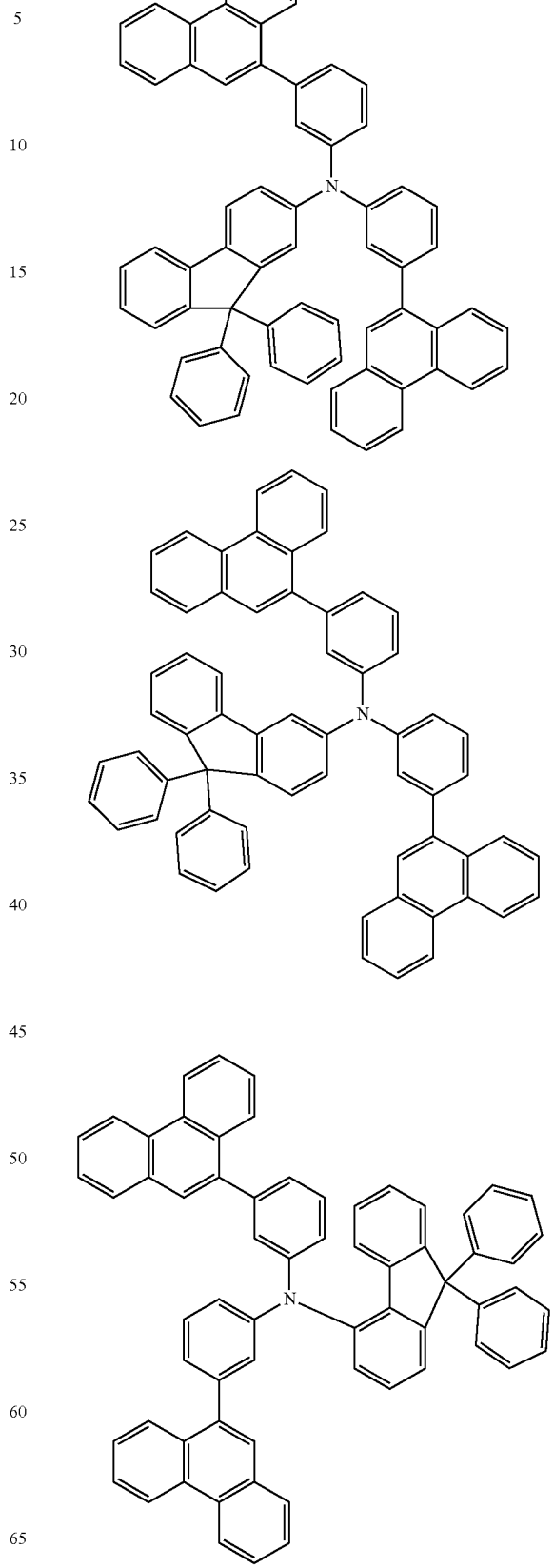

125
-continued
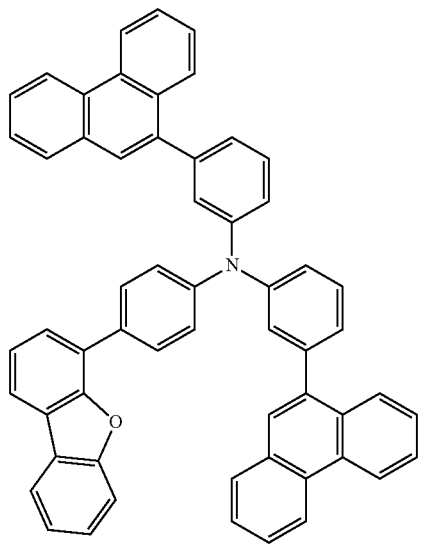
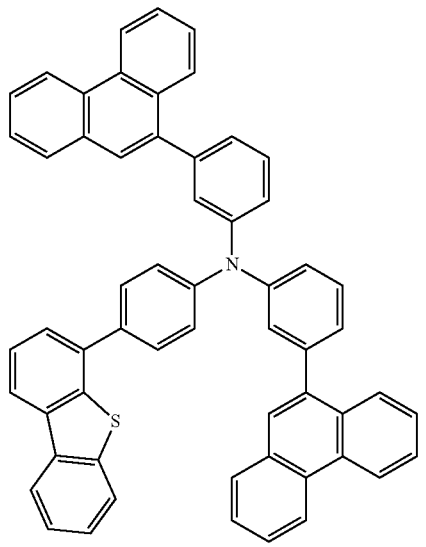
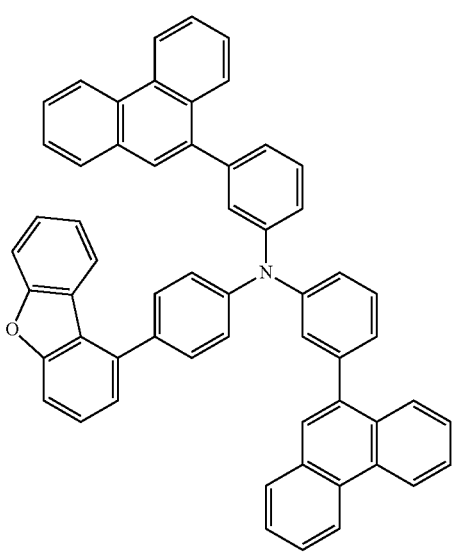
126
-continued
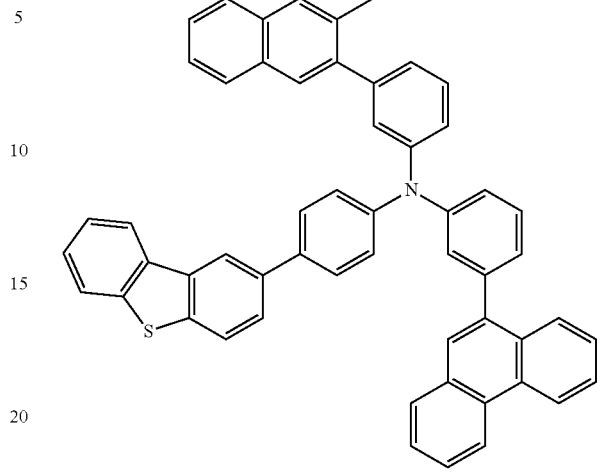
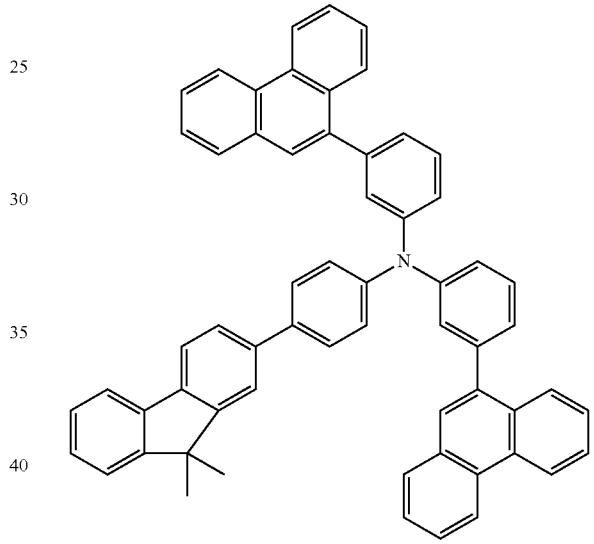
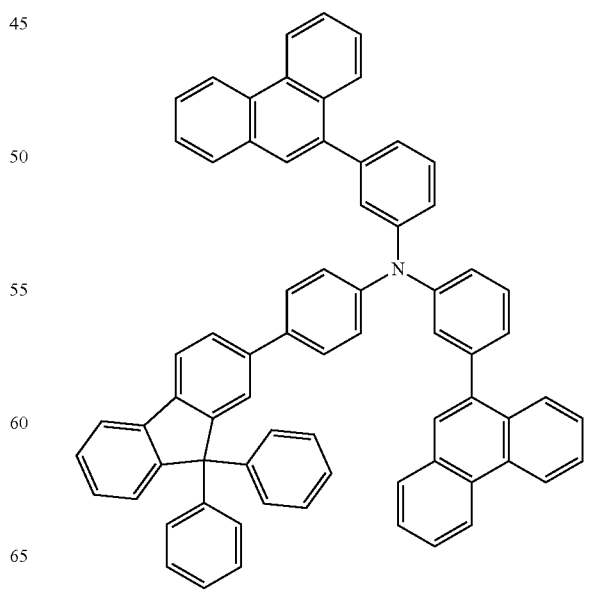

127
-continued
128
-continued
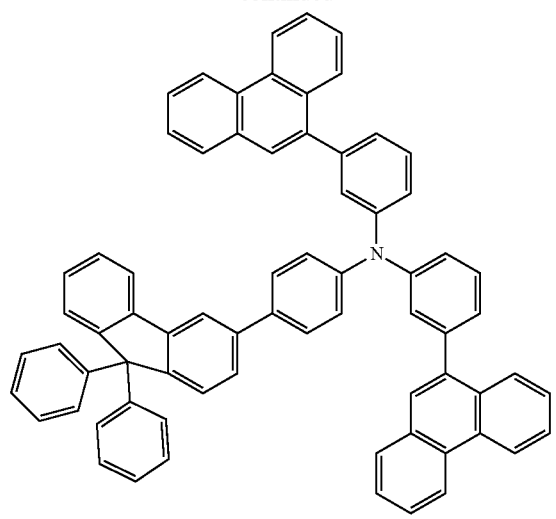
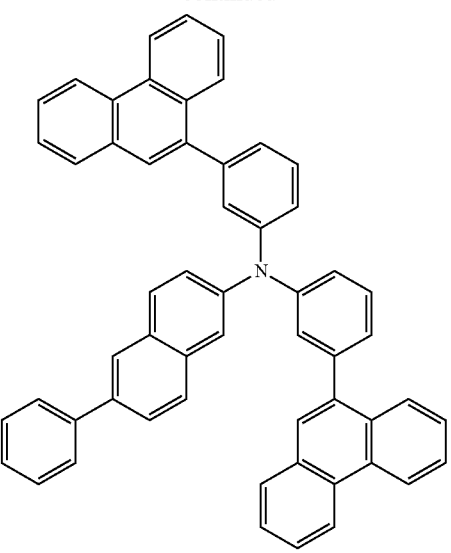
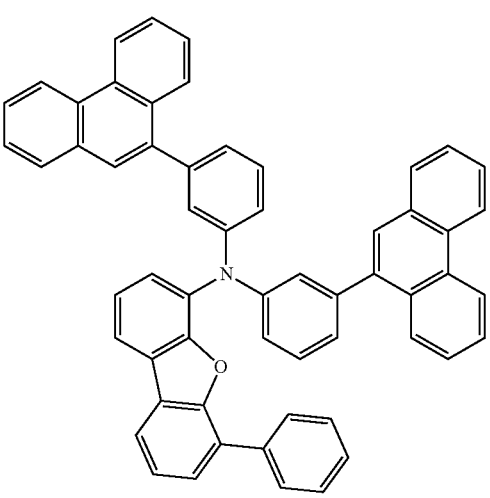

-continued
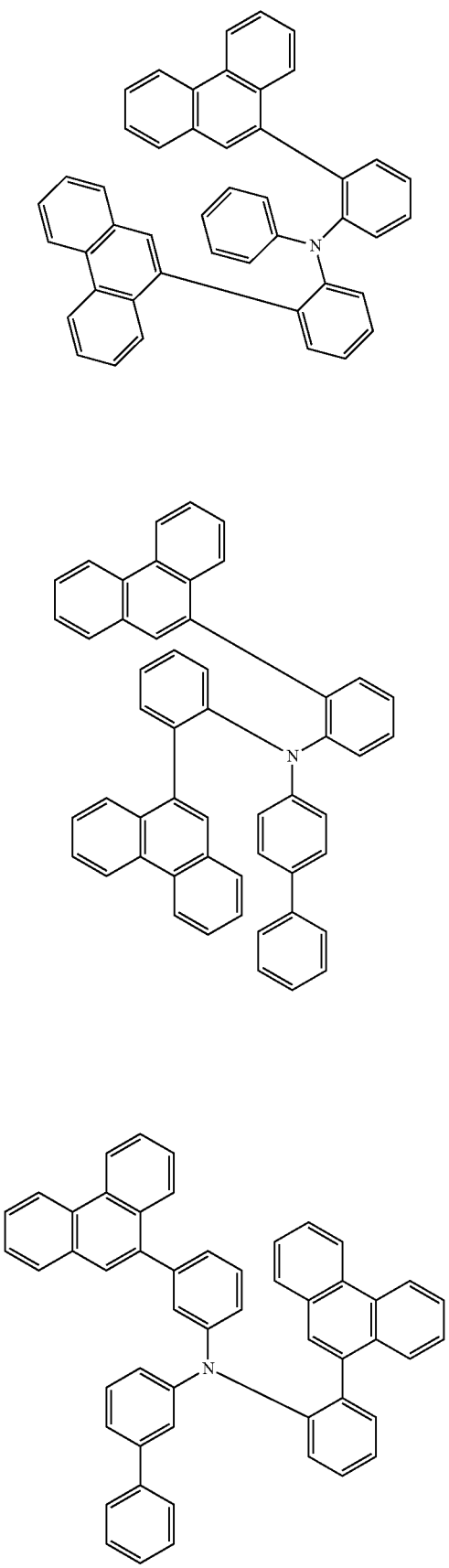
-continued
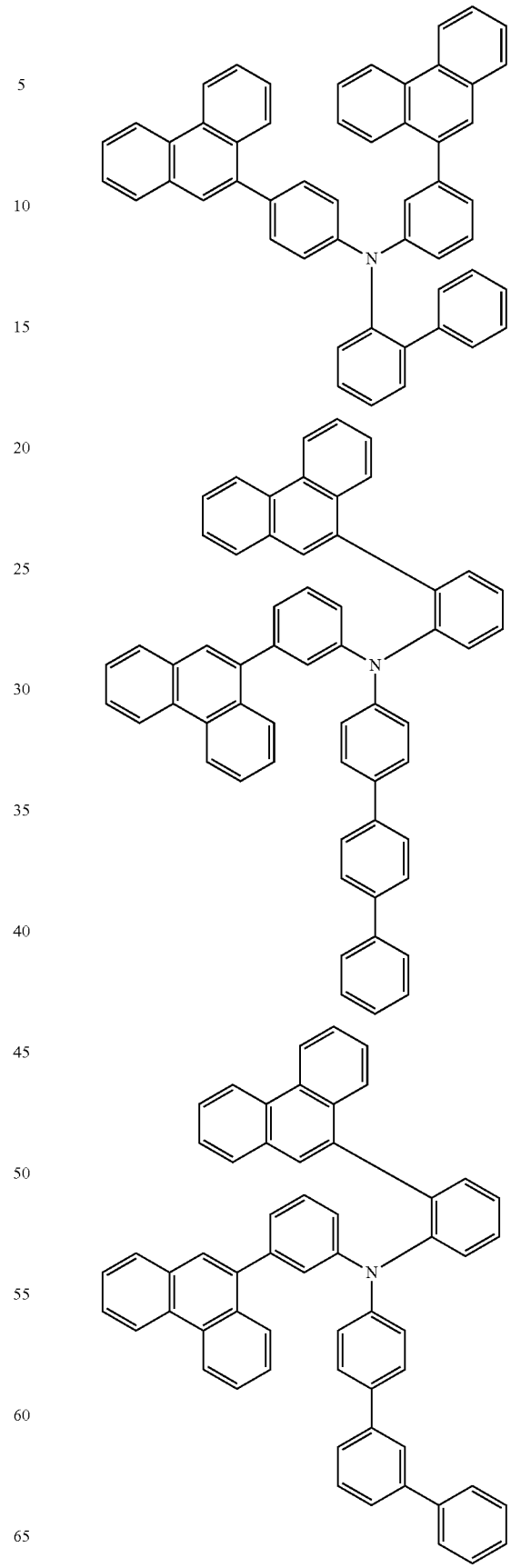

131
-continued
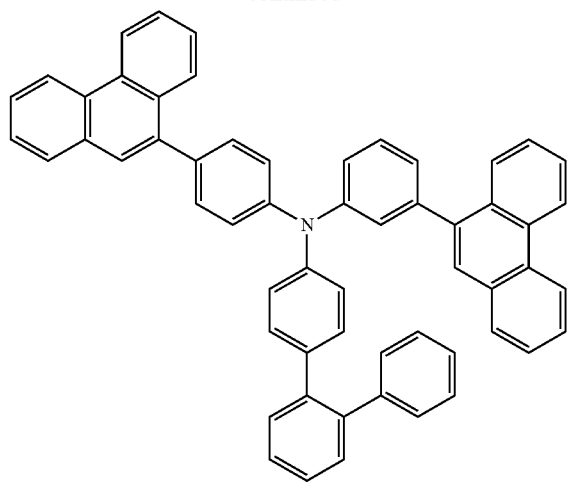
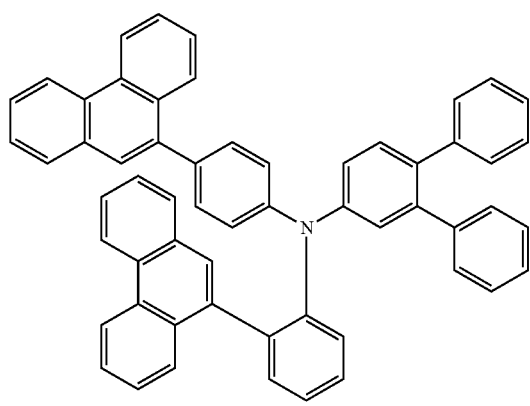
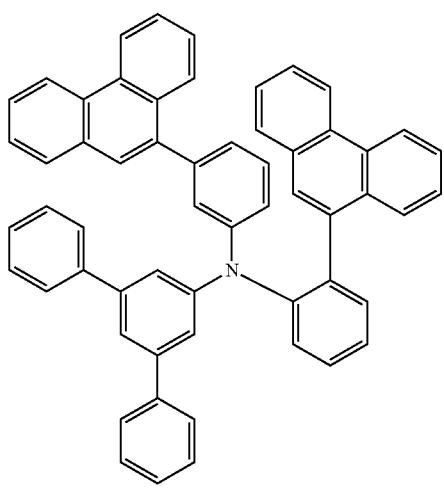
132
-continued
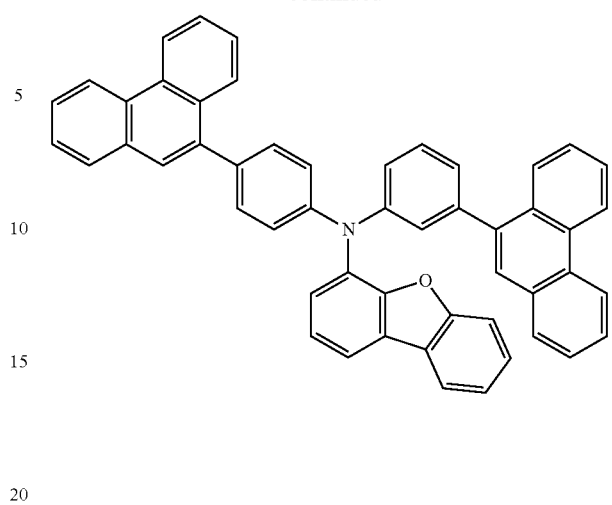
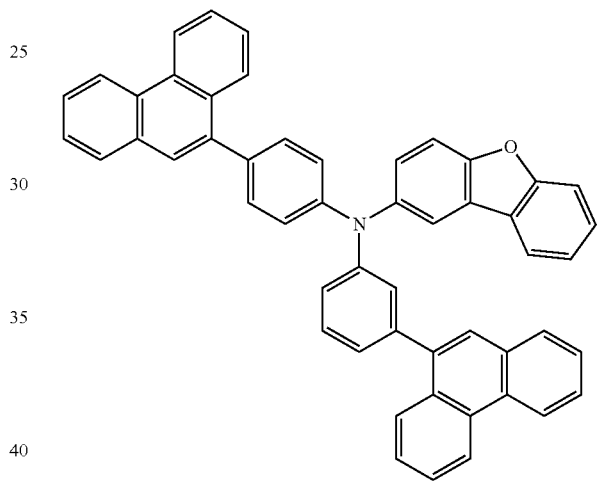
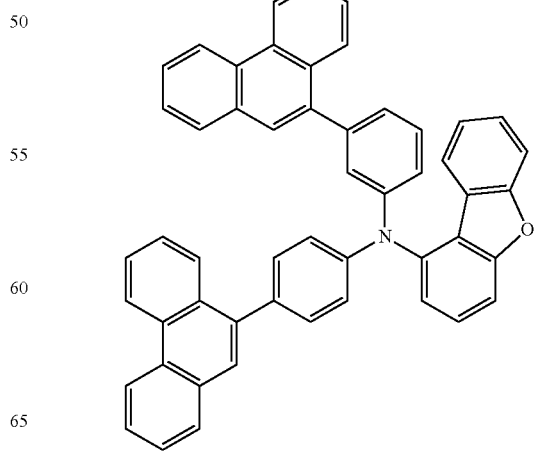

133
-continued
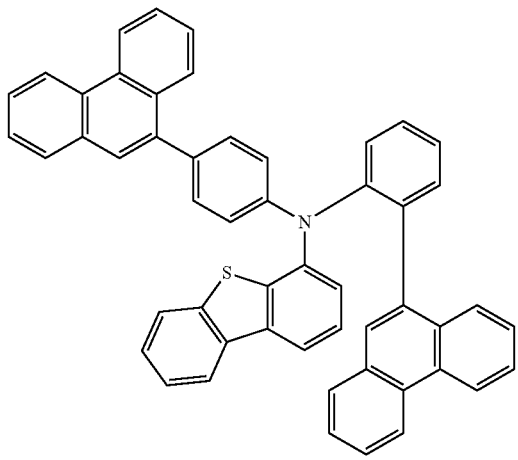
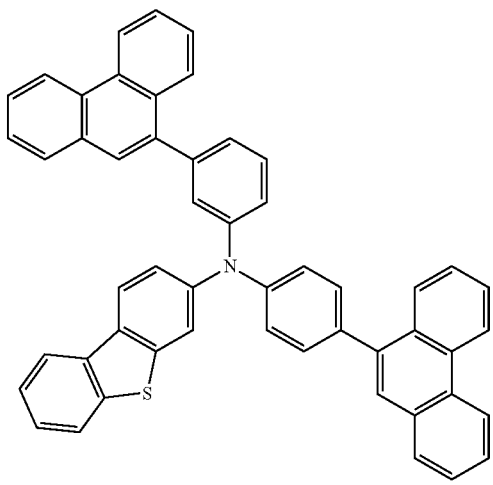
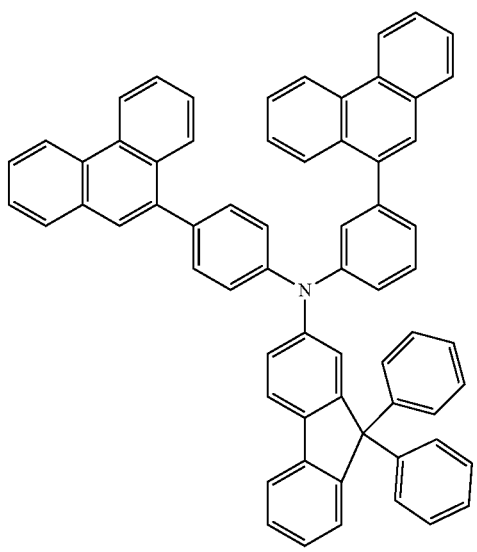
134
-continued
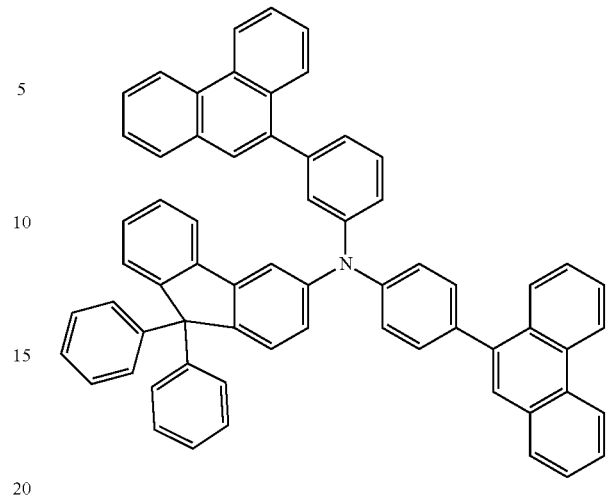
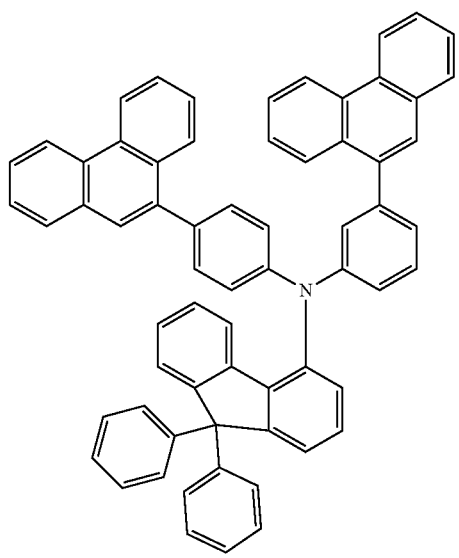
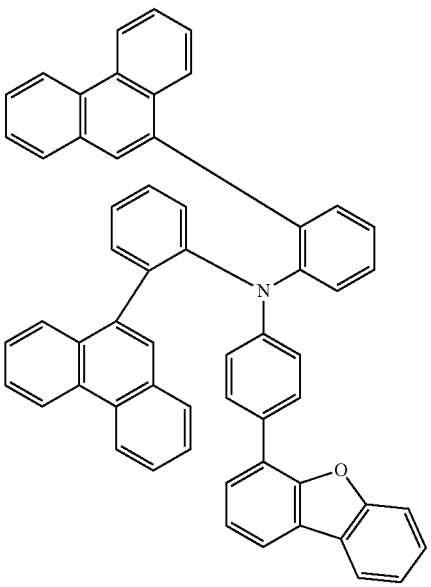

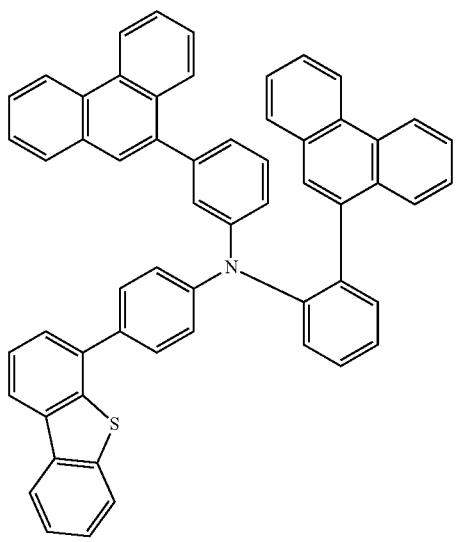
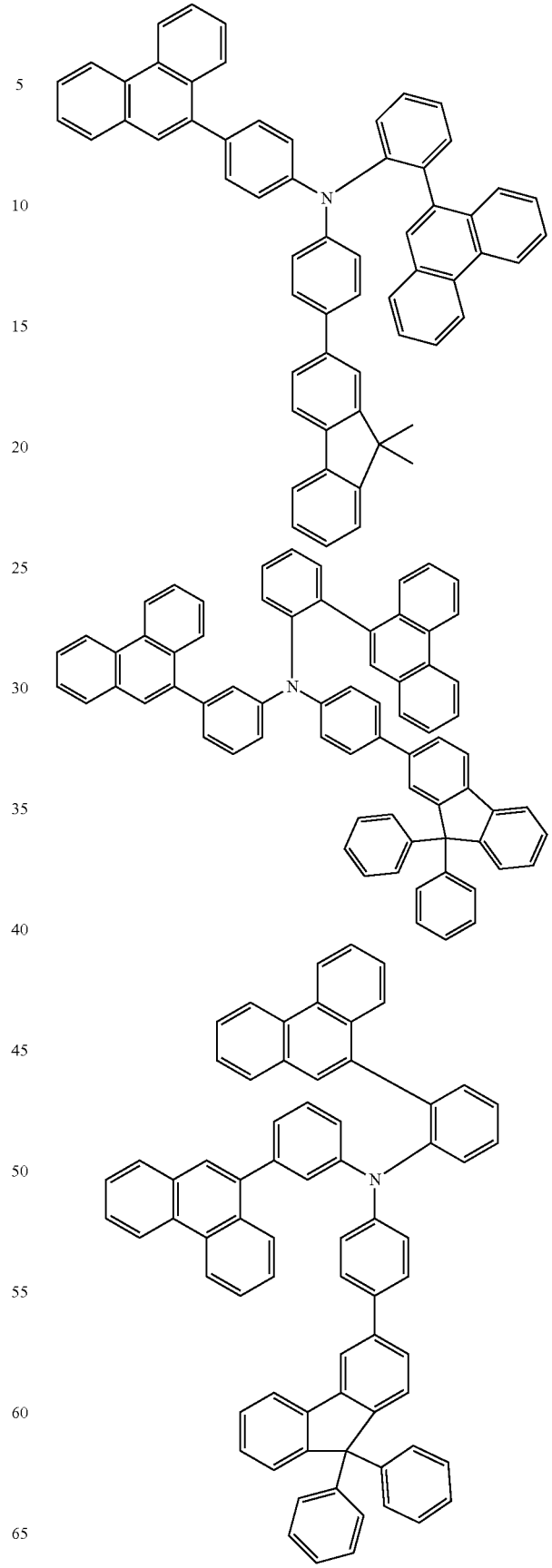

137
-continued
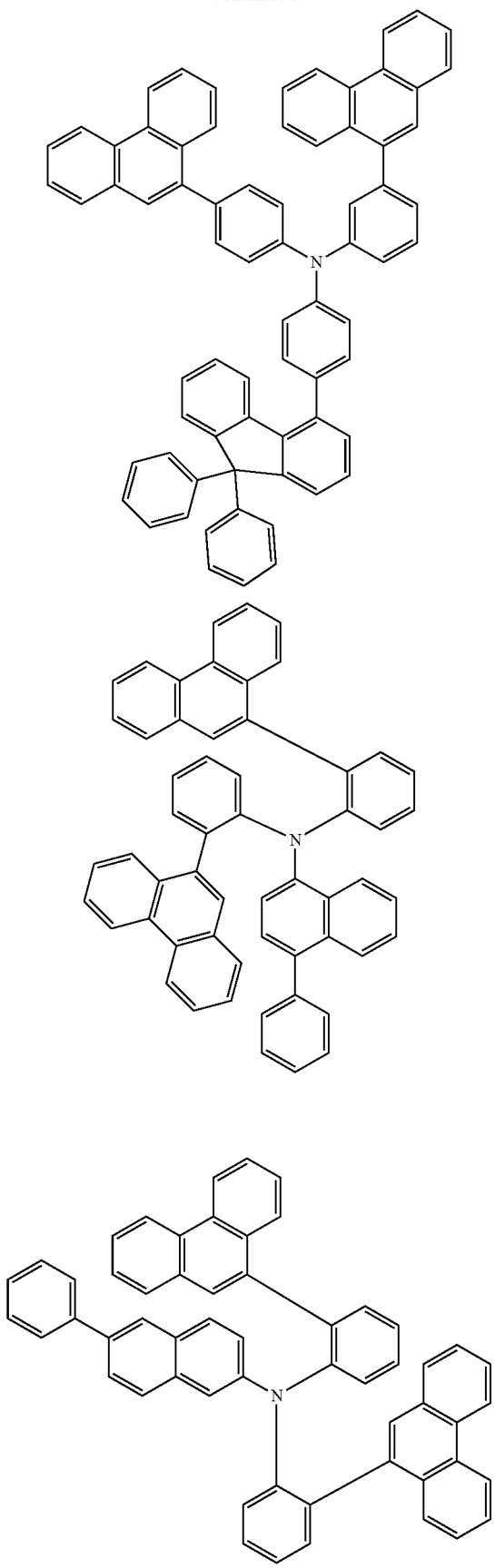
138
-continued
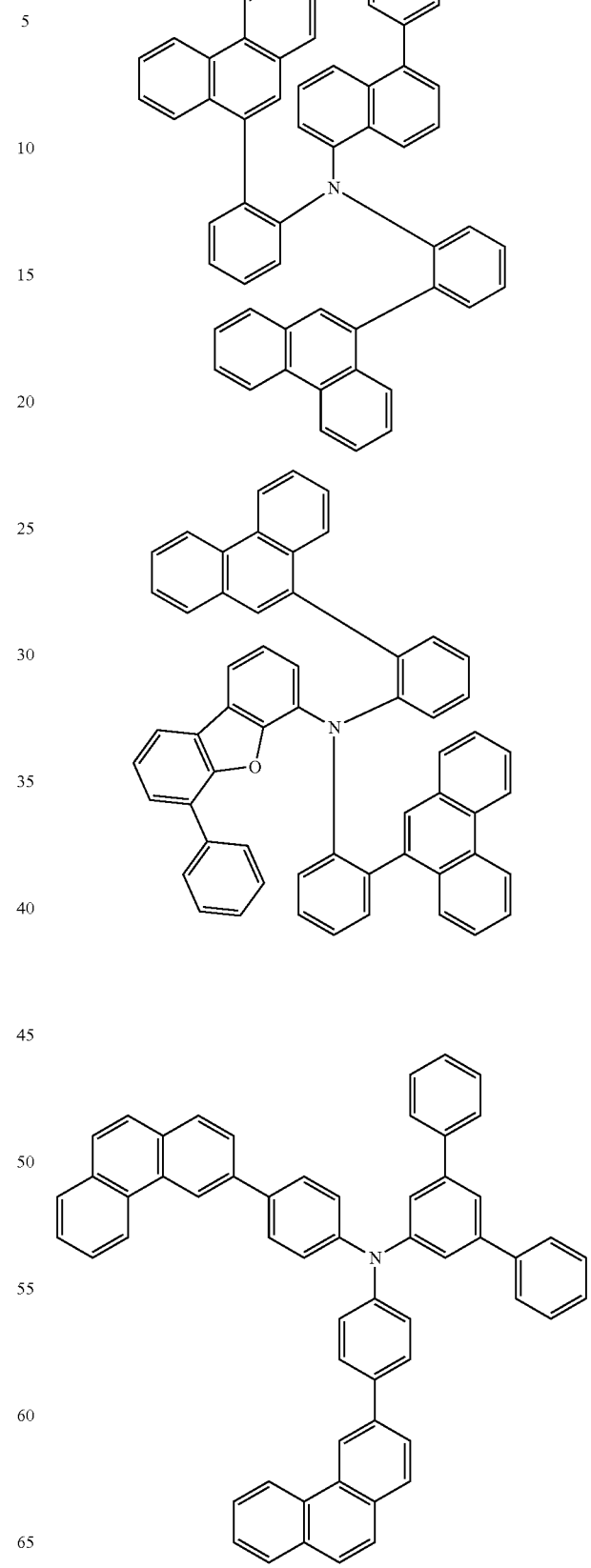

139
-continued
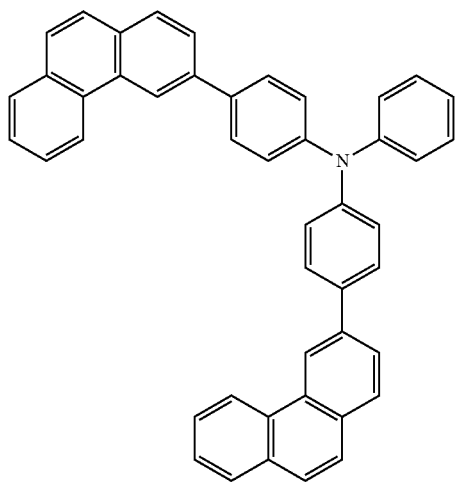
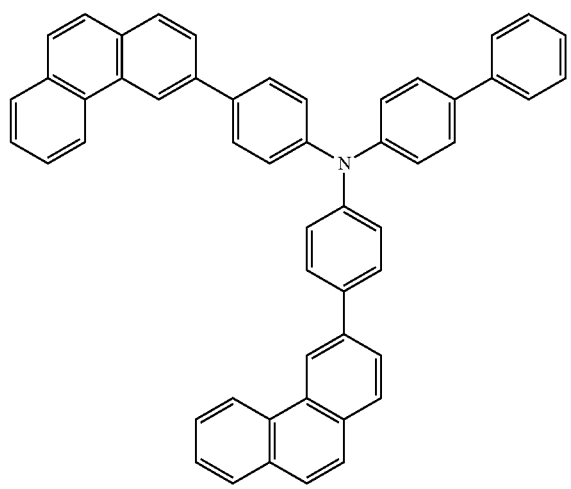
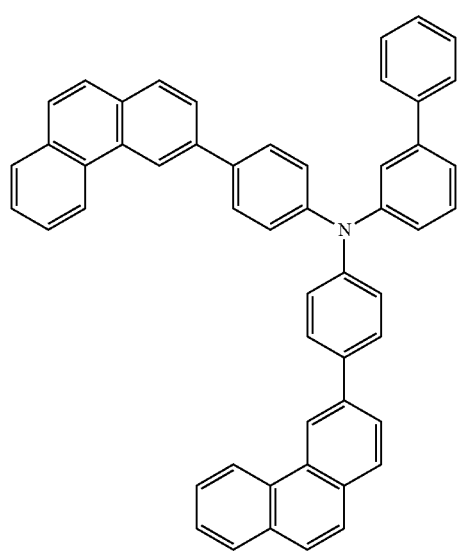
140
-continued
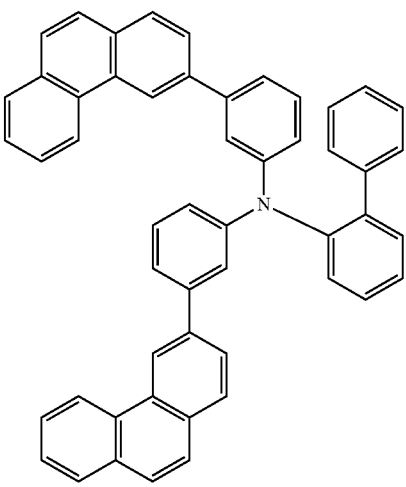
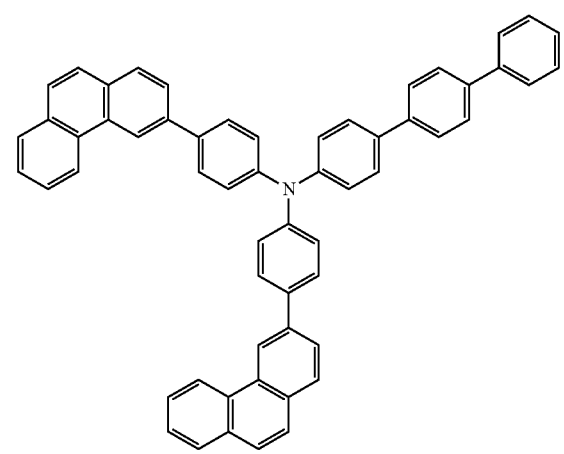
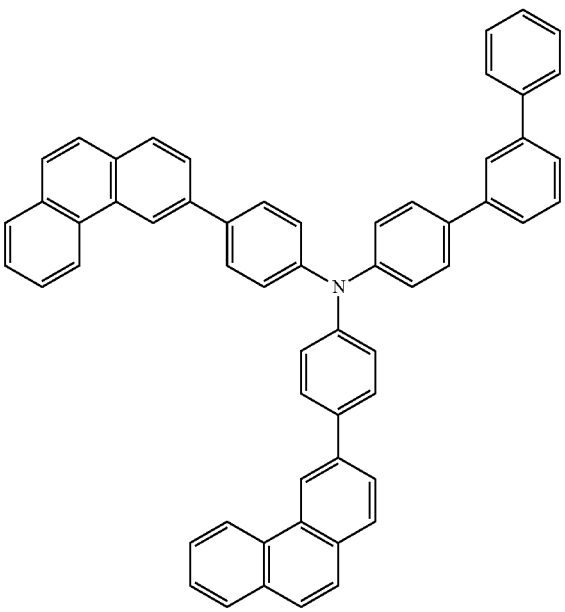

141
-continued
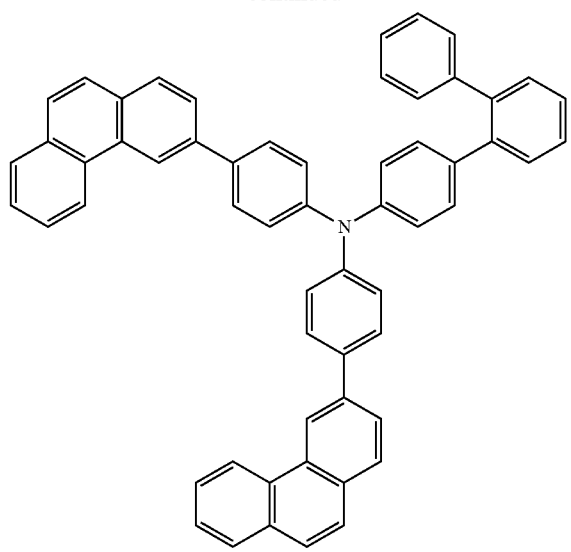
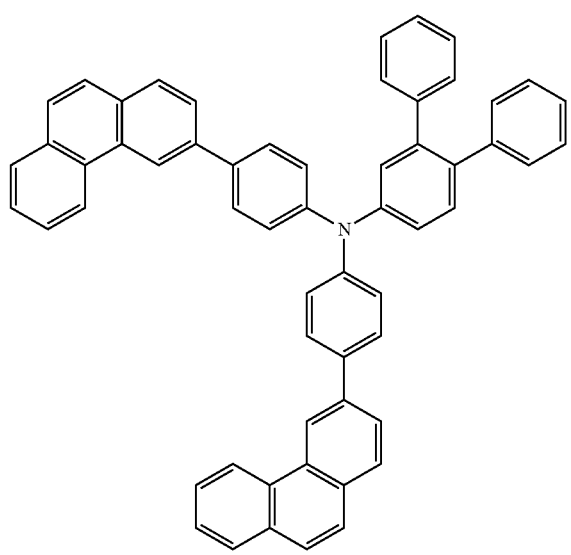
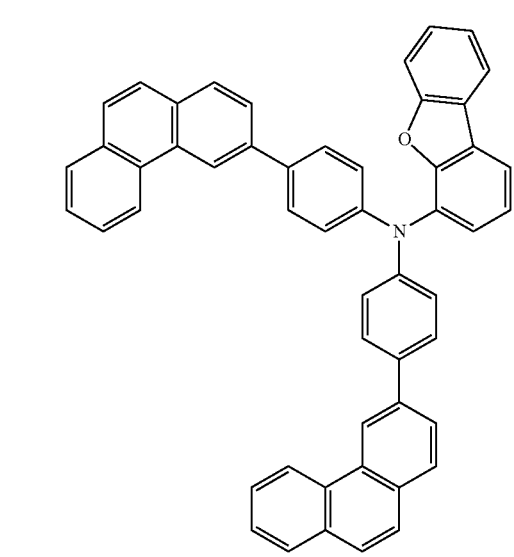
142
-continued
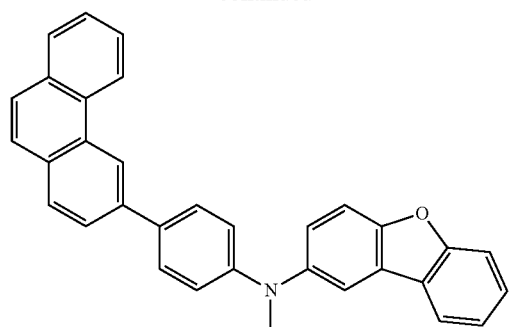
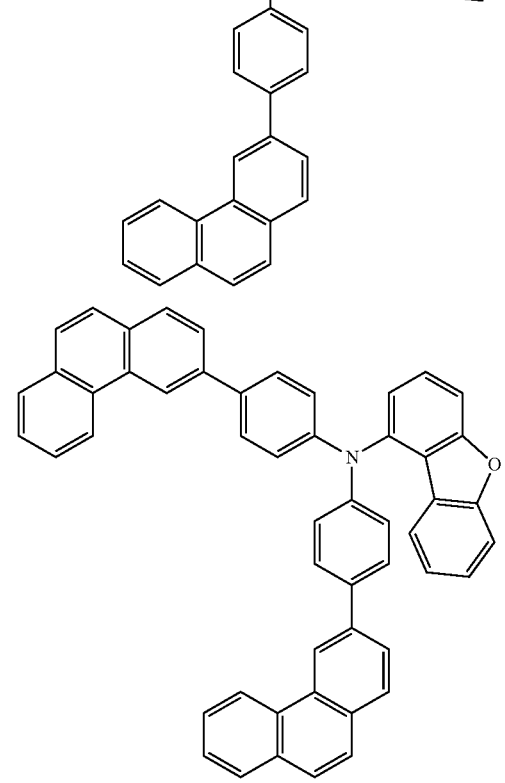
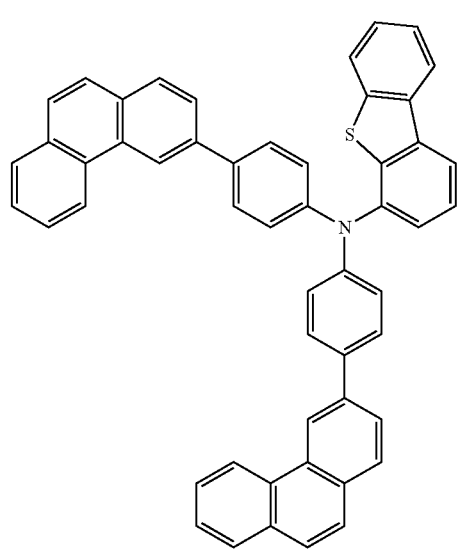

143
-continued
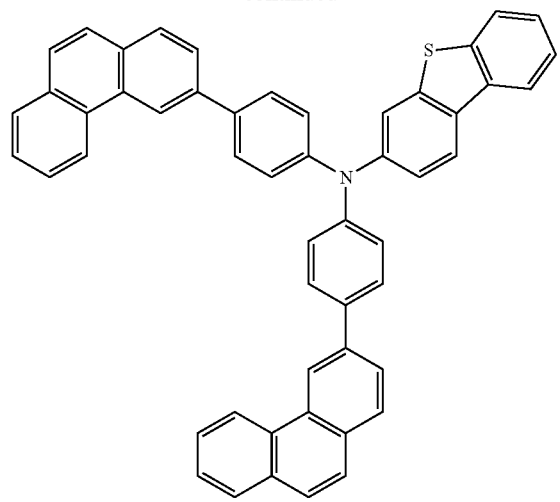
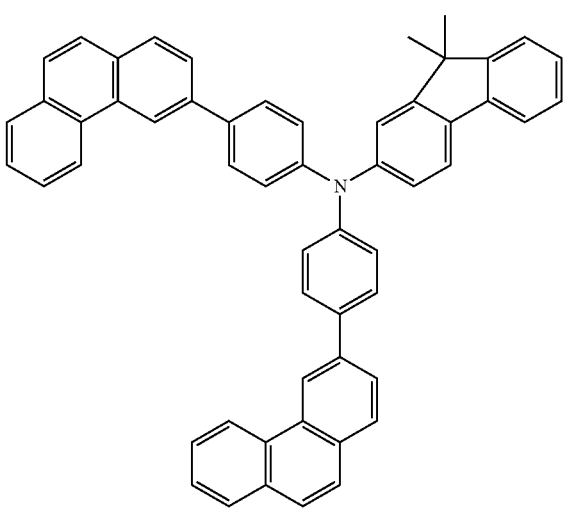
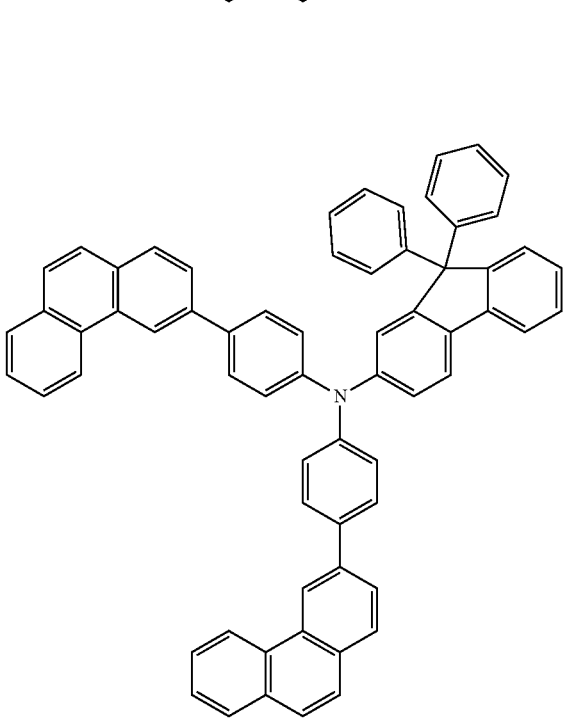
144
-continued
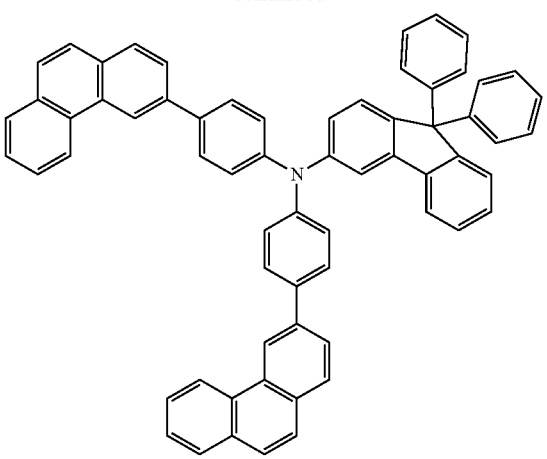
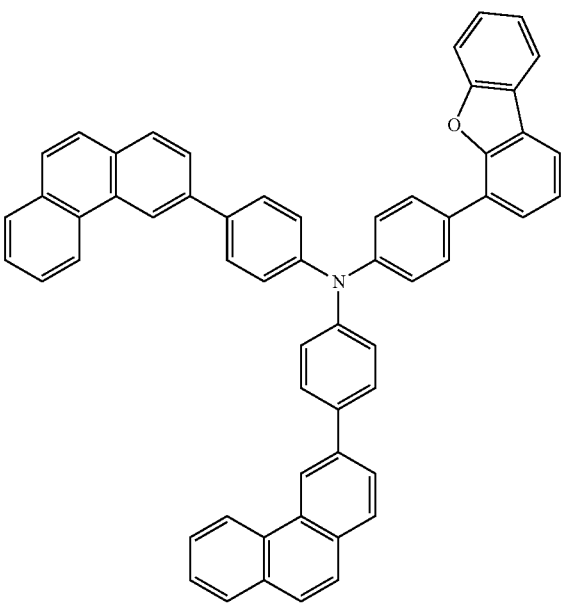

145
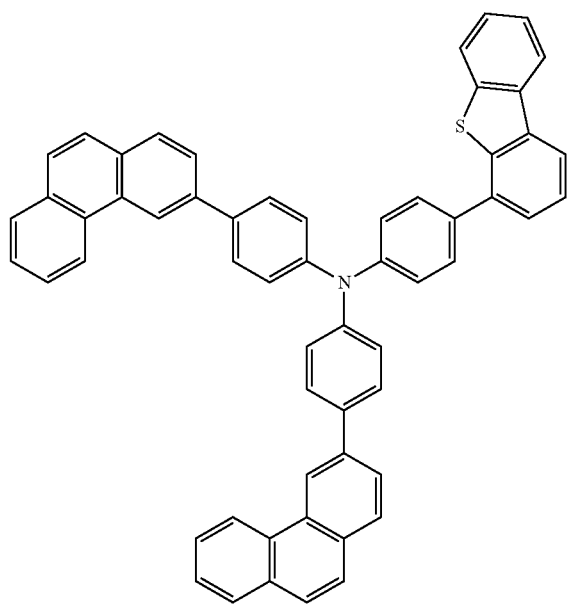
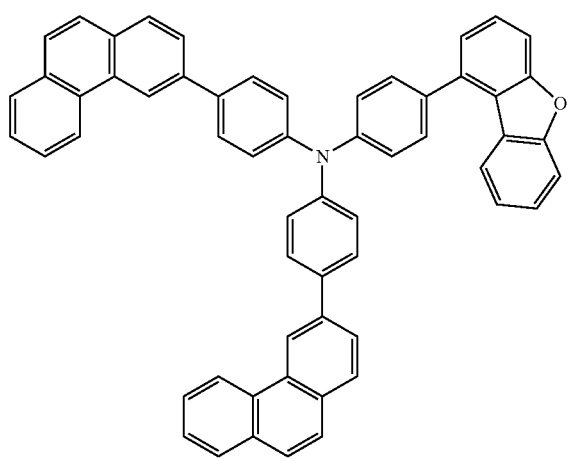
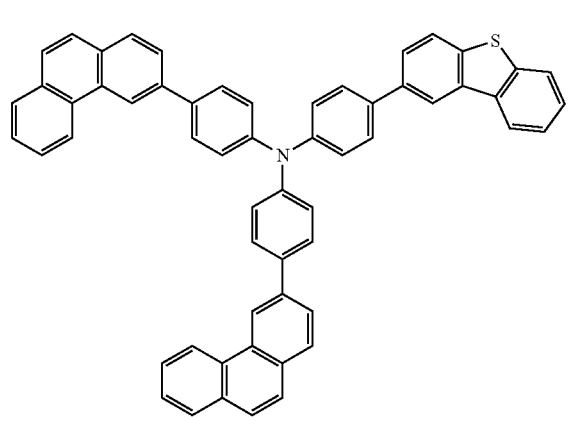
146
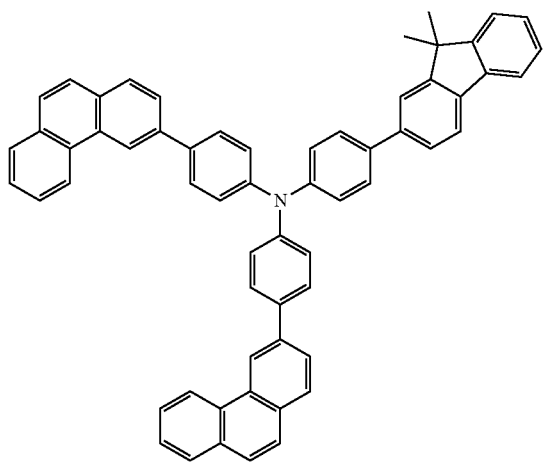
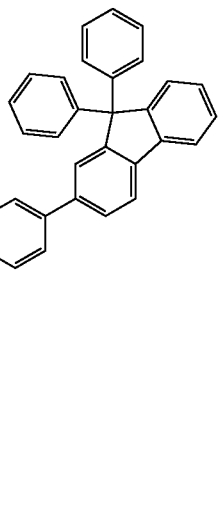
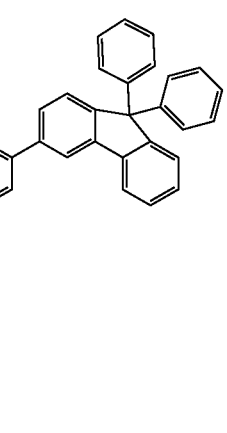

147
-continued
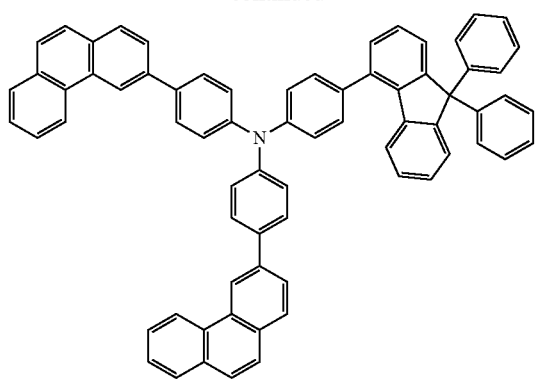
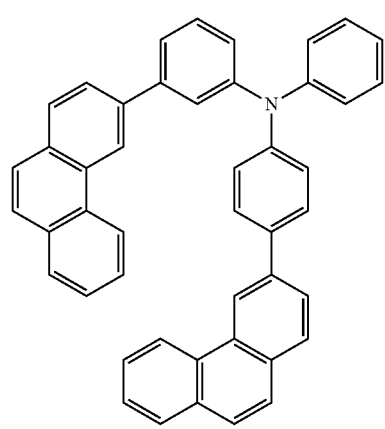
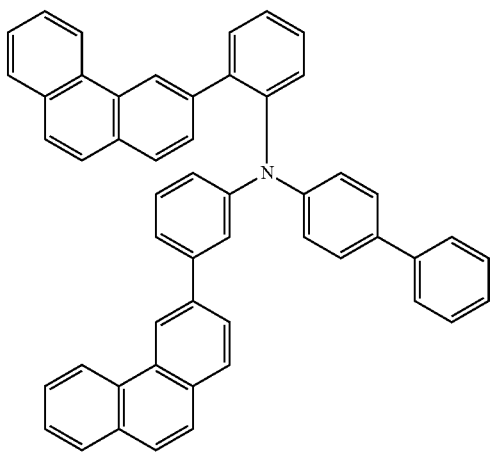
148
-continued
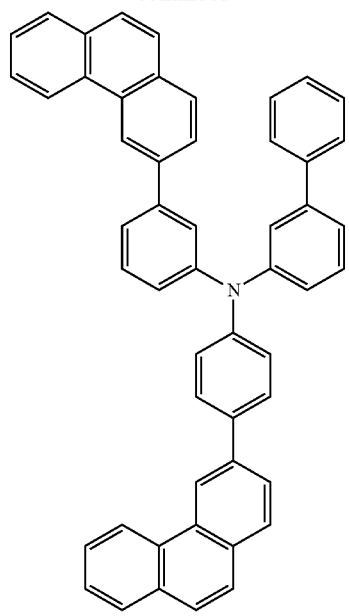
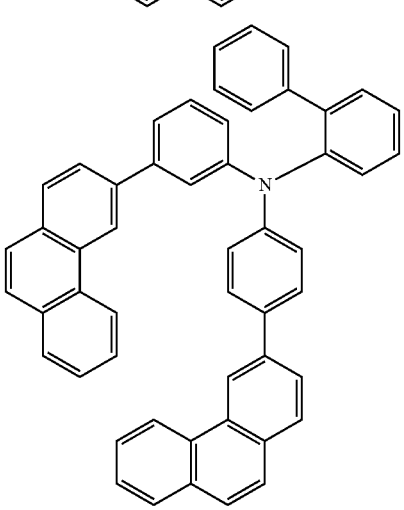
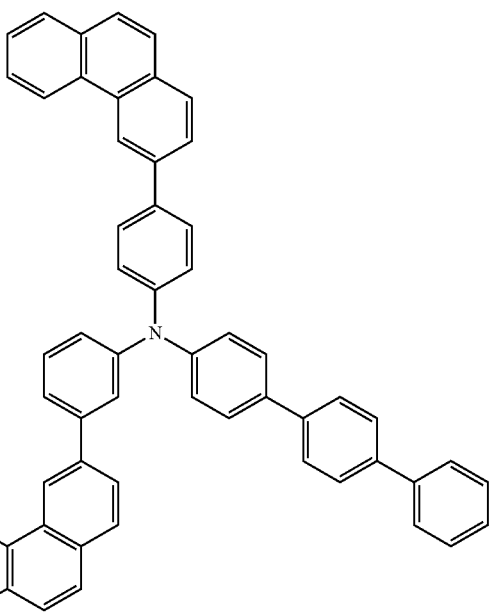

149
-continued
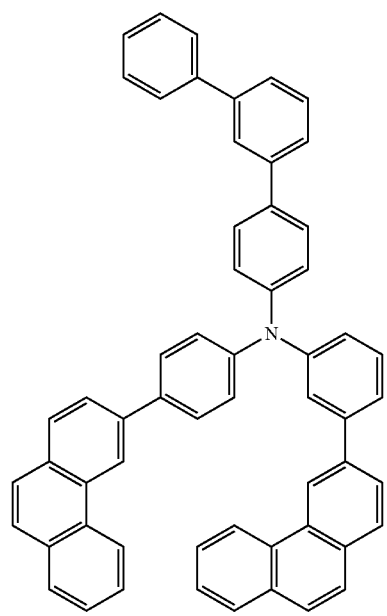
150
-continued
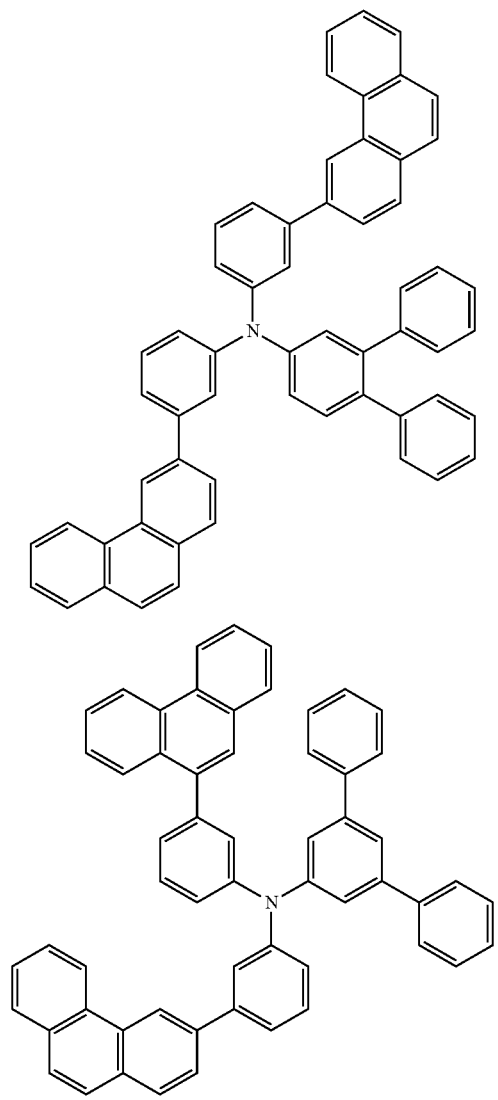
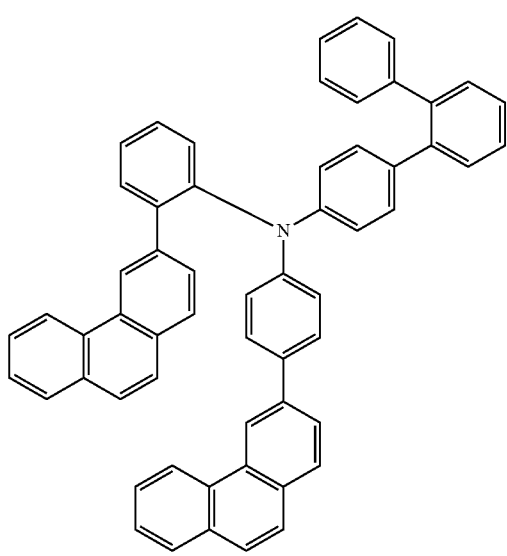
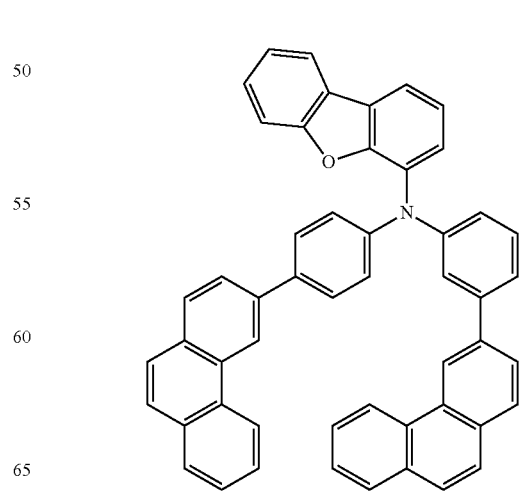

151
-continued
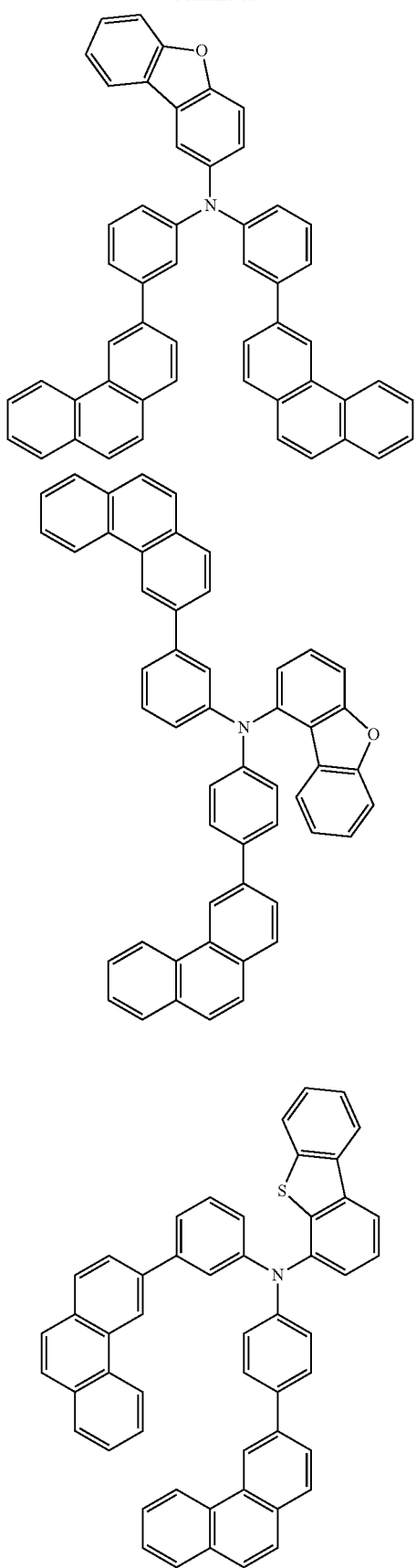
152
-continued
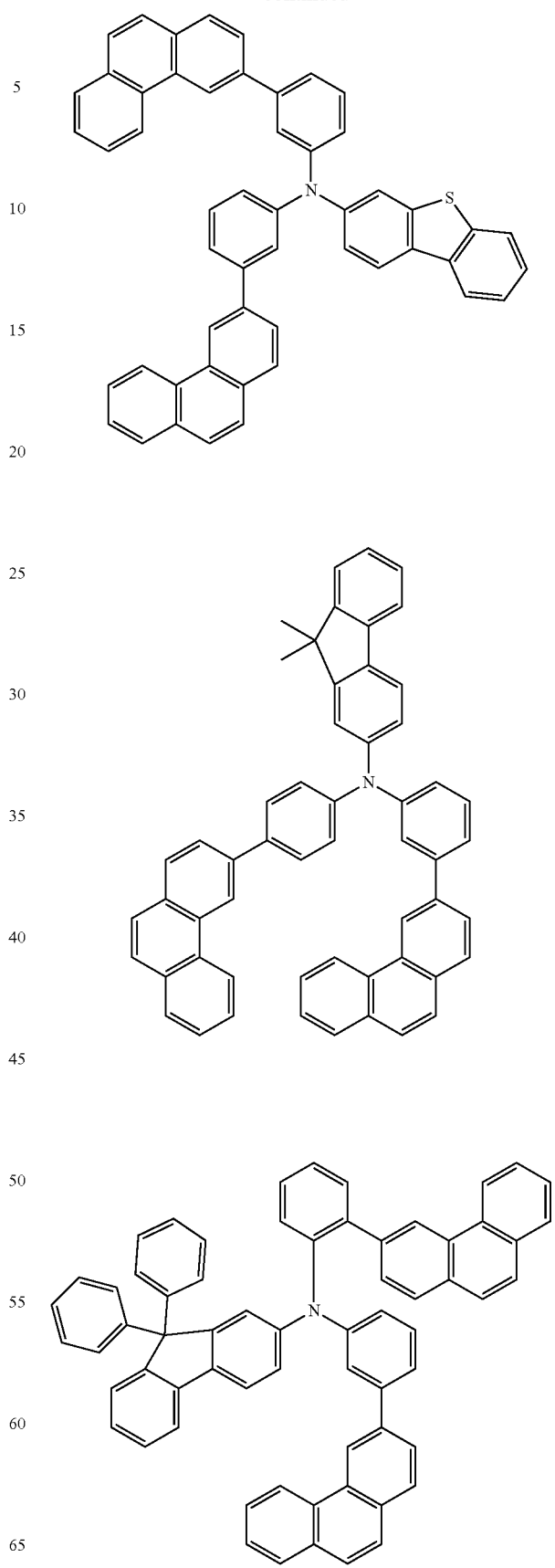

153
-continued
154
-continued
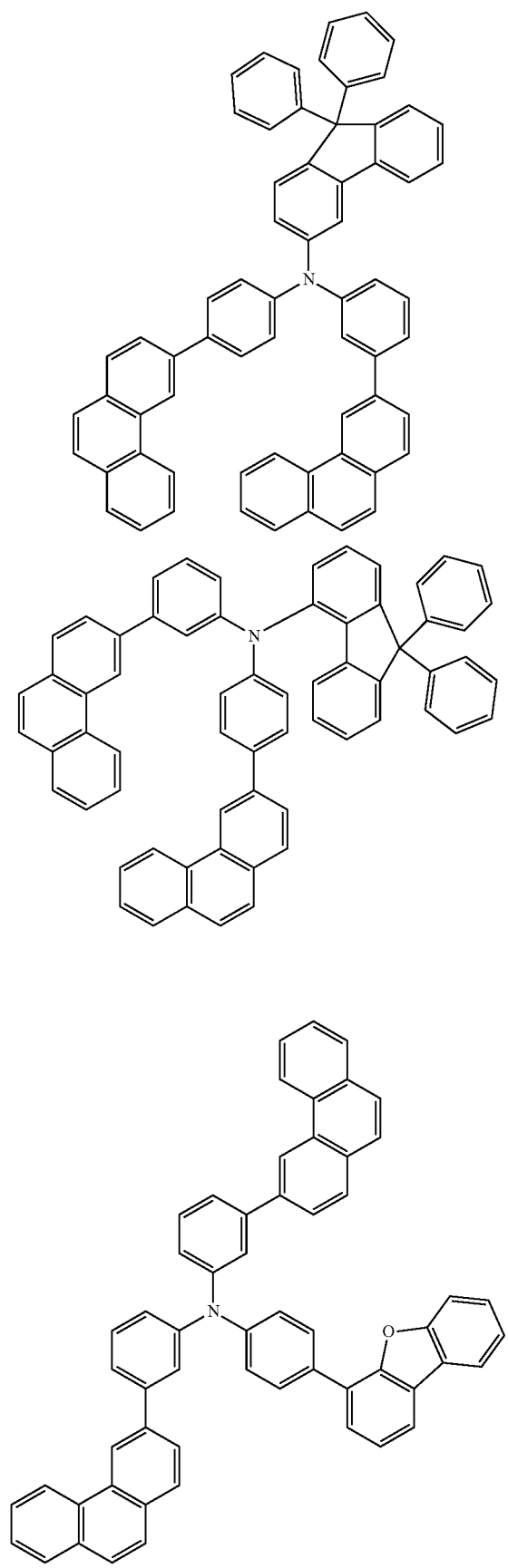
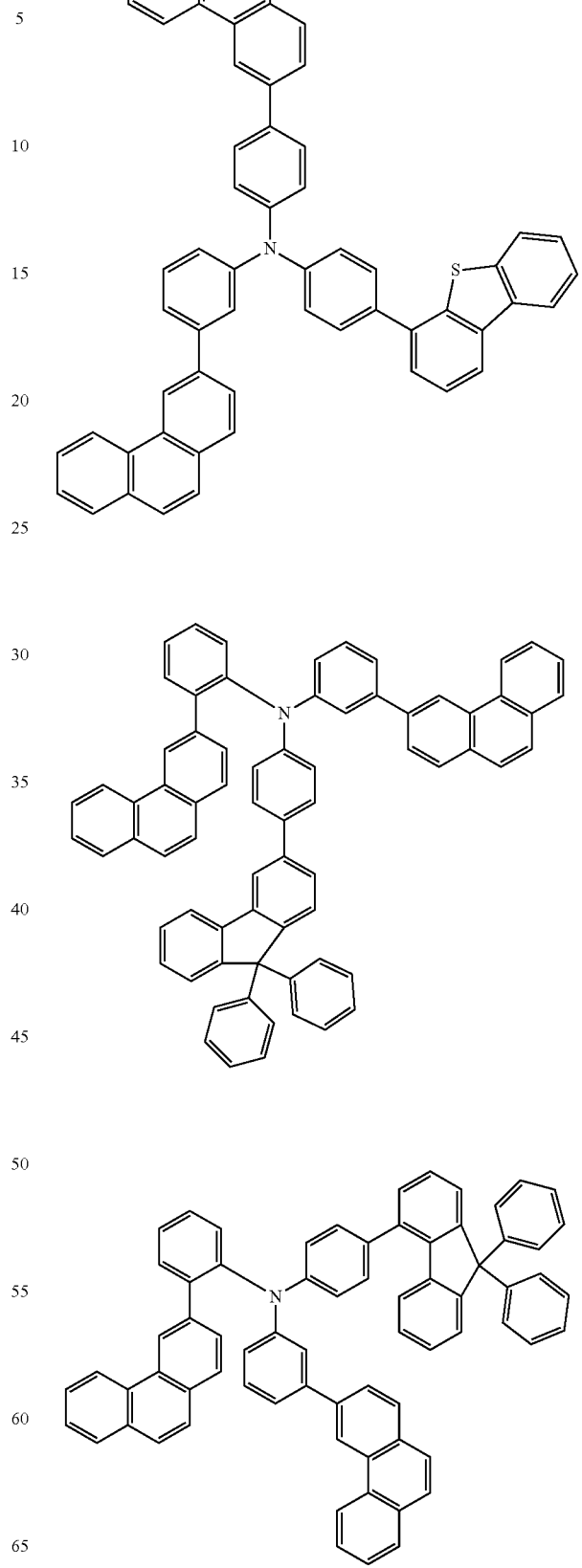

155
-continued
156
-continued
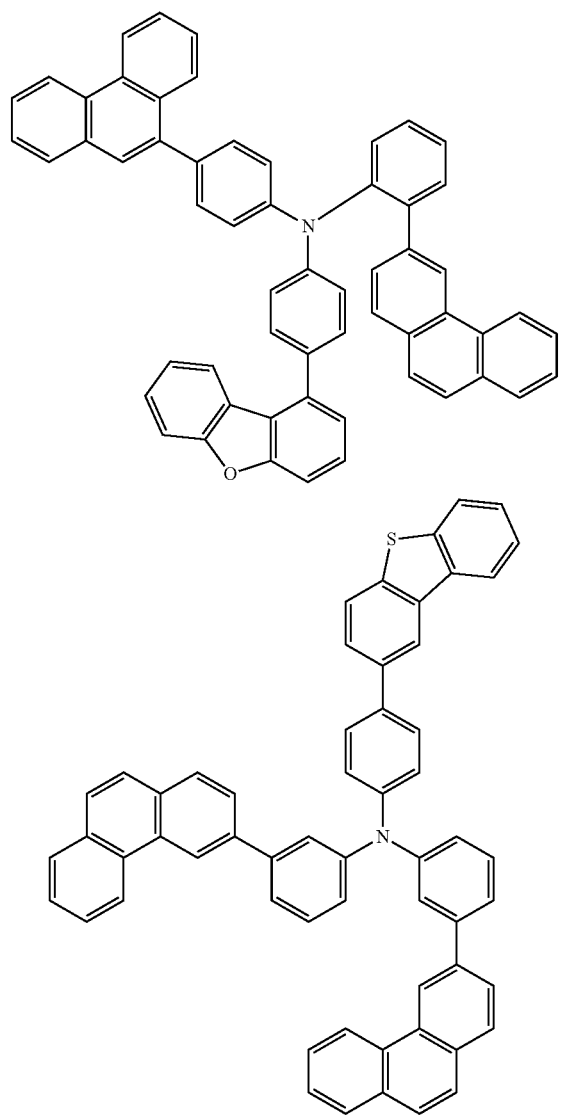
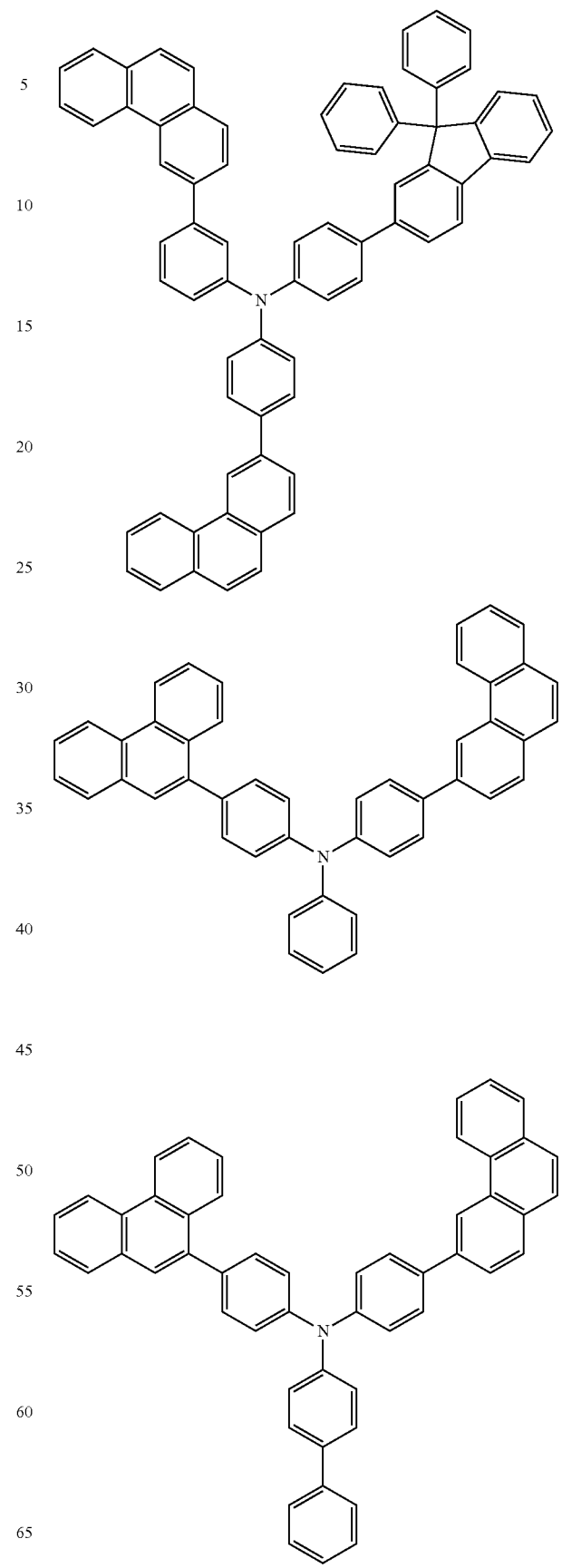

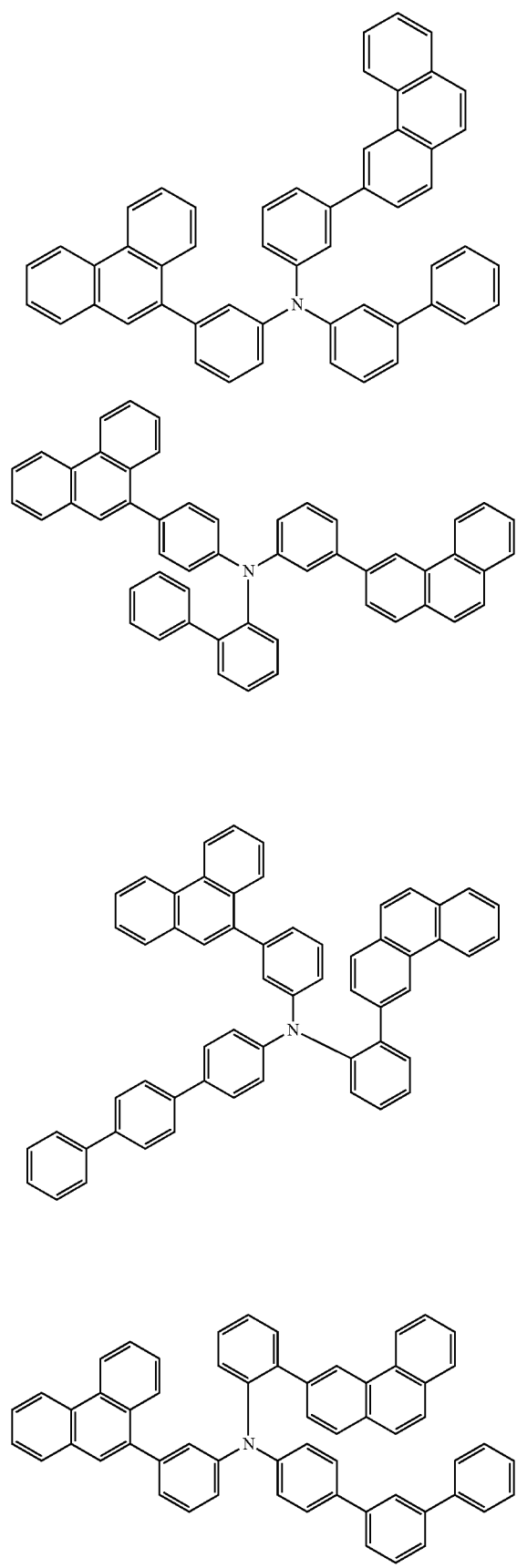
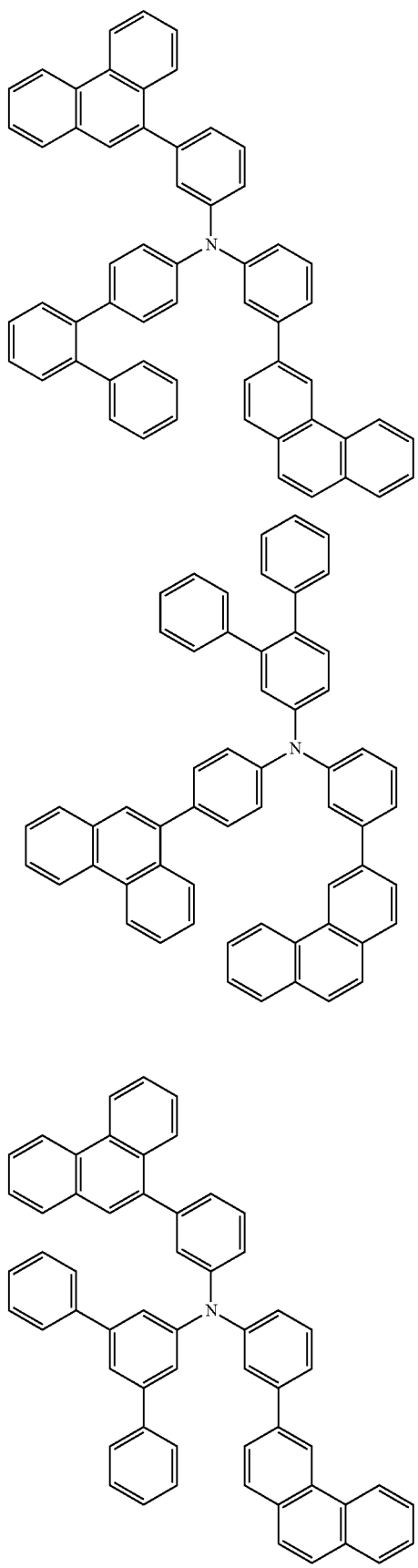

159
-continued
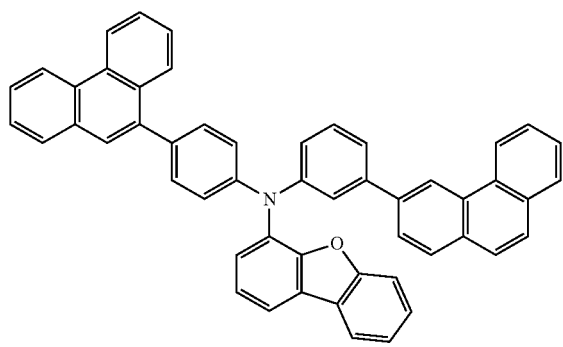
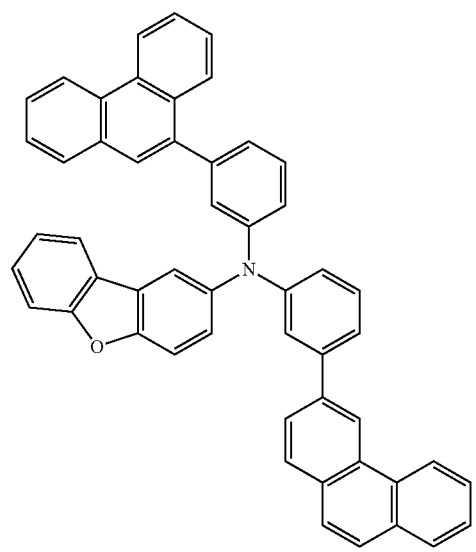
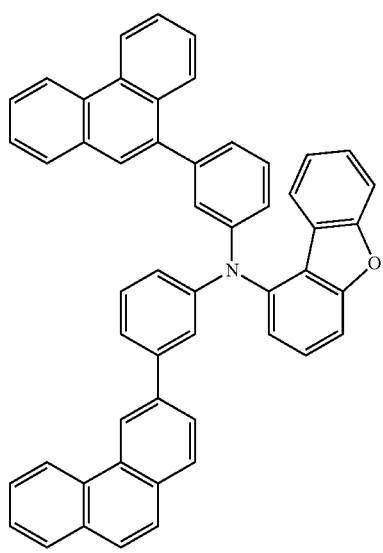
160
-continued
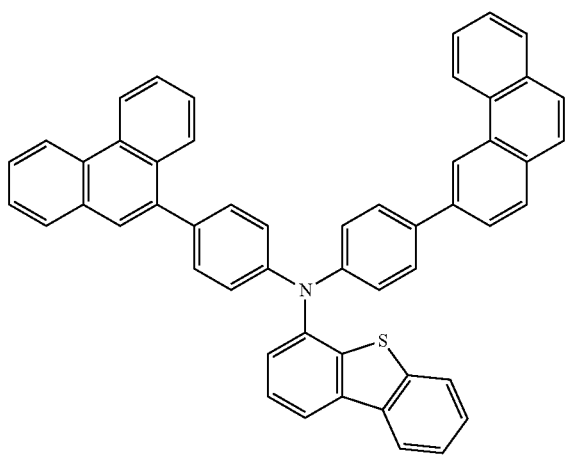
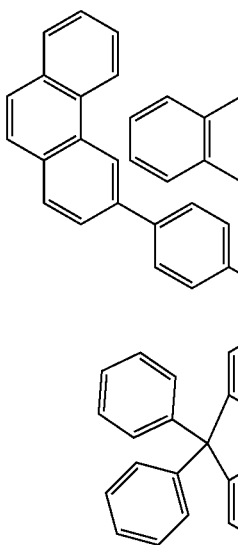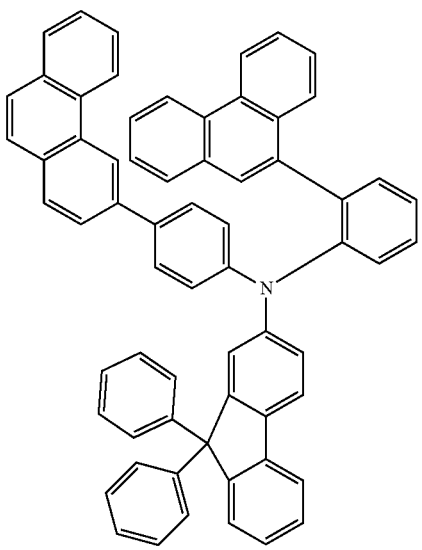

161
-continued
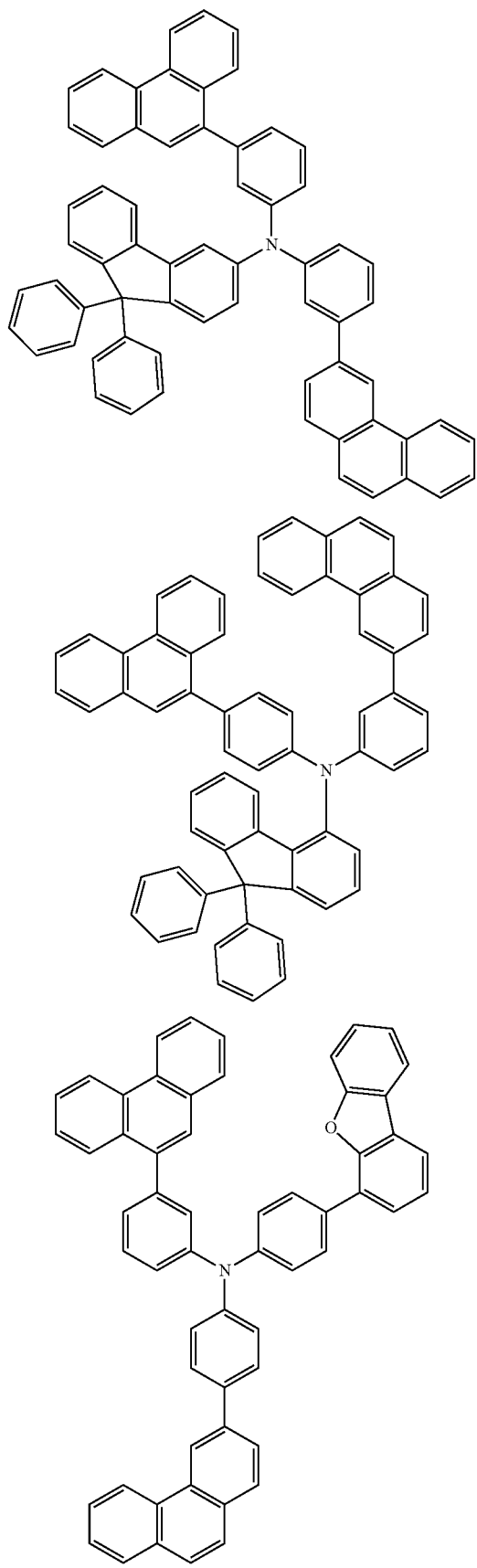
162
-continued
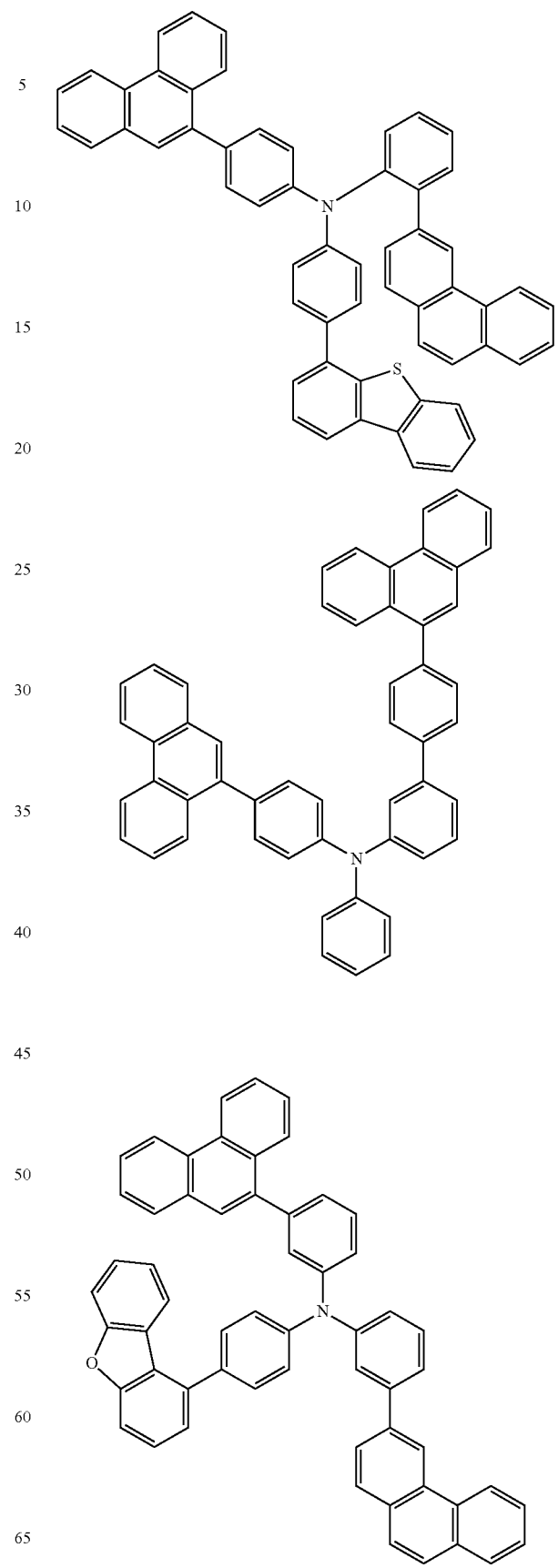

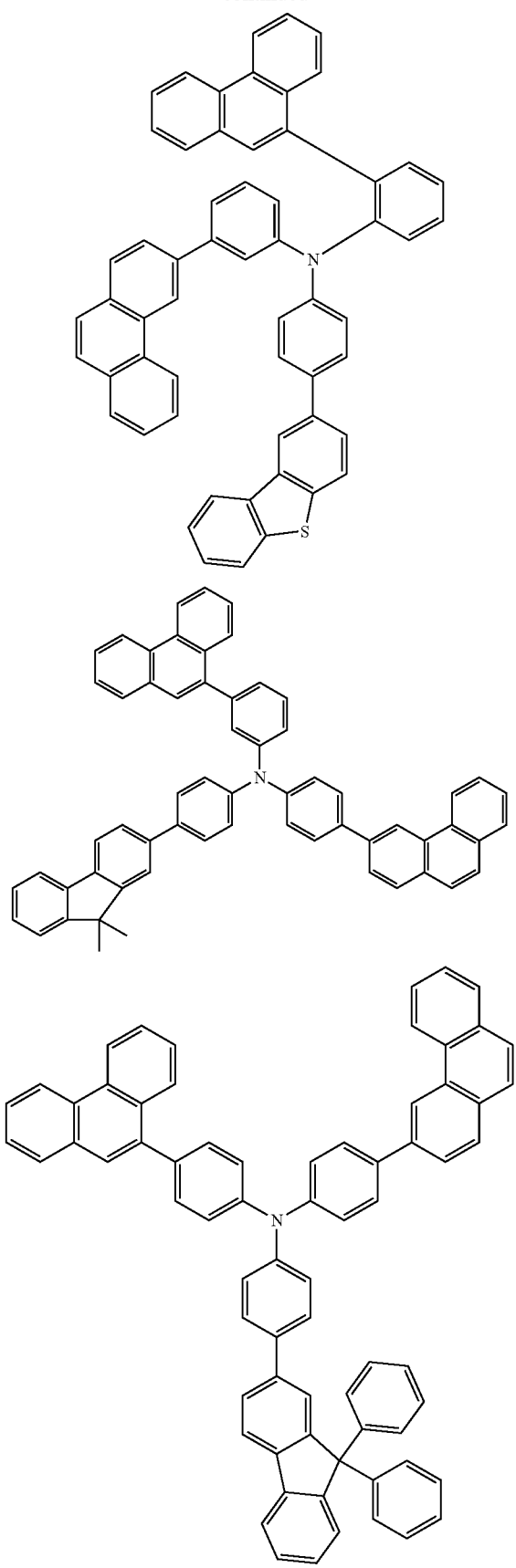
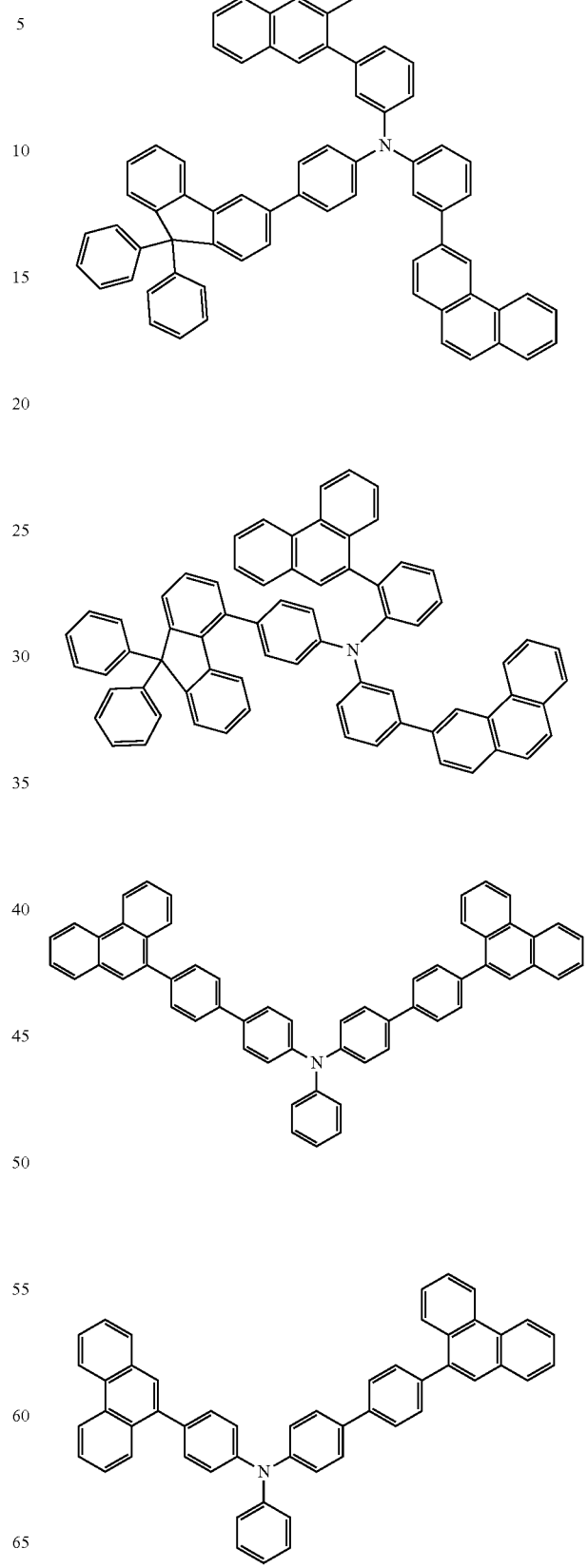

165
-continued
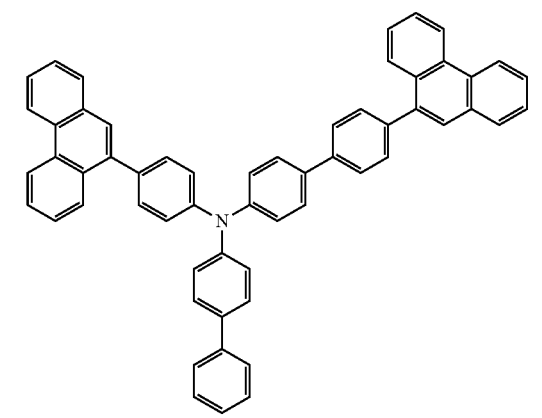
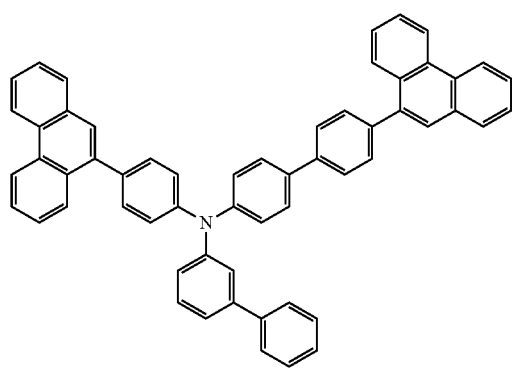
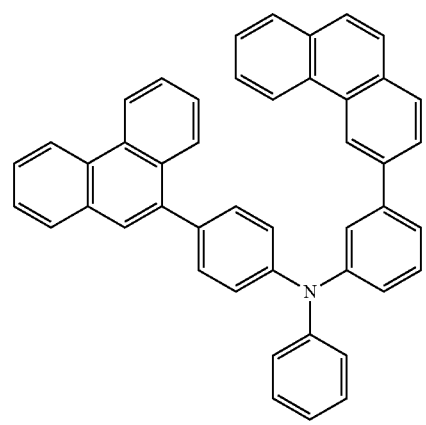
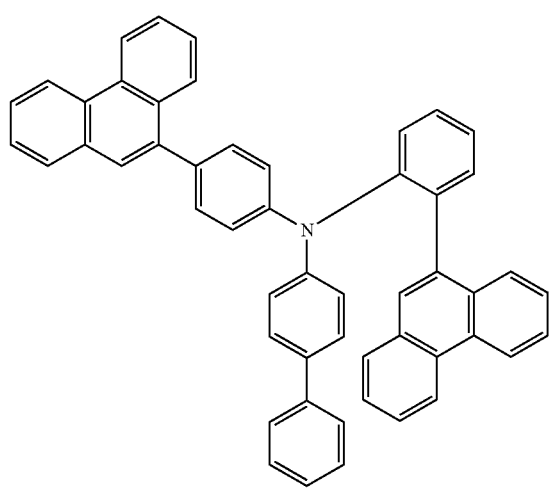
166
-continued
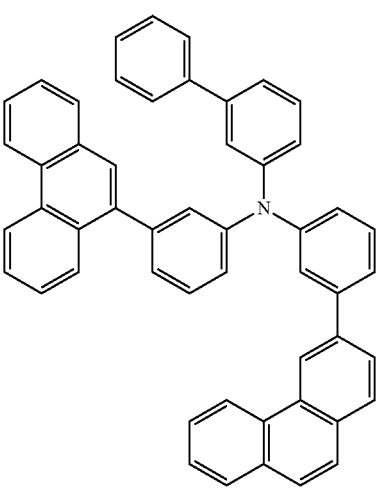
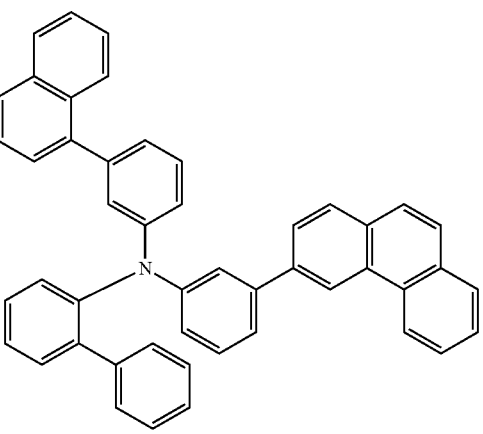
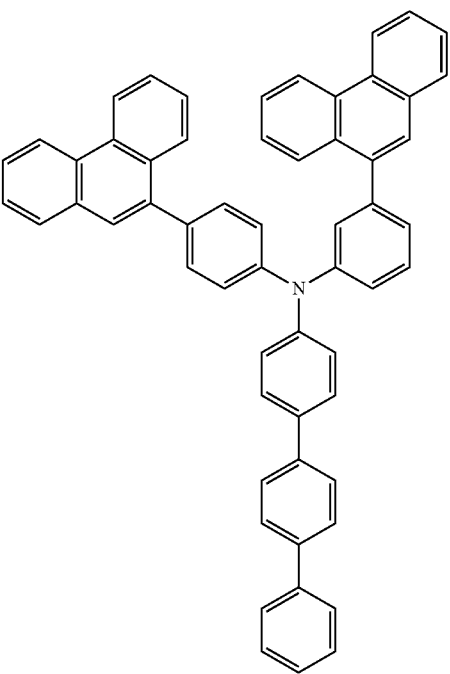

167
-continued
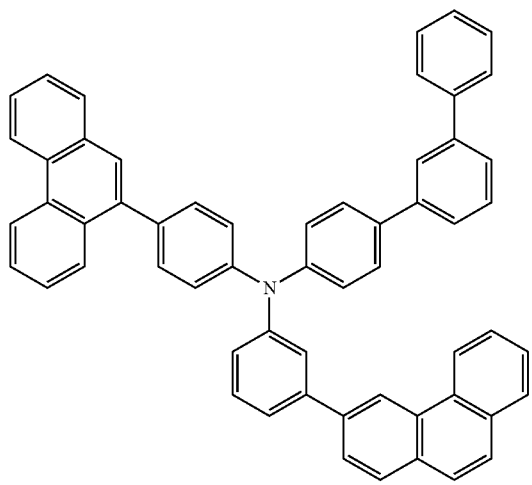
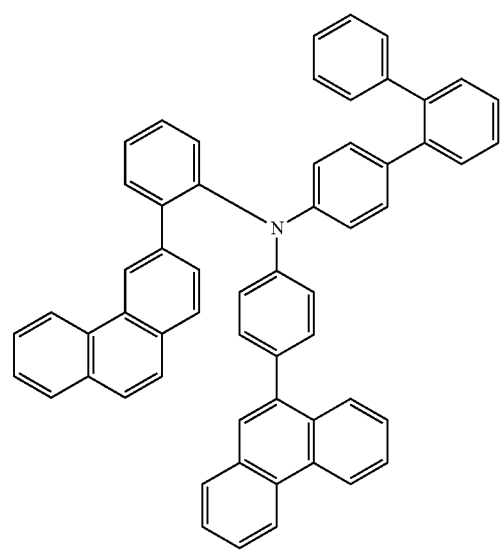
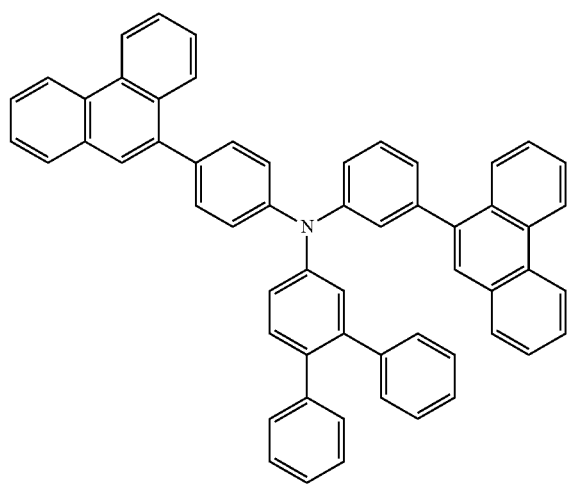
168
-continued
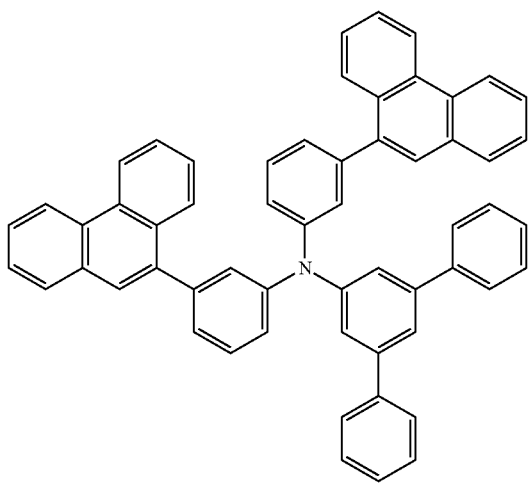
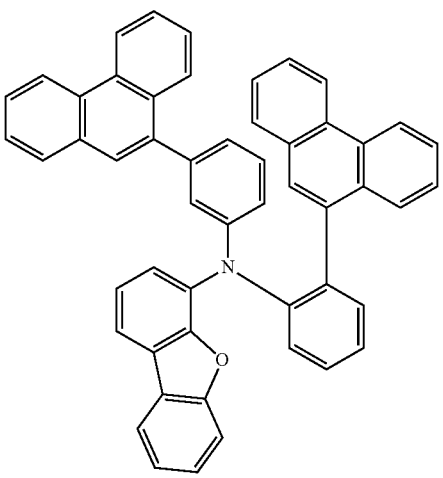
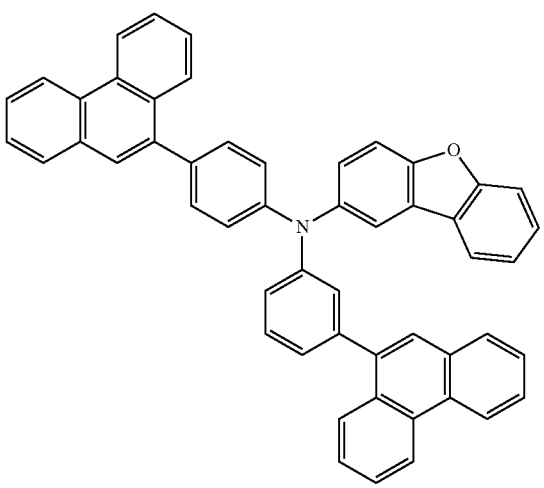

169
-continued
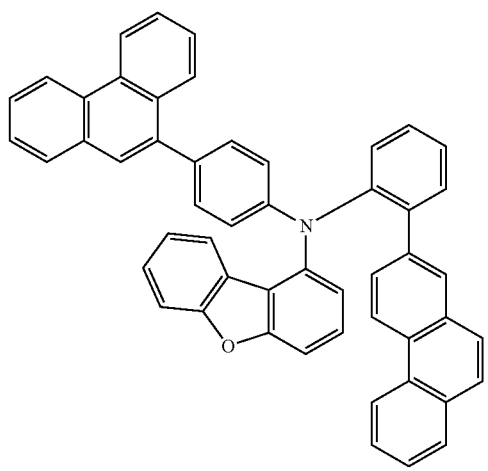
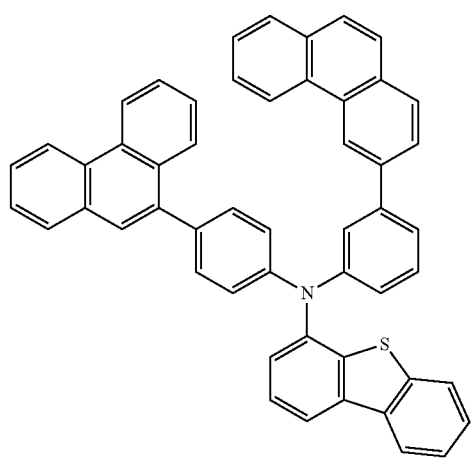
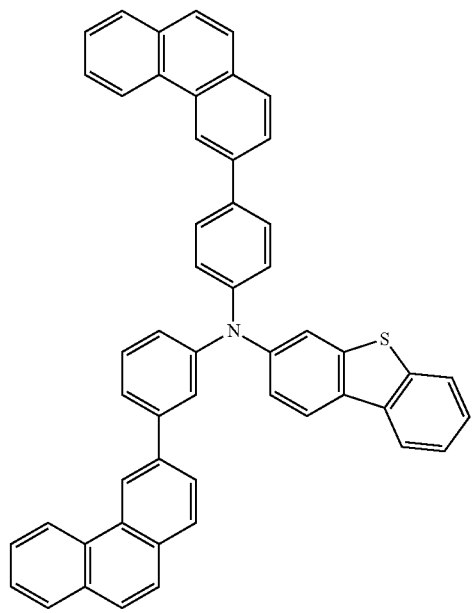
170
-continued
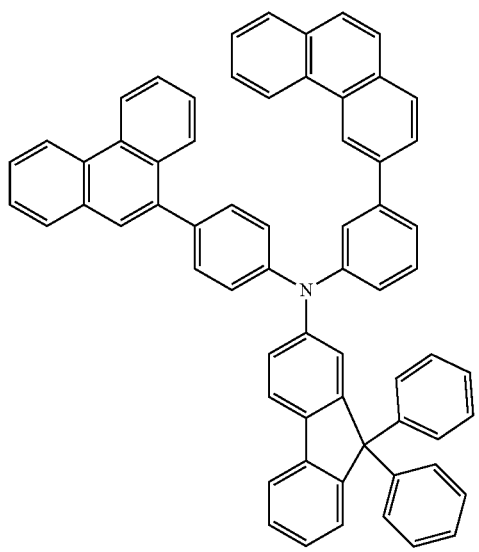
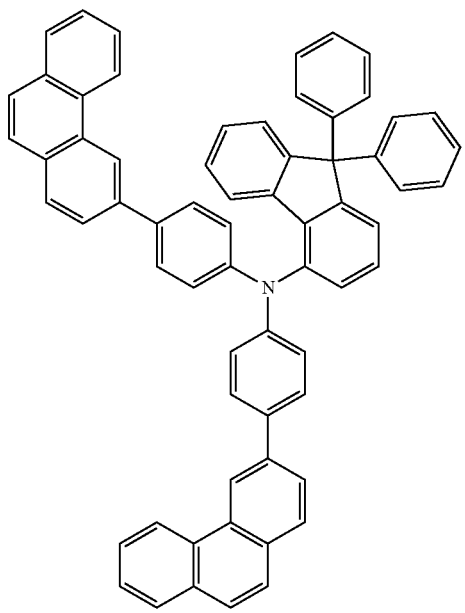

171
-continued

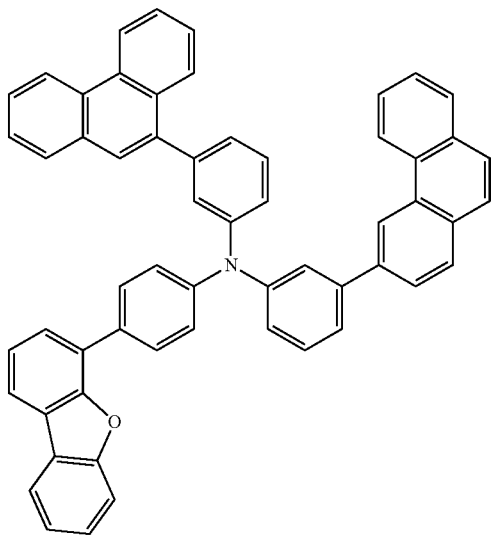

172
-continued

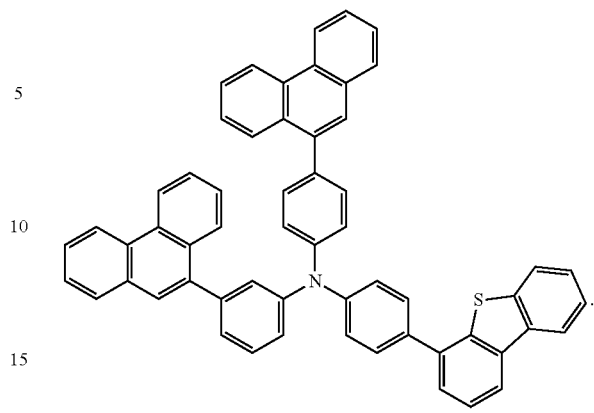

10. An organic electroluminescent device, comprising:
a first electrode;
a second electrode provided at a side opposite to the first electrode; and
at least one layer of the organic material layers provided between the first electrode and the second electrode, wherein the at least one layer of the organic material layers includes the compound of claim 9.

* * * * *

UNITED STATES PATENT AND TRADEMARK OFFICE
CERTIFICATE OF CORRECTION

PATENT NO. : 11,659,764 B2
APPLICATION NO. : 16/622227
DATED : May 23, 2023
INVENTOR(S) : Jae Seung Ha et al.

It is certified that error appears in the above-identified patent and that said Letters Patent is hereby corrected as shown below:

In the Claims

In Claim 1, at Column 105, Line 21, the text that reads:
"$C_{1-3}n$ alkyl"
Should read:
—$C_{1-30}$ alkyl—

Signed and Sealed this
Twenty-seventh Day of June, 2023

Katherine Kelly Vidal
*Director of the United States Patent and Trademark Office*